(12) United States Patent
Fallon et al.

(10) Patent No.: US 12,226,464 B2
(45) Date of Patent: Feb. 18, 2025

(54) COMPOSITIONS FOR TREATING ADDICTION

(71) Applicant: Curemark, LLC, Rye Brook, NY (US)

(72) Inventors: Joan M. Fallon, White Plains, NY (US); Matthew F. Heil, Sherman, CT (US)

(73) Assignee: Curemark, LLC, Rye Brook, NY (US)

( * ) Notice: Subject to any disclaimer, the term of this patent is extended or adjusted under 35 U.S.C. 154(b) by 1168 days.

(21) Appl. No.: 16/499,988

(22) PCT Filed: Apr. 10, 2018

(86) PCT No.: PCT/US2018/026841
§ 371 (c)(1),
(2) Date: Oct. 1, 2019

(87) PCT Pub. No.: WO2018/191233
PCT Pub. Date: Oct. 18, 2018

(65) Prior Publication Data
US 2020/0101145 A1    Apr. 2, 2020

Related U.S. Application Data

(60) Provisional application No. 62/483,856, filed on Apr. 10, 2017.

(51) Int. Cl.
| | | |
|---|---|---|
| *A61K 38/54* | (2006.01) | |
| *A61K 9/48* | (2006.01) | |
| *A61K 9/50* | (2006.01) | |
| *A61P 25/36* | (2006.01) | |
| *A61K 45/06* | (2006.01) | |

(52) U.S. Cl.
CPC ............ *A61K 38/54* (2013.01); *A61K 9/4808* (2013.01); *A61K 9/4825* (2013.01); *A61K 9/4891* (2013.01); *A61K 9/5015* (2013.01); *A61P 25/36* (2018.01); *A61K 45/06* (2013.01)

(58) Field of Classification Search
CPC .... A61K 38/54; A61K 9/4808; A61K 9/4825; A61K 9/4891; A61K 9/5015; A61K 45/06; A61P 25/36; A61P 25/30
See application file for complete search history.

(56) References Cited

U.S. PATENT DOCUMENTS

| | | | |
|---|---|---|---|
| 3,002,883 A | 10/1961 | Butt et al. | |
| 3,223,594 A | 12/1965 | Hoek | |
| 3,322,626 A | 5/1967 | D'Argento | |
| 3,357,894 A | 12/1967 | Uriel et al. | |
| 3,515,642 A | 6/1970 | Hiroyuki et al. | |
| 3,536,809 A | 10/1970 | Applezweig et al. | |
| 3,574,819 A | 4/1971 | Franz et al. | |
| 3,598,123 A | 8/1971 | Zaffaroni | |
| 3,710,795 A | 1/1973 | Higuchi et al. | |
| 3,786,615 A | 1/1974 | Bauer | |
| 3,845,770 A | 11/1974 | Theeuwes et al. | |
| 3,849,254 A | 11/1974 | Kirwan et al. | |
| 3,860,708 A | 1/1975 | Prout | |
| 3,916,899 A | 11/1975 | Theeuwes et al. | |
| 3,940,478 A | 2/1976 | Kurtz | |
| RE28,819 E | 5/1976 | Thompson | |
| 4,008,719 A | 2/1977 | Theeuwes et al. | |
| 4,044,126 A | 8/1977 | Cook et al. | |
| 4,079,125 A | 3/1978 | Sipos | |
| 4,145,410 A | 3/1979 | Sears | |
| 4,199,322 A | 4/1980 | Danna et al. | |
| 4,241,046 A | 12/1980 | Papahadjopoulos et al. | |
| 4,280,971 A | 7/1981 | Wischniewski et al. | |
| 4,328,245 A | 5/1982 | Yu et al. | |
| 4,358,603 A | 11/1982 | Yu | |
| 4,364,923 A | 12/1982 | Cook et al. | |
| 4,395,454 A | 7/1983 | Baldwin | |
| 4,409,239 A | 10/1983 | Yu | |
| 4,410,545 A | 10/1983 | Yu et al. | |
| 4,414,209 A | 11/1983 | Cook et al. | |
| 4,447,412 A | 5/1984 | Bilton | |
| 4,456,544 A | 6/1984 | Lupova et al. | |
| 4,500,515 A | 2/1985 | Libby | |
| 4,623,624 A | 11/1986 | Schultze | |
| 4,710,384 A | 12/1987 | Rotman | |
| 4,826,679 A | 5/1989 | Roy | |
| 4,965,012 A | 10/1990 | Olson | |
| 5,023,108 A | 6/1991 | Bagaria et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,190,775 A | 3/1993 | Klose | |
| 5,227,166 A | 7/1993 | Ueda et al. | |
| 5,250,418 A | 10/1993 | Moeller et al. | |

(Continued)

FOREIGN PATENT DOCUMENTS

| | | |
|---|---|---|
| CA | 2198317 A1 | 8/1998 |
| CA | 2263703 A1 | 8/1999 |

(Continued)

OTHER PUBLICATIONS

Amsterdam, D. Susceptibility testing of antimicrobials in liquid media. Antibiotics in Laboratory Medicine. 52-111 (1996).

(Continued)

*Primary Examiner* — Jessica Worsham

(74) *Attorney, Agent, or Firm* — Wilson Sonsini Goodrich & Rosati

(57) ABSTRACT

A pharmaceutical composition for use in the treatment of the symptoms of an addiction is disclosed. The pharmaceutical composition contains, but is not limited to, digestive enzymes. The pharmaceutical composition may further contain a coating that surrounds a core of digestive enzymes in the form of coated particles. The pharmaceutical composition may also be encapsulated. The therapeutic agent may be manufactured by a variety of technologies.

35 Claims, 3 Drawing Sheets

(56) References Cited

U.S. PATENT DOCUMENTS

| | | | |
|---|---|---|---|
| 5,324,514 | A | 6/1994 | Sipos |
| 5,354,556 | A | 10/1994 | Sparks et al. |
| 5,378,462 | A | 1/1995 | Boedecker et al. |
| 5,436,319 | A | 7/1995 | Kung et al. |
| 5,437,319 | A | 8/1995 | Garuglieri |
| 5,439,935 | A | 8/1995 | Rawlings et al. |
| 5,460,812 | A | 10/1995 | Sipos |
| 5,476,661 | A | 12/1995 | Pillai et al. |
| 5,527,678 | A | 6/1996 | Blaser et al. |
| 5,585,115 | A | 12/1996 | Sherwood et al. |
| 5,591,767 | A | 1/1997 | Mohr et al. |
| 5,607,863 | A | 3/1997 | Chandler |
| 5,639,476 | A | 6/1997 | Oshlack et al. |
| 5,648,335 | A | 7/1997 | Lewis et al. |
| 5,674,532 | A | 10/1997 | Atzl et al. |
| 5,674,533 | A | 10/1997 | Santus et al. |
| 5,686,255 | A | 11/1997 | Deth |
| 5,686,311 | A | 11/1997 | Shaw |
| 5,750,104 | A | 5/1998 | Sipos |
| 5,753,223 | A | 5/1998 | Shibahara et al. |
| 5,776,917 | A | 7/1998 | Blank et al. |
| 5,858,758 | A | 1/1999 | Hillman et al. |
| 5,860,957 | A | 1/1999 | Jacobsen et al. |
| 5,948,433 | A | 9/1999 | Burton et al. |
| 5,952,178 | A | 9/1999 | Lapidus et al. |
| 5,958,875 | A | 9/1999 | Longo et al. |
| 5,977,175 | A | 11/1999 | Lin |
| 5,983,134 | A | 11/1999 | Ostrow |
| 5,985,317 | A | 11/1999 | Venkateshwaran et al. |
| 5,985,891 | A | 11/1999 | Rowe |
| 6,010,715 | A | 1/2000 | Wick et al. |
| 6,011,001 | A | 1/2000 | Navia et al. |
| 6,013,286 | A | 1/2000 | Klose |
| 6,020,310 | A | 2/2000 | Beck et al. |
| 6,020,314 | A | 2/2000 | Mcmichael |
| 6,024,975 | A | 2/2000 | D'Angelo et al. |
| 6,096,338 | A | 8/2000 | Lacy et al. |
| 6,100,080 | A | 8/2000 | Johansen |
| 6,149,585 | A | 11/2000 | Gray |
| 6,153,236 | A | 11/2000 | Wu et al. |
| 6,167,301 | A | 12/2000 | Flower et al. |
| 6,168,569 | B1 | 1/2001 | Mcewen et al. |
| 6,187,309 | B1 | 2/2001 | Mcmichael et al. |
| 6,197,746 | B1 | 3/2001 | Beck et al. |
| 6,210,950 | B1 | 4/2001 | Johnson et al. |
| 6,238,727 | B1 | 5/2001 | Takemoto et al. |
| 6,251,478 | B1 | 6/2001 | Pacifico et al. |
| 6,256,533 | B1 | 7/2001 | Yuzhakov et al. |
| 6,261,595 | B1 | 7/2001 | Stanley et al. |
| 6,261,602 | B1 | 7/2001 | Calanchi et al. |
| 6,261,613 | B1 | 7/2001 | Narayanaswamy et al. |
| 6,267,983 | B1 | 7/2001 | Fujii et al. |
| 6,280,726 | B1 | 8/2001 | Weinrauch et al. |
| 6,287,585 | B1 | 9/2001 | Johansen |
| 6,309,669 | B1 | 10/2001 | Setterstrom et al. |
| 6,312,741 | B1 | 11/2001 | Navarro |
| 6,399,101 | B1 | 6/2002 | Frontanes et al. |
| 6,482,839 | B1 | 11/2002 | Thornfeldt |
| 6,498,143 | B1 | 12/2002 | Beck et al. |
| 6,534,063 | B1 | 3/2003 | Fallon |
| 6,534,259 | B1 | 3/2003 | Wakefield |
| 6,558,708 | B1 | 5/2003 | Lin |
| 6,562,629 | B1 | 5/2003 | Lin et al. |
| 6,569,463 | B2 | 5/2003 | Patel et al. |
| 6,616,954 | B1 | 9/2003 | Dally et al. |
| 6,632,429 | B1 | 10/2003 | Fallon |
| 6,660,831 | B2 | 12/2003 | Fallon |
| 6,699,885 | B2 | 3/2004 | Phillips |
| 6,727,073 | B1 | 4/2004 | Moore et al. |
| 6,743,447 | B2 | 6/2004 | Labergerie et al. |
| 6,764,447 | B2 | 7/2004 | Iliff |
| 6,783,757 | B2 | 8/2004 | Brudnak |
| 6,790,825 | B2 | 9/2004 | Beck et al. |
| 6,797,291 | B2 | 9/2004 | Richardson |
| 6,808,708 | B2 | 10/2004 | Houston |
| 6,821,514 | B2 | 11/2004 | Houston |
| 6,827,688 | B2 | 12/2004 | Goto et al. |
| 6,835,397 | B2 | 12/2004 | Lee et al. |
| 6,852,487 | B1 | 2/2005 | Barany et al. |
| 6,861,053 | B1 | 3/2005 | Lin et al. |
| 6,890,561 | B1 | 5/2005 | Blatt et al. |
| 6,899,876 | B2 | 5/2005 | Houston |
| 6,923,988 | B2 | 8/2005 | Patel et al. |
| 6,980,958 | B1 | 12/2005 | Surwit et al. |
| 7,048,906 | B2 | 5/2006 | Lin et al. |
| 7,081,239 | B2 | 7/2006 | Lin |
| 7,091,182 | B2 | 8/2006 | Beck et al. |
| 7,101,573 | B2 | 9/2006 | Szymczak et al. |
| 7,122,357 | B2 | 10/2006 | Sander-Struckmeier et al. |
| 7,129,053 | B1 | 10/2006 | Reiter et al. |
| 7,138,123 | B2 | 11/2006 | Fallon |
| 7,232,670 | B2 | 6/2007 | D'Azzo et al. |
| 7,244,412 | B2 | 7/2007 | Lin |
| 7,285,633 | B2 | 10/2007 | Wu et al. |
| RE40,059 | E | 2/2008 | Pacifico et al. |
| 7,381,698 | B2 | 6/2008 | Fein et al. |
| 7,395,216 | B2 | 7/2008 | Rosenfeld et al. |
| 7,479,378 | B2 | 1/2009 | Potthoff et al. |
| 7,483,747 | B2 | 1/2009 | Gliner et al. |
| 7,588,757 | B2 | 9/2009 | Ozawa et al. |
| 7,608,245 | B2 | 10/2009 | Lin |
| 7,630,913 | B2 | 12/2009 | Kay |
| 7,658,918 | B1 | 2/2010 | Ortenzi et al. |
| 7,718,169 | B2 | 5/2010 | Margolin et al. |
| 7,736,622 | B2 | 6/2010 | Lin et al. |
| 7,935,799 | B2 | 5/2011 | Lin et al. |
| 7,945,451 | B2 | 5/2011 | Cosentino et al. |
| 8,008,036 | B2 | 8/2011 | Fallon |
| 8,012,710 | B2 | 9/2011 | Fallon |
| 8,012,930 | B2 | 9/2011 | Fallon |
| 8,030,002 | B2 | 10/2011 | Fallon |
| 8,055,516 | B2 | 11/2011 | Iliff |
| 8,066,636 | B2 | 11/2011 | Iliff |
| 8,084,025 | B2 | 12/2011 | Fallon |
| 8,105,584 | B2 | 1/2012 | Fallon |
| 8,163,278 | B2 | 4/2012 | Fallon |
| 8,211,661 | B2 | 7/2012 | Fallon |
| 8,221,747 | B2 | 7/2012 | Ortenzi et al. |
| 8,318,158 | B2 | 11/2012 | Fallon |
| 8,437,689 | B2 | 5/2013 | Mazar |
| 8,486,390 | B2 | 7/2013 | Fallon |
| 8,580,522 | B2 | 11/2013 | Fallon |
| 8,613,918 | B2 | 12/2013 | Fallon |
| 8,658,163 | B2 | 2/2014 | Fallon |
| 8,673,877 | B2 | 3/2014 | Fallon et al. |
| 8,778,335 | B2 | 7/2014 | Fallon |
| 8,815,233 | B2 | 8/2014 | Fallon |
| 8,921,054 | B2 | 12/2014 | Fallon |
| 8,980,252 | B2 | 3/2015 | Fallon et al. |
| 9,017,665 | B2 | 4/2015 | Fallon |
| 9,023,344 | B2 | 5/2015 | Fallon |
| 9,056,050 | B2 | 6/2015 | Fallon et al. |
| 9,061,033 | B2 | 6/2015 | Fallon |
| 9,084,784 | B2 | 7/2015 | Fallon et al. |
| 9,107,419 | B2 | 8/2015 | Fallon et al. |
| 9,233,146 | B2 | 1/2016 | Fallon |
| 9,320,780 | B2 | 4/2016 | Fallon |
| 9,345,721 | B2 | 5/2016 | Fallon et al. |
| 9,377,459 | B2 | 6/2016 | Fallon |
| 9,408,895 | B2 | 8/2016 | Fallon |
| 9,415,014 | B2 | 8/2016 | Fallon et al. |
| 9,492,515 | B2 | 11/2016 | Fallon et al. |
| 9,511,125 | B2 | 12/2016 | Fallon et al. |
| 9,624,525 | B2 | 4/2017 | Fallon |
| 9,624,526 | B2 | 4/2017 | Fallon |
| 9,687,452 | B2 | 6/2017 | Fallon et al. |
| 9,687,534 | B2 | 6/2017 | Fallon |
| 9,687,535 | B2 | 6/2017 | Fallon |
| 9,895,427 | B2 | 2/2018 | Fallon et al. |
| 9,925,250 | B2 | 3/2018 | Fallon |
| 9,931,302 | B2 | 4/2018 | Fallon et al. |
| 10,098,844 | B2 | 10/2018 | Fallon et al. |
| 10,209,253 | B2 | 2/2019 | Fallon |
| 10,272,141 | B2 | 4/2019 | Fallon |

(56) References Cited

U.S. PATENT DOCUMENTS

| | | |
|---|---|---|
| 10,279,016 B2 | 5/2019 | Fallon |
| 10,350,229 B2 | 7/2019 | Fallon et al. |
| 10,350,278 B2 | 7/2019 | Fallon et al. |
| 10,413,601 B2 | 9/2019 | Fallon |
| 2001/0006644 A1 | 7/2001 | Bova et al. |
| 2001/0023360 A1 | 9/2001 | Nelson et al. |
| 2001/0024660 A1 | 9/2001 | Ullah et al. |
| 2002/0001575 A1 | 1/2002 | Foreman |
| 2002/0037284 A1 | 3/2002 | Fallon |
| 2002/0061302 A1 | 5/2002 | Sander-Struckmeier et al. |
| 2002/0081628 A1 | 6/2002 | Fallon |
| 2002/0090653 A1 | 7/2002 | Fallon |
| 2002/0094367 A1 | 7/2002 | Fuglsang et al. |
| 2002/0103675 A1 | 8/2002 | Vanelli |
| 2002/0119914 A1 | 8/2002 | Zhu et al. |
| 2002/0141987 A1 | 10/2002 | Bjarnason |
| 2002/0183229 A1 | 12/2002 | Simpson |
| 2003/0097122 A1 | 5/2003 | Ganz et al. |
| 2004/0005304 A1 | 1/2004 | Brudnak |
| 2004/0028689 A1 | 2/2004 | Borody |
| 2004/0029752 A1 | 2/2004 | Sava et al. |
| 2004/0057944 A1 | 3/2004 | Galle et al. |
| 2004/0057962 A1 | 3/2004 | Timmerman |
| 2004/0071683 A1 | 4/2004 | Fallon |
| 2004/0076590 A1 | 4/2004 | Wilkins |
| 2004/0101562 A1 | 5/2004 | Maio |
| 2004/0121002 A1 | 6/2004 | Lee et al. |
| 2004/0209790 A1 | 10/2004 | Sava et al. |
| 2005/0026892 A1 | 2/2005 | Bodor |
| 2005/0036950 A1 | 2/2005 | Jones et al. |
| 2005/0079594 A1 | 4/2005 | Marion |
| 2005/0137134 A1 | 6/2005 | Gill et al. |
| 2005/0170479 A1 | 8/2005 | Weaver et al. |
| 2005/0187130 A1 | 8/2005 | Brooker et al. |
| 2005/0232894 A1 | 10/2005 | Weiner et al. |
| 2006/0105379 A1 | 5/2006 | Wu et al. |
| 2006/0115467 A1 | 6/2006 | Pangborn et al. |
| 2006/0121017 A1 | 6/2006 | Margolin et al. |
| 2006/0182728 A1 | 8/2006 | Fallon |
| 2006/0183180 A1 | 8/2006 | Fallon |
| 2006/0198838 A1 | 9/2006 | Fallon |
| 2006/0253045 A1 | 11/2006 | Coifman |
| 2006/0258599 A1 | 11/2006 | Childers |
| 2006/0258708 A1 | 11/2006 | Andrulis |
| 2006/0259995 A1 | 11/2006 | Cayouette et al. |
| 2006/0294108 A1 | 12/2006 | Adelson et al. |
| 2007/0031399 A1 | 2/2007 | Edens et al. |
| 2007/0053895 A1 | 3/2007 | Fallon |
| 2007/0092501 A1 | 4/2007 | Houston |
| 2007/0116695 A1 | 5/2007 | Fallon |
| 2007/0148151 A1 | 6/2007 | Frink et al. |
| 2007/0148152 A1 | 6/2007 | Shlieout et al. |
| 2007/0148153 A1 | 6/2007 | Shlieout et al. |
| 2007/0203426 A1 | 8/2007 | Kover et al. |
| 2008/0019959 A1 | 1/2008 | Becher et al. |
| 2008/0020036 A1 | 1/2008 | Jolly |
| 2008/0057086 A1 | 3/2008 | Etter |
| 2008/0058282 A1 | 3/2008 | Fallon et al. |
| 2008/0112900 A1 | 5/2008 | Du-Thumm et al. |
| 2008/0112944 A1 | 5/2008 | Pangborn et al. |
| 2008/0152637 A1 | 6/2008 | Fallon |
| 2008/0161265 A1 | 7/2008 | Fallon et al. |
| 2008/0166334 A1 | 7/2008 | Fallon |
| 2008/0177578 A1 | 7/2008 | Zakim |
| 2008/0187525 A1 | 8/2008 | Porubcan |
| 2008/0193436 A1 | 8/2008 | Shan et al. |
| 2008/0199448 A1 | 8/2008 | Ross et al. |
| 2008/0219966 A1 | 9/2008 | Fallon |
| 2008/0248558 A1 | 10/2008 | Deinhammer et al. |
| 2008/0254009 A1 | 10/2008 | Finegold |
| 2008/0274174 A1 | 11/2008 | Ortenzi et al. |
| 2008/0279839 A1 | 11/2008 | Schuler et al. |
| 2008/0279953 A1 | 11/2008 | Ortenzi et al. |
| 2008/0311554 A1 | 12/2008 | Slotman |
| 2008/0317731 A1 | 12/2008 | Gramatikova et al. |
| 2009/0004285 A1 | 1/2009 | Yu et al. |
| 2009/0063402 A1 | 3/2009 | Hayter |
| 2009/0110674 A1 | 4/2009 | Loizou |
| 2009/0117180 A1 | 5/2009 | Ortenzi et al. |
| 2009/0130081 A1 | 5/2009 | Fallon |
| 2009/0171696 A1 | 7/2009 | Allard et al. |
| 2009/0197289 A1 | 8/2009 | Fallon |
| 2009/0226414 A1 | 9/2009 | Tijssen et al. |
| 2009/0232789 A1 | 9/2009 | Fallon |
| 2009/0233344 A1 | 9/2009 | Kurfurst et al. |
| 2009/0263372 A1 | 10/2009 | Fallon |
| 2009/0285790 A1 | 11/2009 | Fallon |
| 2009/0286270 A1 | 11/2009 | Fallon |
| 2009/0304670 A1 | 12/2009 | Edens et al. |
| 2009/0324572 A1 | 12/2009 | Fallon |
| 2009/0324730 A1 | 12/2009 | Fallon |
| 2010/0092447 A1 | 4/2010 | Fallon |
| 2010/0169409 A1 | 7/2010 | Fallon et al. |
| 2010/0196344 A1 | 8/2010 | Margolin et al. |
| 2010/0209507 A1 | 8/2010 | Lin et al. |
| 2010/0233218 A1 | 9/2010 | Fallon |
| 2010/0239559 A1 | 9/2010 | Freedman et al. |
| 2010/0260857 A1 | 10/2010 | Fallon et al. |
| 2010/0270183 A1 | 10/2010 | Ortenzi et al. |
| 2010/0285116 A1 | 11/2010 | Joshi |
| 2011/0029922 A1 | 2/2011 | Hoffberg et al. |
| 2011/0052706 A1 | 3/2011 | Moest et al. |
| 2011/0065628 A1 | 3/2011 | Johnson et al. |
| 2011/0081320 A1 | 4/2011 | Westall et al. |
| 2011/0112005 A1 | 5/2011 | Brooker et al. |
| 2011/0182818 A1 | 7/2011 | Fallon |
| 2011/0200574 A1 | 8/2011 | Jolly et al. |
| 2011/0280853 A1 | 11/2011 | Fallon et al. |
| 2011/0280854 A1 | 11/2011 | Fallon et al. |
| 2012/0003628 A1 | 1/2012 | Fallon |
| 2012/0004192 A1 | 1/2012 | Fallon et al. |
| 2012/0070504 A1 | 3/2012 | Fallon |
| 2012/0128764 A1 | 5/2012 | Venkatesh et al. |
| 2012/0189703 A1 | 7/2012 | Fallon et al. |
| 2012/0201875 A1 | 8/2012 | Ortenzi et al. |
| 2012/0207740 A1 | 8/2012 | Fallon |
| 2012/0230970 A1 | 9/2012 | Fallon |
| 2013/0059001 A1 | 3/2013 | Fallon |
| 2013/0095152 A1 | 4/2013 | Fallon |
| 2013/0113129 A1 | 5/2013 | Fallon et al. |
| 2013/0171121 A1 | 7/2013 | Pierzynowski et al. |
| 2013/0195833 A1 | 8/2013 | Fallon |
| 2013/0202581 A1 | 8/2013 | Fallon et al. |
| 2013/0224172 A1 | 8/2013 | Fallon et al. |
| 2013/0323223 A1* | 12/2013 | Fallon ............... A61P 1/14 424/94.2 |
| 2014/0030333 A1 | 1/2014 | Fallon |
| 2014/0127184 A1 | 5/2014 | Fallon et al. |
| 2014/0147500 A1 | 5/2014 | Fallon et al. |
| 2014/0161787 A1 | 6/2014 | Fallon |
| 2014/0170637 A1 | 6/2014 | Fallon |
| 2014/0348881 A1 | 11/2014 | Fallon |
| 2015/0023944 A1 | 1/2015 | Fallon |
| 2015/0147308 A1 | 5/2015 | Fallon et al. |
| 2015/0151198 A1 | 6/2015 | Dugan et al. |
| 2015/0182607 A1 | 7/2015 | Jolly et al. |
| 2015/0246105 A1 | 9/2015 | Fallon et al. |
| 2016/0045576 A1 | 2/2016 | Fallon et al. |
| 2016/0206708 A1 | 7/2016 | Fallon et al. |
| 2017/0157221 A1 | 6/2017 | Fallon |
| 2017/0202934 A1 | 7/2017 | Fallon et al. |
| 2017/0246265 A1 | 8/2017 | Fallon |
| 2018/0071375 A1 | 3/2018 | Fallon |
| 2018/0104315 A1 | 4/2018 | Fallon |
| 2018/0161409 A1 | 6/2018 | Fallon |
| 2018/0243282 A1 | 8/2018 | Fallon |
| 2018/0296650 A1 | 10/2018 | Fallon |
| 2018/0360759 A1 | 12/2018 | Fallon |
| 2019/0175704 A1 | 6/2019 | Fallon |
| 2019/0183990 A1 | 6/2019 | Fallon et al. |
| 2019/0201507 A1 | 7/2019 | Fallon |
| 2019/0209667 A1 | 7/2019 | Fallon |
| 2019/0275066 A1 | 9/2019 | Fallon et al. |
| 2019/0275128 A1 | 9/2019 | Gleiberman et al. |

(56) References Cited

U.S. PATENT DOCUMENTS

| | | | |
|---|---|---|---|
| 2020/0282030 A1 | 9/2020 | Fallon et al. | |
| 2020/0286620 A1 | 9/2020 | Fallon et al. | |
| 2021/0162024 A1 | 6/2021 | Fallon et al. | |
| 2022/0096611 A1 | 3/2022 | Fallon et al. | |

FOREIGN PATENT DOCUMENTS

| | | |
|---|---|---|
| CA | 2041871 C | 7/2000 |
| CA | 2667976 A1 | 5/2008 |
| CA | 2719102 A1 | 9/2009 |
| CN | 1031562 A | 3/1989 |
| CN | 1275897 A | 12/2000 |
| CN | 1329923 A | 1/2002 |
| CN | 1552836 A | 12/2004 |
| CN | 1791430 A | 6/2006 |
| CN | 101039667 A | 9/2007 |
| CN | 101208092 A | 6/2008 |
| CN | 102300989 A | 12/2011 |
| DE | 3738599 A1 | 5/1989 |
| DE | 4332985 A1 | 3/1995 |
| DE | 202010004926 U1 | 7/2010 |
| EP | 0425214 A2 | 5/1991 |
| EP | 0436110 A1 | 7/1991 |
| EP | 0451484 A1 | 10/1991 |
| EP | 0564739 A2 | 10/1993 |
| EP | 0564739 A3 | 4/1995 |
| EP | 1162995 B1 | 6/2003 |
| EP | 1413202 A1 | 4/2004 |
| EP | 1335706 B1 | 4/2005 |
| EP | 1019072 B1 | 5/2005 |
| EP | 1604677 A1 | 12/2005 |
| EP | 1931317 B1 | 12/2008 |
| EP | 2258837 A1 | 12/2010 |
| EP | 2318035 A1 | 5/2011 |
| EP | 2373791 A1 | 10/2011 |
| GB | 669782 A | 4/1952 |
| GB | 2347742 A | 9/2000 |
| GB | 2480772 A | 11/2011 |
| GB | 2506537 A | 4/2014 |
| JP | S523819 A | 1/1977 |
| JP | S62230714 A | 10/1987 |
| JP | H04364119 A | 12/1992 |
| JP | 2003517831 A | 6/2003 |
| JP | 2004500591 A | 1/2004 |
| JP | 2005515223 A | 5/2005 |
| JP | 2006512091 A | 4/2006 |
| JP | 2007523664 A | 8/2007 |
| JP | 2007530503 A | 11/2007 |
| JP | 2008512468 A | 4/2008 |
| JP | 2008521906 A | 6/2008 |
| JP | 2008283895 A | 11/2008 |
| JP | 2013517251 A | 5/2013 |
| KR | 20050084485 A | 8/2005 |
| RU | 2356244 C1 | 5/2009 |
| TW | 310277 B | 7/1997 |
| WO | WO-8402846 A1 | 8/1984 |
| WO | WO-8903211 A1 | 4/1989 |
| WO | WO-8908694 A1 | 9/1989 |
| WO | WO-9002562 A1 | 3/1990 |
| WO | WO-9219708 A1 | 11/1992 |
| WO | WO-9219709 A1 | 11/1992 |
| WO | WO-9419005 A1 | 9/1994 |
| WO | WO-9522344 A1 | 8/1995 |
| WO | WO-9732480 A1 | 9/1997 |
| WO | WO-9822499 A2 | 5/1998 |
| WO | WO-9826807 A1 | 6/1998 |
| WO | WO-9822499 A3 | 7/1998 |
| WO | WO-9832336 A2 | 7/1998 |
| WO | WO-9852593 A1 | 11/1998 |
| WO | WO-9964059 A2 | 12/1999 |
| WO | WO-0009142 A1 | 2/2000 |
| WO | WO-9964059 A3 | 3/2000 |
| WO | WO-0021504 A1 | 4/2000 |
| WO | WO-0127612 A2 | 4/2001 |
| WO | WO-0143764 A2 | 6/2001 |
| WO | WO-0145835 A1 | 6/2001 |
| WO | WO-0127612 A3 | 10/2001 |
| WO | WO-0143764 A3 | 11/2001 |
| WO | WO-0214537 A2 | 2/2002 |
| WO | WO-0219828 A1 | 3/2002 |
| WO | WO-0214537 A3 | 5/2002 |
| WO | WO-02051352 A2 | 7/2002 |
| WO | WO-02051436 A2 | 7/2002 |
| WO | WO-03051345 A2 | 6/2003 |
| WO | WO-03059088 A1 | 7/2003 |
| WO | WO-2004060074 A1 | 7/2004 |
| WO | WO-2004093883 A2 | 11/2004 |
| WO | WO-2005092370 A1 | 10/2005 |
| WO | WO-2005115445 A1 | 12/2005 |
| WO | WO-2006031554 A2 | 3/2006 |
| WO | WO-2006044529 A1 | 4/2006 |
| WO | WO-2006060414 A2 | 6/2006 |
| WO | WO-2006031554 A3 | 9/2006 |
| WO | WO-2007002572 A2 | 1/2007 |
| WO | WO-2007074454 A2 | 7/2007 |
| WO | WO-2007147714 A1 | 12/2007 |
| WO | WO-2008021987 A2 | 2/2008 |
| WO | WO-2008102264 A2 | 8/2008 |
| WO | WO-2009114757 A2 | 9/2009 |
| WO | WO-2009155689 A1 | 12/2009 |
| WO | WO-2010002972 A1 | 1/2010 |
| WO | WO-2010025126 A1 | 3/2010 |
| WO | WO-2010080830 A1 | 7/2010 |
| WO | WO-2010080835 A1 | 7/2010 |
| WO | WO-2010120781 A1 | 10/2010 |
| WO | WO-2011000924 A1 | 1/2011 |
| WO | WO-2011050135 A1 | 4/2011 |
| WO | WO-2011086126 A1 | 7/2011 |
| WO | WO-2011114225 A1 | 9/2011 |
| WO | WO-2012067621 A1 | 5/2012 |
| WO | WO-2012145651 A2 | 10/2012 |
| WO | WO-2013103746 A1 | 7/2013 |
| WO | WO-2013116732 A1 | 8/2013 |
| WO | WO-2013181447 A1 | 12/2013 |
| WO | WO-2018191233 A1 | 10/2018 |

OTHER PUBLICATIONS

Barboza et al., Measurement of intestinal permeability using mannitol and lactulose in children with diarrheal diseases. Brazilian Journal of Medical and Biological Research 32: 1499-1504 (1999).

Barry, J. Mode of action of penetration enhancers in human skin. Controlled Release 6: 85-97 (1987).

Capua et al., Influenza A viruses grow in human pancreatic cells and cause pancreatitis and diabetes in an animal model. Journal of Virology 87(1): 597-610 (2013).

Defelice, Viruses Part 2-results of two informal studies, Chapter 14. In: Enzymes: Go with your Gut-more practical guidelines for digestive enzymes. Published by ThunderSnow. pp. 195-218 (2006).

D'Eufemia et al., Abnormal intestinal permeability in children with autism. Acta Paediatr 85: 1076-1079 (1996).

European Patent Application No. EP19193479.3 Extended Search Report dated Mar. 31, 2020.

Horsmans et al., Lactulose improves psychometric testing in cirrhotic patients with subclinical encephalopathy. Aliment Pharmocol Ther 11:165-170 (1997).

National Institutes of Health. Thin Bones Seen in Boys with Autism and Autism Spectrum Disorder. 3 pages (2008).

Schlessingerman, Mass of an Adult. The Physics Factbook (2003).

U.S. Appl. No. 13/733,873 Final Office Action Mailed Feb. 6, 2020.

U.S. Appl. No. 15/889,917 Final Office Action Mailed Feb. 13, 2020.

U.S. Appl. No. 12/535,676 Notice of Allowance mailed Apr. 1, 2020.

U.S. Appl. No. 13/002,136 Non-Final Office Action dated May 26, 2020.

U.S. Appl. No. 13/757,412 Non-Final Office Action dated Mar. 18, 2020.

U.S. Appl. No. 14/713,242 Notice of Allowance mailed Apr. 2, 2020.

(56) References Cited

OTHER PUBLICATIONS

U.S. Appl. No. 15/074,115 Notice of Allowance dated Dec. 11, 2019.
U.S. Appl. No. 15/074,115 Notice of Allowance dated Feb. 11, 2020.
U.S. Appl. No. 15/265,620 Non-Final Office Action dated Jan. 30, 2020.
U.S. Appl. No. 15/265,620 Notice of Allowance dated Apr. 29, 2020.
U.S. Appl. No. 15/354,940 Final Office Action dated Jul. 2, 2020.
U.S. Appl. No. 15/840,883 Final Office Action dated Jun. 9, 2020.
U.S. Appl. No. 15/889,917 Office Action dated May 24, 2019.
U.S. Appl. No. 16/281,908 Non-Final Office Action dated May 1, 2020.
U.S. Appl. No. 16/296,546 Non-Final Office Action dated Feb. 14, 2020.
U.S. Appl. No. 16/422,079 Non-Final Office Action dated Apr. 20, 2020.
Wang et al., Extraction of Pancreatin from Pig Pancreas and Isolation and Purification of Kallikrein. Academic Journal of Kunming Medical College 1: 107-108 (2002).
Beighley et al., Food Selectivity in Children With and Without an Autism Spectrum Disorder: Investigation of Diagnosis and Age. Res Dev Disabil 34(10): 3497-3503 (2013).
Demand et al., Psychometric Properties of the Brief Autism Mealtime Behaviors Inventory. J Autism Dev Disord 45(9):2667-2673 (2015).
Fan et al., Guidelines for Standard Operation of Toxicological Safety Assessment (vol. 1). University of Electronic Science and Technology Press (2009).
Harrison, Bipolar Disorder. Healing Depression Naturally, Twin Streams. Kensington Publishing Corp: 31-32. (2004).
Johnson et al., Relationships Between Feeding Problems, Behavioral Characteristics and Nutritional Quality in Children With Asd. J Autism Dev Disord 44(9): 2175-2184 (2014).
Mari-Bauset et al., Anthropometric measurements and nutritional assessment in autism spectrum disorders: A systematic review. Research in Autism Spectrum Disorders 9: 130-143 (2015).
Merriam Webster Dictionary: definition of prevent.
Sharp et al., Multi-method assessment of feeding problems among children with autism spectrum disorders. Research in Autism Spectrum Disorders 7(1): 56-65 (2013).
Shmaya et al., Meal Time Behavior Difficulties but Not Nutritional Deficiencies Correlate With Sensory Processing in Children With Autism Spectrum Disorder. Res Dev Disabil 66: 27-33 (2017).
Thomas, Bipolar Disorder-Balancing Moods by Balancing Nutrients; What Doctors Don't Tell You. 14)7): 1-13 (2003).
U.S. Appl. No. 13/002,136 Final Office Action dated Sep. 11, 2020.
U.S. Appl. No. 13/002,136 Notice of Allowance dated Feb. 24, 2021.
U.S. Appl. No. 13/757,412 Final Office Action dated Dec. 22, 2020.
U.S. Appl. No. 15/840,883 Non-Final Office Action dated Apr. 30, 2021.
U.S. Appl. No. 15/889,917 Non-Final Office Action dated Sep. 3, 2020.
U.S. Appl. No. 16/281,908 Notice of Allowance mailed Nov. 3, 2020.
U.S. Appl. No. 16/422,079 Final Office Action dated Sep. 16, 2020.
U.S. Appl. No. 16/422,462 Non-Final Office Action dated Jul. 22, 2021.
U.S. Appl. No. 16/884,701 Non-Final Office Action dated Jun. 10, 2021.
Xie, Development and Application of New Traditional Chinese Medicine 2nd Edition. People's Medical Publishing House (2000).
Beers et al., The Merck Manual of Diagnosis and Therapy. Eighteenth Edition. Section 15: 1683-1688 (2006).
Beers et al., The Merck Manual of Diagnosis and Therapy. Eighteenth Edition. Section 15: 1713-1717 (2006).
Beers et al., The Merck Manual of Diagnosis and Therapy. Eighteenth Edition. Section 19: 2308-2313 (2006).
Beers et al., The Merck Manual of Diagnosis and Therapy. Eighteenth Edition. Section 19: 2486-2489 (2006).
Nater et al., Determinants of the diurnal course of salivary alpha-amylase. Psychoneuroendocrinology 32: 392-401 (2007).
The Diagnostic and Statistical Manual of Mental Disorders (DSM IV), Substance Disorders, pp. 105-151. Published by the American Psychiatric Association, Fourth Edition, Primary Care Version, Washington, DC, American Psychiatric Association (2000).
Types of Fats, Healthwise-Mich Med, pp. 1-2, downloaded from htttps://www/uofmhealth.org/health-library/aa160619 on Feb. 3, 2021.
U.S. Appl. No. 15/889,917 Notice of Allowance dated Mar. 29, 2021.
U.S. Appl. No. 16/103,192 Non-Final Office Action dated Feb. 10, 2021.
U.S. Appl. No. 16/103,192 Non-Final Office Action dated Nov. 26, 2021.
U.S. Appl. No. 16/103,192 Notice of Allowance dated Jun. 6, 2022.
U.S. Appl. No. 16/281,937 Non-Final Office Action dated Mar. 17, 2021.
U.S. Appl. No. 16/281,937 Notice of Allowance dated Dec. 2, 2021.
U.S. Appl. No. 16/422,079 Notice of Allowance dated Mar. 3, 2021.
U.S. Appl. No. 16/883,297 Final Office Action dated Nov. 23, 2022.
U.S. Appl. No. 16/883,297 Non-Final Office Action dated Mar. 30, 2022.
U.S. Appl. No. 16/884,701 Non-Final Office Action dated Apr. 6, 2022.
U.S. Appl. No. 17/306,614 Non-Final Office Action dated Nov. 4, 2022.
U.S. Appl. No. 17/344,414 Non-Final Office Action dated Sep. 22, 2022.
ABCNEWS. Changing Face of Autism: Numbers Rise as More Behaviors Included. ABCnews. Nov. 1, 2007.
Adams. "Summary of Defeat Autism Now! (DNN!) Oct. 2001 Conference," retrieved from the internet Dec. 18, 2008. http://puterakembara.org/rm/DAN2001.htm.
Advisory Action dated Jun. 3, 2008 for U.S. Appl. No. 10/681,018.
Aman, et al. Outcome measures for clinical drug trials in autism. CNS Spectr. Jan. 2004;9(1):36-47.
American Family Physician. Cuts, Scrapes, and Stitches. Am Fam Physician 69(11):2647-2648 (Jun. 1, 2004).
Anderson, George M., et al. Determination of serotonin in whole blood, platelet-rich plasma, platelet-poor plasma and plasma ultrafiltrate. Life Sciences 40(11):1063-1070 (Mar. 16, 1987) [Abstract Only].
Ang, et al. Biological role and regulation of the universally conserved heat shock proteins. J Biol Chem. Dec. 25, 1991;266(36):24233-6.
Anonymous: Emulsifiers for the preparation of active dry yeast, Research Disclosure, Mason Publications, Hampshire, GB, 236(6), Dec. 1983 (attached).
APDA. Basic Information About Parkinson's Disease. Jul. 14, 2008.
Arnold, GL et al. Plasma amino acids profiles in children with autism: potential risk of nutritional deficiencies. J. Autism Dev. Disord. 33(4):449-454 (Aug. 2003) [Abstract Only].
Arribas, et al. A comparative study of the chymotrypsin-like activity of the rat liver multicatalytic proteinase and the ClpP from *Escherichia coli*. J Biol Chem. Oct. 5, 1993;268(28):21165-71.
Arrigo, et al. Expression of heat shock proteins during development in Drosophila. Results Probl Cell Differ. 1991;17:106-19.
Ash. Patient Information Guide—Understanding Hypertension. American Society of Hypertension. 2004. 1-7.
Ashwood, et al. Immune activation of peripheral blood and mucosal CD3+ lymphocyte cytokine profiles in children with autism and gastrointestinal symptoms. J Neuroimmunol. Dec. 19, 2005; 1-9.
Ashwood, et al. Intestinal lymphocyte populations in children with regressive autism: evidence for extensive mucosal immunopathology. J Clin Immunol. Nov. 2003;23(6):504-17.
Ashwood, et al. Spontaneous mucosal lymphocyte cytokine profiles in children with autism and gastrointestinal symptoms: mucosal immune activation and reduced counter regulatory interleukin-10. J Clin Immunol. Nov. 2004;24(6):664-73.
Austic. Development and adaptation of protein digestion. J Nutr. May 1985; 115(5):686-97.

(56) References Cited

OTHER PUBLICATIONS

Autism Diagnosis. Autism Statistics. Www.autism-diagnosis.com/autism_statistics/autism_statistics.html. 2007.
Autism Society of America. Incidence Numbers from Other Countries. www.autism-society.org. Accessed: Jul. 14, 2008.
Avruch, J., et al. Amino acid regulation of TOR complex 1. AJP: Endocrinology and Metabolism, Am. J. Physiol. Endocrinol. Metab. 296(4):E592-E602 (Apr. 2009).
Awazuhara, et al. Antigenicity of the proteins in soy lecithin and soy oil in soybean allergy. Clin Exp Allergy. Dec. 1998;28(12):1559-64.
Axcan Pharma Inc. Cdn Prescribing Information on VIOKASE Pancrelipase, USP tablets, powder. 2000: 1-3.
Axelrod FB et al. Hereditary sensory an autonomic neuropathies: types II, III and IV. Orphanet Journal of Rare Diseases, 2:39 (2007).
Axelrod. Secretin Treatment for Gastrointestinal Dysmobility in Patients with Familial Dysautonomia. New York University School of Medicine, Grant Recipient awards, Mar.-May 2000. www.med.nyu.edu/ogars/awards/awards2000/page2.html.
Azilect et al. "Correlation between protein intake and daily levodopa dosage," Obtained from the internet May 2, 2007, http://www.azilect.eu/media/cnsnews/showitem.aspx?i=d1c603e4-3c61-4aa1-a376-6e519a5a0f80.
Bailey, et al. Co-occurring conditions associated with FMR1 gene variations: findings from a national parent survey. Am J Med Genet A. Aug. 15, 2008;146A(16):2060-9.
Bakkaloglu, et al. Atopic features in early childhood autism. Eur J Paediatr Neurol. Nov. 2008;12(6):476-9.
Balasubramanian, Mukundh N. et al. Asparagine synthetase: regulation by cell stress and involvement in tumor biology, Am. J. Physiol. Endocrinol. Metab. 304(8):E789-E799 (Apr. 15, 2013).
Barlow. A comparison of the blood pressure, kidney vol. and the pancreatic secretory response following the vein administration of various secretin preparations. Am J Phys. 1927;81:182-188.
Barnhart, et al. Symptomatic granular cell tumor involving the pituitary gland in a dog: a case report and review of the literature. Vet Pathol. May 2001;38(3):332-6.
Beilmann, et al. Neoexpression of the c-met/hepatocyte growth factor-scatter factor receptor gene in activated monocytes. Blood. Dec. 1, 1997;90(11):4450-8.
Beliaev, O.A. The therapeutic efficacy of the triase preparation in experimental pancreatic exocrine insufficiency. Eksp Lin Farmakiol. 57:38-40 (1994) (Abstract Only—English Translation).
Bellanti, et al. Abnormalities of Th1 function in non-IgE food allergy, celiac disease, and ileal lymphonodular hyperplasia: a new relationship? Ann Allergy Asthma Immunol. Jun. 2003; 90(6 Suppl 3):84-9.
Belmonte et al. Fragile X syndrome and autism at the intersection of genetic and neural networks. Nat Neurosci. Oct. 2006; 9(10):1221-5 (abstract only).
Berg, et al. Section 10.5 Many Enzymes Are Activated by Specific Proteolytic Cleavage. 2002.
Berg, et al. Section 9.1 Proteases: Facilitating a Difficult Reaction. 2002.
Berg, et al. Table of Contents. Biochemistry, 5th edition. 2002.
Bhattacharjee et al., Treatment of Pancreatic Exocrine Insufficiency with Enteric Coated Pancreatin Formulations: An Overview. International Journal of Pharmaceutical Sciences and Nanotechnology. 6(3):2125-2130 (2013).
Birnbaum, et al. Heat shock or stress proteins and their role as autoantigens in multiple sclerosis. Ann N Y Acad Sci. Dec. 19, 1997;835:157-67. Abstract only.
Blackmer. Parkinson disease: treatment and medication. Mar. 10, 2009., retrieved from the internet on Sep. 15, 2009, http://emedicine.medscape.com/article/312519-treatment.
Block, et al. A rapid food screener to assess fat and fruit and vegetable intake. Am J Prev Med. May 2000; 18(4):284-8.
Blog. Acid Phosphatase Research (blog). Acid-phosphatase.blogspot.com. 2008.
Bode et al. Usefulness of a simple photometric determination of chymotrypsin activity in stools—results of a multicentre study. Clin Biochem. 1986; 19:333-37.
Boorom. Is this recently characterized gastrointestinal pathogen responsible for rising rates of inflammatory bowel disease (IBD) and IBD associated autism in Europe and the United States in the 1990s? Med Hypotheses. 2007;69(3):652-9.
Borlongan. Recent preclinical evidence advancing cell therapy for Alzheimer's disease. Exp Neurol. Sep. 2012;237(1):142-6. doi: 10.1016/j.expneurol.2012.06.024. Epub Jun. 27, 2012.
Borowitz et al., Study of a novel pancreatic enzyme replacement therapy in pancreatic insufficient subjects with cystic fibrosis J.Pediatr., 149:658-662 (2006).
Borowitz, et al. Use of pancreatic enzyme supplements for patients with cystic fibrosis in the context of fibrosing colonopathy. Consensus Committee. J Pediatr. Nov. 1995;127(5):681-4.
Bouhnik, et al. Lactulose ingestion increases faecal bifidobacterial counts: A randomized double-blind study in healthy humans. European Journal of Clinical Nutrition 58:462-466 (2004).
Bowen. Exocrine secretions of the pancreas. Jul. 5, 2006. Accessed online at www.vivo.colostate.edu/hbooks/pathphys/digestion/pancreas/exocrine.html.
Boyd, et al. Positively charged amino acid residues can act as topogenic determinants in membrane proteins. Proc Natl Acad Sci U S A. Dec. 1989;86(23):9446-50.
Bradstreet, et al. Detection of Measles Virus Genomic RNA in Cerebrospinal Fluid of Children with Regressive Autism: a Report of Three Cases. J. Am Phys Surg. 2004; 9(2):38-45.
Bray, et al. Effect of dietary protein content on weight gain, energy expenditure, and body composition during overeating. A randomized controlled trial. JAMA. Jan. 4, 2012; 307(1):47-55.
Brinkley, et al. Factor analysis of the aberrant behavior checklist in individuals with autism spectrum disorders. J Autism Dev Disord. Nov. 2007;37(10):1949-59. Epub Dec. 21, 2006.
Brown. Background to Parkinson's Disease. biomed.brown.edu. Jul. 14, 2008.
Brudnak et al. Enzyme-based therapy for autism spectrum disorders—is it worth another look? Med Hypoth. 2002; 58:422-428.
Brudnak, Mark et al., Guide to intestinal health in autism spectrum disorder, Kirkman Laboratories, (Oct. 2001).
Bruhat, et al. Amino acid limitation induces expression of CHOP, a CCAAT/enhancer binding protein-related gene, at both transcriptional and post-transcriptional levels. J Biol Chem. Jul. 11, 1997;272(28):17588-93.
Buie, et al. Evaluation, diagnosis, and treatment of gastrointestinal disorders in individuals with ASDs: a consensus report. Pediatrics. Jan. 2010; 125 Suppl 1:S1-18.
Button, KS et al. Power failure: why small sample size undermines the reliability of neuroscience. Nat. Rev. Neurosci. 14:365376 (2013).
Calderon-Garciduenas, et al. Immunotoxicity and environment: immunodysregulation and systemic inflammation in children. Toxicol Pathol. 2009;37(2):161-9.
Caldwell, et al. Crystalline Pancreatic Amylase. II. Improved Method for its Preparation from Hog Pancreas Glands and Additional Studies of its Properties. J. Am. Chem. Soc. 1952; 74(16):4033-4035.
Campbell et al. A genetic variant that disrupts MET transcription is associated with autism. Proc Natl Acad Sci USA. 2006; 103(45):16834-16839.
Campbell, et al. Distinct genetic risk based on association of MET in families with co- occurring autism and gastrointestinal conditions. Pediatrics. Mar. 2009; 123(3):1018-24.
Carlton. Autism and malnutrition: the milk connection. Retrieved from the internet on Feb. 18, 2008, http://www.mercola.com/2004/autism_malnutrition.htm.
Caronna, et al. Autism spectrum disorders: clinical and research frontiers. Arch Dis Child. Jun. 2008;93(6):518-23.
Carroccio et al. Effectiveness of Enteric-coated Preparations on Nutritional Parameters in Cystic Fibrosis. Digestion 41:201-206 (1988).

(56) References Cited

OTHER PUBLICATIONS

Carroccio et al. Role of pancreatic impairment in growth recovery during gluten-free diet in childhood celiac disease. Gastroenterology 112:1839-1844 (1997).
Carroccio, et al. Pancreatic enzyme therapy in childhood celiac disease. A double-blind prospective randomized study. Dig Dis Sci. Dec. 1995;40(12):2555-60.
Carroccio, et al. Secondary impairment of pancreatic function as a cause of severe malabsorption in intestinal giardiasis: a case report. Am J Trop Med Hyg. Jun. 1997;56(6):599-602.
Carroccio, et al. Secretin-cerulein test and fecal chymotrypsin concentration in children with intestinal giardiasis. Int J Pancreatol. Oct. 1993;14(2):175-80.
Cassidy, et al. A new concept for the mechanism of action of chymotrypsin: the role of the low-barrier hydrogen bond. Biochemistry. Apr. 15, 1997;36(15):4576-84.
CDC, *Escherichia coli*, Travelers Health, Chapter 3: Infectious Diseases Related to Travel, Jul. 10, 2015, Available Online at: wwwnc.cdc.gov/travel/yellowbook/2016/infectious-diseases-related-to-travel/escherichia-coli.
CDC. Attention-Deficit/Hyperactivity Disorder (ADHD). Www.cdc.org. 2005.
CDC. Autism Information Center/FAQs. Dept of Health and Human Services/CDC. Jan. 30, 2008.
CDC. High Blood Pressure. Division for Heart Disease Stroke Prevention. Jul. 15, 2003.
Chaignon et al. Susceptibility of staphylococcal biofilms to enzymatic treatments depends on their chemical compositions. Appl. Microbiol. Appl. Microbiol. 75:125-132 (2007).
Chazalette, J.P. et al., A double-bind placebo-controlled trial of a pancreatic enzyme formulation (Panzytrat 25000) in the treatment of impaired lipid digestion in patients with cystic fibrosis. Drug Invest., 5(5):274-280 (1993).
Chen, et al. Identification of two lysosomal membrane glycoproteins. J Cell Biol. Jul. 1985;101(1):85-95.
Chen, et al. Lysine 43 is trimethylated in subunit C from bovine mitochondrial ATP synthase and in storage bodies associated with batten disease. J Biol Chem. May 21, 2004;279(21):21883-7.
Chen, et al. Medicinal Functions of Bromelain and Its Application Prospect in Animal Husbandry, China Animal Husbandry & Veterinary Medicine. 2005; vol. 32, No. 1, p. 14-16. (in Chinese with English translation).
Chez, M. et al. Secretin and autism: A two-part clinical investigation. Journal of Autism and Developmental Disorders, 30(2), 87-94 (Apr. 2000) [Abstract Only].
Childhood Autism Rating Scale (CARS), Wikipedia, downloaded May 5, 2014.
Chung, et al. Effects of a central cholinesterase inhibitor on reducing falls in Parkinson disease. Neurology. Oct. 5, 2010;75(14):1263-9. Epub Sep. 1, 2010.
Cichoke, AJ The Complete Book of Enzyme Therapy, Penguin (1999) pp. 206-208 and 38.
Cichoke, et al. The complete book of enzyme therapy. Penguin. 1998: 39, 42, 47, 50, and 53.
Cichoke. Celiac disease. The complete book of enzyme therapy. Penguin. New York, NY. 1999; 174-177.
Cichoke. Influenza. In: The Complete Book of Enzyme Therapy. Anthony J. Cichoke. Avery, a member of Penguin Putnam, Inc., publisher. Ed.: Dara Stewart, pp. 37, 40-45 (1999).
Cichoke. Influenza. In: The Complete Book of Enzyme Therapy. D. Stewart, ed. Copyright 1999. Anthony J. Cichoke. Penguin Putnam, Inc., New York, New York. pp. "Contents", 50, 273-275 and 455.
Clark et al., The effect of ranitidine versus proton pump inhibitors on gastric secretions: a meta-analysis of randomized control trials, Anaesthesia, 2009, 64, pp. 652-657.
Claud, et a. Hypothesis: inappropriate colonization of the premature intestine can cause neonatal necrotizing enterocolitis. FASEB J. Jun. 2001;15(8):1398-403.
Commentary on the Japanese Pharmacopoeia, 14th ed., D929-D931, 2001.
Concerta. ADHD Myths and Facts. ADHD Myths and Facts about medication, girls, and symptoms and causes. Concerta.net. Jul. 15, 2008.
Cornish. A balanced approach towards healthy eating in autism, Journal of Human Nutrition and Dietetics 11:501-509 (1998).
Corring, et al. Development of digestive enzymes in the piglet from birth to 8 weeks. I. Pancreas and pancreatic enzymes. Nutr Metab. 1978;22(4):231-43.
Couet, et al. Identification of peptide and protein ligands for the caveolin-scaffolding domain. Implications for the interaction of caveolin with caveolae-associated proteins. J Biol Chem. Mar. 7, 1997;272(10):6525-33.
Coutinho, AM et al. Variants of the serotonin transporter gene (SLC6A4) significantly contribute to hyperserotonemia in autism. Mol Psychiatry. Mar. 2004;9(3):264-71.
Cox, RJ et al. Influenza Virus: Immunity and Vaccination Strategies. Comparison of the Immune Response to Inactivated and Live, Attenuated Influenza Vaccines. Scandinavian Journal of Immunology 59, 1-15 (2004).
COYLE. Treating the Negative Symptoms of Schizophrenia: An Expert Interview with Joseph Coyle, MD. www.narsad.org/?q=node/438/latest-research. 2006.
Craig, et al. Heat shock proteins: molecular chaperones of protein biogenesis. Microbiol Rev. Jun. 1993;57(2):402-14.
Creon—FDA Prescribing information side effects and uses. Revised Apr. 2015.
Creon digestive enzymes. Celic.com/ Jun. 2009. http://www.celiac.com/gluten-free/topic/59195-creon-digestive-enzymes.
Creon. Full prescribing information. Last edited Mar. 2013. Abbvie Inc 2012. www.rxabbvie.com/pdf/creon_Pl.pdf.
Croonenberghs, et al. Peripheral markers of serotonergic and noradrenergic function in post-pubertal, Caucasian males with autistic disorder. Neuropsychopharmacology. Mar. 2000;22(3):275-83.
Cruse et al. Illustrated dictionary of immunology. CRC Press, New York. 1995.
Cuervo, et al. Cathepsin A regulates chaperone-mediated autophagy through cleavage of the lysosomal receptor. EMBO J. Jan. 2, 2003;22(1):47-59.
Curemark press release. Curemark Receives Investigational New Drug Clearance for CM-AT for Autism. Mar. 26, 2009. http://www.medicalnewstoday.com/releases/143723.php.
Curemark Trademark/Service mark application, Principal Register. Serial No. 77527223. Filing date: Jul. 21, 2008.
Dajcs, et al. Lysostaphin is effective in treating methicillin-resistant *Staphylococcus aureus* Endophthalmitisin the rabbit. Curr Eye Res. Jun. 2001;22(6):451-7.
Daly, E., et al. Response inhibition and serotonin in autism: A functional MRI study using acute tryptophan depletion. Brain, 137(9), 2600-2610 (Sep. 2014).
Darman. An introduction to alternative medicine for psychiatric conditions. Oct. 22, 2007, retrieved on Sep. 18, 2009, http://web.archive.org/web/20071022104238/http://altp[therapies4bipolar.info/ortho/html.
Dawe, et al. Antipsychotic drugs dose-dependently suppress the spontaneous hyperactivity of the chakragati mouse. Neuroscience. Nov. 24, 2010;171(1):162-72. Epub Sep. 17, 2010.
Dawe, et al. The chakragati mouse: a mouse model for rapid in vivo screening of antipsychotic drug candidates. Biotechnol J. Nov. 2007;2(11):1344-52.
Dawn. Autism: the Latest Prevalence Rates in USA—Now 1 in 175. Disabled Women's Network Ontario. Dawn.thot.net/autism2.html. 2006.
Dawson lab. Research Projects in Synthetic Protein Chemistry. 2005; 1-2.
Delong. News on Parkinson's. The Dana Foundation. Jul. 14, 2008.
Derwent. English abstract for RU 2286785 Nov. 10, 2006. Downloaded from the Derwent file Jul. 13, 2011.
Diagnostic and Statistical Manual of Mental Disorders, Fourth Edition, Primary Care Version, Chapter 6, American Psychiatric Association (2000).
Diagnostic and Statistical Manual of Mental Disorders, Fourth Edition, Text Revision, DSM-IV-TR, American Psychiatric Association (2000).

(56) References Cited

OTHER PUBLICATIONS

Diaz-Hernandez, et al. Neuronal induction of the immunoproteasome in Huntington's disease. J Neurosci. Dec. 17, 2003;23(37):11653-61.
Digestive Enzyme Preparation: Pancreatin listed in Japanese Pharmacopoeia, Aug. 2008,<URL:http:>(in Japanese with English translation)</URL:http:>.
Digestive Enzyme Wikipedia. Retrieved from the internet Sep. 10, 2009, http://en.wikipedia.org/wiki/Digestive_enzyme.
Ding, et al. Proteasome inhibition in oxidative stress neurotoxicity: implications for heat shock proteins. J Neurochem. May 2001;77(4):1010-7.
Dobbs et al. Link between helicobacter pylori infection and idiopathic parkinsonism. Medical Hypothesis. 2000; 55(2):93-98.
Dockter et al. Determination of chymotrypsin in the feces by a new photometric method. Padiatr Padol. 1985; 20(3):257-265.
Dominquez-Munoz, et al. Optimising the therapy of exocrine pancreatic insufficiency by the association of a proton pump inhibitor to enteric coated pancreatic extracts. Gut. Jul. 2006;55(7):1056-7.
Drabkin, H., et al. Initiation of protein synthesis in mammalian cells with codons other than AUG and amino acids other than methionine. Molecular and Cellular Biology, 18(9): 5140-5147 (Sep. 1998).
Dudzinska. Dissertation. Development of lipid-based enteric coatings. Oct. 18, 1988. Martin Luther University, Halle-Wittenberg. pp. 1-125.
Dupiereux, et al. Creutzfeldt-Jakob, Parkinson, lewy body dementia and Alzheimer diseases: from diagnosis to therapy. Cent Nerv Syst Agents Med Chem. Mar. 2009;9(1):2-11.
Durie et al. Uses and abuses of enzyme therapy in cystic fibrosis. Journal of the Royal Society of Medicine. 91:(Suppl. 34):2-13 (1998).
Durkin, et al. Socioeconomic inequality in the prevalence of autism spectrum disorder: evidence from a U.S. cross-sectional study. PLoS One. Jul. 12, 2010;5(7):e11551.
Eaves, et al. The criterion-related validity of the Childhood Autism Rating Scale and the Autism Behavior Checklist. J Abnorm Child Psychol. Oct. 1993;21(5):481-91. abstract only.
Edelson, et al. 3-Cyclohexene-1-glycine, an Isoleucine Antagonist. J. Am. Chem. Soc. 1958; 80(11):2698-2700.
Elkashef, et al. Biological markers of cocaine addiction: implications for medications development. Addict Biol. Jun. 2003;8(2):123-39.
Elphick, et al. Impaired luminal processing of human defensin-5 in Crohn's disease: persistence in a complex with chymotrypsinogen and trypsin. Am J Pathol. Mar. 2008;172(3):702-13.
Emc, Creon 10000 Capsules, May 18, 2015, Available Online at: www.medicines.org.uk/emc/medicine/2068.
eMedExpert, Antibiotics: Cephalosporins, Available online at: http://www.emedexpert.com/compare/ cephalosporins.shtml, available as early as Jun. 2, 2007 per Internet Archive Wayback Machine.
Ethridge, et al. Acute pancreatitis results in induction of heat shock proteins 70 and 27 and heat shock factor-1. Pancreas. Oct. 2000;21(3):248-56.
Evans, C. et al. Altered amino acid excretion in children with autism. Nutritional Neuroscience, 11(1):9-17 (Feb. 2008).
Evans, et al. Pancreatic insufficiency in adult celiac disease: do patients require long-term enzyme supplementation? Dig Dis Sci. Oct. 2010;55(10):2999-3004. doi: 10.1007/s10620-010-1261-y. Epub May 11, 2010.
Exocrine Pancreatic Insufficiency (Enzymes) Document downloaded online on Jan. 8, 2016 at: http://www.epi4dogs.com/enzyme.htm< http:></http:>.
Fafournoux, P. et al. Amino acid regulation of gene expression. Biochemical Journal, 351:1-12(2000).
Fairclough, P. et al. Comparison of the absorption of two protein hydrolysates and their effects on water and electrolyte movements in the human jejunum. Gut, 21(10):829-834 (1980).
Fallingborg, et al. Measurement of gastrointestinal pH and regional transit times in normal children. J Pediatr Gastroenterol Nutr. Aug. 1990;11(2):211-4.
Fallon. Could one of the most widely prescribed antibiotics amoxicillin/clavulanate "augmentin" be a risk factor for autism? Med Hypotheses. 2005;64(2):312-5.
Family Caregiver Alliance. Fact Sheet: Parkinson's Disease. Caregiver. org. Jul. 14, 2008.
Felig, P. Amino acid metabolism in man. Annual Review of Biochemistry, 44(1):933-955 (1975). [Abstract Only].
Fernell, et al. No evidence for a clear link between active intestinal inflammation and autism based on analyses of faecal calprotectin and rectal nitric oxide. Acta Paediatr. Jul. 2007;96(7):1076-9.
Ferrone, et al. Pancreatic enzyme pharmacotherapy. Pharmacotherapy. 2007; 27:910-920.
Fido, et al. Olanzapine in the treatment of behavioral problems associated with autism: an open-label trial in Kuwait. Med Princ Pract. 2008; 17(5):415-8. doi: 10.1159/000141508. Epub Aug. 6, 2008.
Filipek et al. The screening and diagnosis of autistic spectrum disorders. J. of Autism and Dev Disorders. 1999; 29(6).
Final Office Action dated Jan. 3, 2012 for U.S. Appl. No. 10/681,018.
Final Office Action dated Jan. 26, 2012 for U.S. Appl. No. 12/487,864.
Final Office Action dated Nov. 8, 2011 for U.S. Appl. No. 12/054,343.
Final Office Action dated Nov. 8, 2011 for U.S. Appl. No. 12/786,739.
Final Office Action dated Nov. 9, 2010 for U.S. Appl. No. 09/990,909.
Final Office Action dated Feb. 14, 2011 for U.S. Appl. No. 12/049,613.
Final Office Action dated Feb. 27, 2009 for U.S. Appl. No. 11/555,697.
Final Office Action dated Mar. 13, 2009 for U.S. Appl. No. 11/232,180.
Final Office Action dated Mar. 17, 08 for U.S. Appl. No. 10/681,018.
Final Office Action dated Apr. 28, 09 for U.S. Appl. No. 10/681,018.
Final Office Action dated May 11, 10 for U.S. Appl. No. 11/555,697.
Final Office Action dated Jun. 25, 08 for U.S. Appl. No. 11/213,255.
Final Office Action dated Jul. 2, 10 for U.S. Appl. No. 12/046,252.
Final Office Action dated Jul. 27, 04 for U.S. Appl. No. 09/990,909.
Finegold et al. Gastrointestinal microflora studies in late-onset autism. Clinical Infectious Diseases. 2002; 35(1):S6-S15.
First, M. Structured clinical interview for DSM-IV-TR axis I disorders, research version, patient edition. (SCID-I/P) New York: Biometrics Research, New York State Psychiatric Institute. (2002).
Fitzsimmons, et al. High-dose pancreatic-enzyme supplements and fibrosing colonopathy in children with cystic fibrosis. N Engl J Med. May 1, 1997;336(18):1283-9.
Flament, M.P. et al. Development of 400 um Pellets by Extrusion-Spheronization Application with Gelucire 50/02 to Produce a "Sprinkle" Form, Drug Development and industrial Pharmacy, 30:1, 43-51, DOI: 10.1081/DDC-120027510 (2004).
Fliri, et al. Drug effects viewed from a signal transduction network perspective. J Med Chem. Dec. 24, 2009;52(24):8038-46. doi: 10.1021/jm901001p.
Frossard, et al. Both thermal and non-thermal stress protect against caerulein induced pancreatitis and prevent trypsinogen activation in the pancreas. Gut. Jan. 2002;50(1):78-83.
Frossard. Trypsin activation peptide (TAP) in acute pancreatitis: from pathophysiology to clinical usefulness. JOP. Mar. 2001;2(2):69-77.
Furlano, et al. Colonic CD8 and gamma delta T-cell infiltration with epithelial damage in children with autism. J Pediatr. Mar. 2001;138(3):366-72.
Garcia et al. Detection of Giardia lamblia, Entamoeba histolytica/Entamoeba dispar, and Cryptosporidium parvum antigens in human fecal specimens using the triage parasite panel enzyme immunoassay. Am Soc for Microbiology. 2000; 38(9):3337-3340.
Gardner. Absorption of intact peptides: studies on transport of protein digests and dipeptides across rat small intestine in vitro. Q J Exp Physiol. Oct. 1982;67(4):629-37.
Garner Jr, et al. Porcine Pancreatic Lipase—A Glycoprotein. J Biol Chem. Jan. 25, 1972;247(2):561-5.
Gass, et al. Enhancement of dietary protein digestion by conjugated bile acids. Gastroenterology. Jul. 2007;133(1):16-23.
Generation Rescue. Autism and Vaccines Around the World: Vaccine Schedules, Autism Rates, and Under 5 Mortality. Apr. 1, 2009.

(56) References Cited

OTHER PUBLICATIONS

German, et al., Apple iPhone Review: Apple iPhone, Jun. 30, 2007; CINET.
Giglio, et al. Failure to thrive: the earliest feature of cystic fibrosis in infants diagnosed by neonatal screening. Acta Paediatr. Nov. 1997;86(11):1162-5.
GM Chemie 2010 "Products: Hypromellose Phthalate" accessed from www.gmchemie.com on Sep. 22, 2014.
Goff, et al. Production of abnormal proteins in E. coli stimulates transcription of lon and other heat shock genes. Cell. Jun. 1985;41(2):587-95.
Gonzalez, et al. Endoscopical, histological and immunological characteristics of the digestive mucosa in autistic children with gastrointestinal symptoms. 2005; 1-7.
Green, et al. Amino-terminal polymorphisms of the human beta 2-adrenergic receptor impart distinct agonist-promoted regulatory properties. Biochemistry. Aug. 16, 1994;33(32):9414-9.
Guesnet, P. et al. Docosahexaenoic acid (DHA) and the developing central nervous system (CNS)—Implications for dietary recommendations. Biochimie, 93(1):7-12(2011). [Abstract Only].
Gupta, et al. Analysis of data gaps pertaining to enterotoxigenic *Escherichia coli* in low and medium human development index countries, 1984-2005. Epidemiol Infect. 2008; 136:721-738.
Gupta, et al. Th1- and Th2-like cytokines in CD4+ and CD8+ T cells in autism. J Neuroimmunol. May 1, 1998;85(1):106-9.
Hadjivassiliou, et al. Does cryptic gluten sensitivity play a part in neurological illness? Lancet. Feb. 10, 1996;347(8998):369-71.
Hamel, E. et al. Effects of Cocaine on Rat Pancreatic Enzyme Secretion and Protein Synthesis, Digestive Diseases, 23(3):264-268 (Mar. 1978).
Happe et al. The neuropsychology of autism. Brain. 1996; 119:1377-1400.
Happe et al. Time to give up on a simple explanation for autism. Nat Neurosci. Oct. 2006; 9(10):1218-20.
HEALTH.com. Who is affected by Parkinson's disease. www.health.com. Jul. 14, 2008.
Heijerman, et al. Omeprazole enhances the efficacy of pancreatin (pancrease) in cystic fibrosis. Ann Intern Med. Feb. 1, 1991;114(3):200-1.
Heil, M., et al. Low endogenous fecal chymotrypsin: a possible biomarker for autism. Poster presented at the annual IMFAR Conference on Autism, Atlanta, GA.(May 2014) p. 1.
Hendren et al. Mechanistic biomarkers for autism treatment. Medical Hypotheses. 2009; 73:950-954.
Hitti. Allergy, celiac disease, and ileal lymphonodular. WebMD. 2005. 1-2.
Holquist et al. FDA safety page: Delayed-release vs. extended release Rxs. Drug Topics [online] Jul. 23, 2007 [Retrieved on Jul. 30, 2012] Retrieved from the internet: http://drugtopics.modernmedicine.com/drugtopics/Top+News/FDA-safety-page-Delayed-release-vs-extended-release/ArticleStandard/Article/detail/442606.
Holten, et al. Appropriate prescribing of oral beta-lactam antibiotics. Am Fam Physician. Aug. 1, 2000;62(3):611-20.
Horvath et al. Improved social and language skills after secretin administration in patients with autistic spectrum disorders. Journal of the Association for Academic Minority Physicians. Jan. 1998; 9(1):9-15.
Horvath, et al. Autism and gastrointestinal symptoms. Curr Gastroenterol Rep. Jun. 2002;4(3):251-8.
Horvath, et al. Autistic disorder and gastrointestinal disease. Curr Opin Pediatr. Oct. 2002; 14(5):583-7.
Horvath, et al. Gastrointestinal abnormalities in children with autistic disorder. J Pediatr. Nov. 1999;135(5):559-63.
Hoshiko et al. The effect of the gastrointestinal hormones on colonic muscosal blood flow. Acta Medica Nagasakiensia. 1994; 39(4):125-130.
Houston. Autism—One Conference. May 2006. 1-83.
Hsiao, et al. The microbes of the intestine: an introduction to their metabolic and signaling capabilities. Endocrinol Metab Clin North Am. Dec. 2008;37(4):857-71.
Huang, et al. Apoptotic cell death in mouse models of GM2 gangliosidosis and observations on human Tay-Sachs and Sandhoff diseases. Hum Mol Genet. Oct. 1997;6(11):1879-85.
Huang, et al. Mapping of the human APOB gene to chromosome 2p and demonstration of a two-allele restriction fragment length polymorphism. Proc Natl Acad Sci U S A. Feb. 1986;83(3):644-8.
Ijuin, H. Evaluation of pancreatic exocrine function and zinc absorption in alcoholism. The Kurume Medical Journal 45.1 (1998): 1-5.
Information of Papain from Worthington Enzymes webpage http://www.worthington-biochem.com/pap/default.html Downloaded Jan. 17, 2013.
International Application No. PCT/US18/26841 International Search Report and Written Opinion Mailed Jul. 3, 2018.
International preliminary report on patentability dated Jul. 17, 2014 for PCT/US2013/020183.
International Preliminary Report on Patentability dated Oct. 15, 2019 for PCT/US2018/026841.
International search report and written opinion dated Feb. 21, 2013 for PCT/US2013/020183.
International search report and written opinion dated May 9, 2013 for PCT/US2013/024453.
International search report and written opinion dated Aug. 27, 2013 for PCT/US2013/043444.
International search report and written opinion dated Jan. 18, 2011 for PCT/US2010/057341.
International search report and written opinion dated Nov. 12, 2012 for PCT/US2012/034489.
International search report and written opinion dated Feb. 15, 2011 for PCT/US2010/053484.
International search report and written opinion dated Mar. 2, 2010 for PCT/US2010/020253.
International search report and written opinion dated Mar. 5, 2010 for PCT/US2010/020259.
International search report and written opinion dated Jun. 9, 2010 for PCT/US2010/030895.
International search report and written opinion dated Sep. 25, 2009 for PCT/US2009/049374.
International search report dated Mar. 11, 2002 for PCT/US2001/25343.
International search report dated Jun. 29, 2001 for PCT/US2000/34000.
Isaksson, et al. Pain reduction by an oral pancreatic enzyme preparation in chronic pancreatitis. Digestive Dis. Sci. 1983; 28(2):97-102.
James, et al. Thimerosal neurotoxicity is associated with glutathione depletion: protection with glutathione precursors. Neurotoxicology. 2004; 26(1):1-8.
Jeffrey. Global burden of hypertension may reach 1.5 billion by 2025. Medscape Medical News. Jul. 14, 2008.
Jenkins, et al. Management of gastroenteritis. Archives of Disease in Childhood. 1990; 65:939-941.
Johnson et al. Eating Habits and Dietary Status in Young Children with Autism. J Dev Phys Disabil 20:437-448 (2008).
Juhl. Fibromyalgia and the serotonin pathway. Altern Med Rev. 1998; 3(5):367-375.
Jyonouchi, et al. Dysregulated innate immune responses in young children with autism spectrum disorders: their relationship to gastrointestinal symptoms and dietary intervention. Neuropsychobiology. 2005;51(2):77-85.
Jyonouchi, et al. Evaluation of an association between gastrointestinal symptoms and cytokine production against common dietary proteins in children with autism spectrum disorders. J Pediatr. May 2005; 146(5):605-10.
Jyonouchi, et al. Proinflammatory and regulatory cytokine production associated with innate and adaptive immune responses in children with autism spectrum disorders and developmental regression. J Neuroimmunol. Nov. 1, 2001;120(1-2):170-9.
Kachrimanis, et al. Tensile strength and disintegration of tableted silicified microcrystalline cellulose: influences of interparticle bonding. J Pharm Sci. Jul. 2003; 92(7):1489-501.

(56) References Cited

OTHER PUBLICATIONS

Kaemmerer, et al. Effects of lipid peroxidation-related protein modifications on RPE lysosomal functions and POS phagocytosis. Invest Ophthalmol Vis Sci. Mar. 2007;48(3):1342-7.
Kaminski, et al. Polymorphism of bovine beta-casein and its potential effect on human health. J Appl Genet. 2007;48(3):189-98.
Kaspar et al. New photometric assay for chymotrypsin in stool. Clinical Chemistry. 1984;30(11):1753-1757.
Katritos. New finding may have implications for schizophrenia, autism. Autism/Schizophrenia findings relating to protein, etc. Feb. 10, 2011. e-mail.
Kearney, et al. Global burden of hypertension: analysis of worldwide data. Lancet. Jan. 15-21, 2005;365(9455):217-23. Abstract only.
Keeley et al., Gradual vs. abrupt withdrawal of methylphenidate in two older dependent males. Journal of Substance Abuse Treatment. 2(2):123-125 (1985).
Keller, et al. Pancreatic enzyme supplementation therapy. Current Treatment Options in Gastroenterology 6.5 (2003): 369-374.
Kidd, P.M., Autism, an extreme challenge to integrative medicine. Part 2: medical management. Altern. Med. Rev., 7(6):172-499 (Dec. 2002).
King, et al. Effects of bacterial microflora of the lower digestive tract of free-range waterfowl on influenza virus activation. Appl Environ Microbiol. Jun. 2011;77(12):4119-25. doi: 10.1128/AEM.02578-10. Epub Apr. 29, 2011.
Klopfleisch et al. Encephalitis in a stone marten (Martes foina) after natural infection with highly pathogenic avian influenza virus subtype H5N1. Journal of Comparative Pathology 137:155-159 (2007).
Knivsberg, et al. A randomised, controlled study of dietary intervention in autistic syndromes. Nutr Neurosci. Sep. 2002;5(4):251-61.
Koh et al. Inflammation and wound healing: The role of the macrophage. Expert Rev Mol Med. 13:e23 (Author manuscript).
Koivu et al. Determination of Phylloquinone in Vegetables, Fruits, and Berries by High-Performance Liquid Chromatography with Electrochemical Detection. J. Agric. Food Chem. 45(12):4644-4649 (1997).
Kokai-Kun, et al. Lysostaphin as a treatment for systemic Staphylococcus aureus infection in a mouse model. J Antimicrob Chemother. Nov. 2007;60(5):1051-9. Epub Sep. 10, 2007.
Koller, et al. Falls and Parkinson's Disease (Abstract). Clin Neuropharmacol. 1989; 12(2):98-105.
Koplin, et al. Soy consumption is not a risk factor for peanut sensitization. J Allergy Clin Immunol. Jun. 2008;121(6):1455-9.
Koster et al. Evidence based medicine and extradigestive manifestations of helicobacter pylori. Acta Gastro-Enterologica Belgica. 2000; 63(4):388-392.
Krishnaswami, et al. A systematic review of secretin for children with autism spectrum disorders. Pediatrics. May 2011;127(5):e1322-5. doi: 10.1542/peds.2011-0428. Epub Apr. 4, 2011.
Kronenberg, et al. Folate deficiency induces neurodegeneration and brain dysfunction in mice lacking uracil DNA glycosylase. J Neurosci. Jul. 9, 2008;28(28):7219-30.
Kujoth, et al. Mitochondrial DNA mutations, oxidative stress, and apoptosis in mammalian aging. Science. Jul. 15, 2005;309(5733):481-4.
Kumar. Neurologic presentations of nutritional deficiencies. Neurol Clin. Feb. 2010;28(1):107-70.
Larimore. How Common Is ADHD? Facts About ADHD. Jul. 15, 2008.
Lashkari, et al. Williams-Beuren Syndrome: An update and review for the primary physician. Clinical Pediatrics. 1999; 38(4):189-208.
Layer et al. Pancreatic enzyme replacement therapy. Current Gastroenterology Reports. 2001; 3:101-108.
Lebenthal, et al. Enzyme therapy for pancreatic insufficiency: present status and future needs. Pancreas. Jan. 1994;9(1):1-12.
Leeds, et al. Is exocrine pancreatic insufficiency in adult coeliac disease a cause of persisting symptoms? Aliment Pharmacol Ther. Feb. 1, 2007;25(3):265-71.
Levy, et al. Relationship of dietary intake to gastrointestinal symptoms in children with autistic spectrum disorders. Biol Psychiatry. Feb. 15, 2007;61(4):492-7.
Leyfer, et al. Comorbid psychiatric disorders in children with autism: interview development and rates of disorders. J Autism Dev Disord. Oct. 2006;36(7):849-61.
Lieberman. Pharmaceutical Dosage Forms. vol. 2: Disperse Systems. New York Marcel Dekker, Inc. 1996; 243-258.
Life Plus Somazyne accessed Jun. 10, 2016, Online at www.lifeplus.com/media/pdf/piSheets/US/ 6141-PI_EN.pdf.
Lipase 30, Technical Data sheet, 1 page, Scientific Protein Laboratories LLC Jun. 13, 2005.
Liyanage, et al. Bioavailability of iron from micro-encapsulated iron sprinkle supplement. Food and Nutrition bulletin. 2002; 23(3):133-137.
Lloyd. Lysosome membrane permeability: implications for drug delivery. Adv Drug Deliv Rev. Mar. 30, 2000;41(2):189-200.
Lockner et al. Dietary intake and parents' perception of mealtime behaviors in preschool-age children with autism spectrum disorder and in typically developing children. J Am Diet Assoc 108(8):1360-1363 (2008).
Loh, et al. Highly tolerated amino acid substitutions increase the fidelity of Escherichia coli DNA polymerase I. J Biol Chem. Apr. 20, 2007;282(16):12201-9.
Lord, et al. Diagnostic Instruments in Autistic Spectrum Disorders. info.med.yale.edu. 2005; 11:730-771.
Luedtke, et al. Cathepsin A is expressed in a cell- and region-specific manner in the testis and epididymis and is not regulated by testicular or pituitary factors. J Histochem Cytochem. Aug. 2000;48(8):1131-46.
MacDonald. Thyrotoxicosis treated with pancreatic extract and iodine. Lancet. 1943; 244(6251):788.
Macfabe, et al. Neurobiological effects of intraventricular propionic acid in rats: possible role of short chain fatty acids on the pathogenesis and characteristics of autism spectrum disorders. Behav Brain Res. 2006;176(1):149-69.
Macready. Parkinson's Disease Treatment: what you should know. Retrieved from the internet on Sep. 15, 2009, http://www.everydayhealth.com/parkinsons-disease-treatment-overview.aspx.
Mannino, et al. Surveillance for asthma—United States, 1960-1995. Mmwr Cdc Surveill Summ. Apr. 24, 1998;47(1):1-27.
Marcus, et al. A placebo-controlled, fixed-dose study of aripiprazole in children and adolescents with irritability associated with autistic disorder. J Am Acad Child Adolesc Psychiatry. Nov. 2009;48(11):1110-19.
Marczewska et al. Protein intake in parkinsonian using the EPIC food frequency questionnaire. Mov Diord. Aug. 2006; 21(8):1229-1231.
Marion et al., A New Procedure Allowing the Complete Removal and Prevention of Hemodialysis. Blood Purification, 23:339-348 (2005).
Marlicz et al. Determination of chymotrypsin in the stool in the diagnosis of chronic pancreatitis. Wiadomosci lekarskie. 1988; 41(11):704-707. (in Polish with English abstract/summary).
Marsh. Neuropsychiatric aspects of Parkinson's disease. Psychosomatics. 2000; 41(1):15-23.
Martin, et al. A rapid and sensitive spectrophotometric method for the assay of chymotrypsin. Biol Chem. Feb. 1959;234(2):294-8.
Matikainen, et al. Autonomic dysfunction in long-standing alcoholism. Alcohol. 1986;21(1):69-73. Abstract only.
Matthews, D. Intestinal absorption of amino acids and peptides. Proceedings of the Nutrition Society, 31(2):171-177(1972).
Maurin, et al. Cellular adaptation to amino acid availability: mechanisms involved in the regulation of gene expression. 2006; 319-326.
Mayo Clinic Staff. Autism. Retrieved from internet Mar. 10, 2008, http://www.mayoclinic.com/health/autism/DS00348DSECTION=2.
Mayo Clinic Staff. Bipolar disorder. Jan. 4, 2008, http://www.mayoclinic.com/health/bipolardisorder/DS00356/DSECTION=symptoms.

(56) References Cited

OTHER PUBLICATIONS

Mayo Clinic Staff. Obsessive-compulsive disorder. Dec. 21, 2006. http://www.preferredalternatives.org/lat/WellnessLibrary/anxiety&PanicDisorders/Obsessive-CompulsiveDisorder/Obsessive-CompulsiveDisorder-Mayoclinic.pdf.
Mayo Clinic Staff. Oppositional defiant disorder. Dec. 19, 2007, http://www.mayoclinic.com/health/oppositional-defiant-disorder/DS00630/DSECTION=symptoms.
Mcalonan, et al. Brain anatomy and sensorimotor gating in Asperger's syndrome. ain. Jul. 2002; 125(Pt 7):1594-606.
McClung, C., et al. Regulation of gene expression and cocaine reward by CREB and DeltaFosB. Nature Neuroscience, 6(11):1208-1215 (2003). [Abstract Only].
McClung, C.A et al. DeltaFosB: A molecular switch for long-term adaptation in the brain. Molecular Brain Research, 132(2):146-154 (Dec. 20, 2004).
McCormack, et al. Localization of the disulfide bond involved in post-translational processing of glycosylasparaginase and disrupted by a mutation in the Finnish-type aspartylglycosaminuria. J Biol Chem. Feb. 17, 1995;270(7):3212-5.
McCracken, et al. Risperidone in children with autism and serious behavioral problems. N Engl J Med. Aug. 1, 2002;347(5):314-21.
Medori et al. Fatal Familial Insomnia, A Prion Disease With a Mutation at Condon 178 of The Prion Protein Case. N Engl J Med 326:444-449 (1992).
Medsafe. Data sheet for alpha-lactose, Jul. 21, 2008, http://www.medsafe.govt.nz/Profs/Datasheet/a/Alphalactulosesyrup.htm.
Medscape. Burden of Hypertension in the United States Greater Than Ever. www.medscape.com. Jul. 14, 2004.
Melmed, et al. Metabolic markers and gastrointestinal symptoms in children with autism and related disorders. J Pediatr Gast Nutr. 2000; 31:S31-S32. Abstract only.
Merck. Autism, Merck manual online medical library home addition, retrieved from the internet Mar. 10, 2008, http://www.mercl.com/mmhge/sec23/ch286/ch286b.html.
Merriam-Webster 2014 "Definition: Precipitate" accessed from www.mirriam-webster.com on Sep. 22, 2014.
MeSH browser. "Child Development Disorders, Pervasive," and "Attention Deficit and Disruptive Behavior Disorders," National Library of medicine. 2001, http://www.nlm.nih.gov/mesh/2002/Mbrowser.html.
Meyer-Lindenberg, et al. Neural mechanisms in Williams syndrome: a unique window to genetic influences on cognition and behavior. Nat. Rev. Neurosci. 2006; 7(5):380-93.
Michael's Naturopathic Programs, Digestive Enzymes, Product #011161, Accessed on Jun. 10, 2016, online at: www.michaelshealth.com/retail/digestive-enzymes-659.html.
Michell et al. Biomarkers and Parkinson's disease. Brain. 2004; 127(8):1693-1705.
Millipore EMD catalog (online). Papain, unit definition, EMD Millipore Corp, 2013. Downloaded May 13, 2013.
Minamino, et al. Vascular cell senescence: contribution to atherosclerosis. Circ Res. Jan. 5, 2007;100(1):15-26.
Ming, et al. Autism spectrum disorders: concurrent clinical disorders. J Child Neurol. Jan. 2008;23(1):6-13.
Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.
Mitsui, et al. Role of aminopeptidases in the blood pressure regulation. Biological and Pharmaceutical Bulletin of Japan, Pharmaceutical Society of Japan. 2004; 27(6):768-771.
Mizutani, et al. Effects of placental proteases on maternal and fetal blood pressure in normal pregnancy and preeclampsia. Am J Hypertens. Jun. 1996;9(6):591-7.
Mononen, et al. Aspartylglycosaminuria in the Finnish population: identification of two point mutations in the heavy chain of glycoasparaginase. Proc Natl Acad Sci U S A. Apr. 1, 1991;88(7):2941-5.
Moretti, et al. Acute pancreatitis: hypertonic saline increases heat shock proteins 70 and 90 and reduces neutrophil infiltration in lung injury. Pancreas. Jul. 2009;38(5):507-14. Abstract only.
Morimoto, R. The heat shock response: Systems biology of proteotoxic stress in aging and disease. Cold Spring Harbor Symposia on Quantitative Biology, 76:91-99 (2011) (Epub: Feb. 27, 2012).
Mosqueira, et al. Chronic hypoxia impairs muscle function in the Drosophila model of Duchenne's muscular dystrophy (Dmd). PLoS One. Oct. 20, 2010;5(10):e13450.
Munasinghe et al. Digestive enzyme supplementation for autism spectrum disorders: a double-blind randomized controlled trial. J Autism Dev Disord. Sep. 2010;40(9):1131-8.
Munesue, et al. High prevalence of bipolar disorder comorbidity in adolescents and young adults with high-functioning autism spectrum disorder: a preliminary study of 44 outpatients. Journal of Affective Disorders 111.2-3 (2008): 170-175.
Nachaegari et al. Coprocessed excipients for solid dosage forms. Pharmaceutical Technology. 2004; p. 52, 54, 56 ,58, 60, 64.
Nagamoto. Jacobson: Psychiatric Secrets, 2nd ed. 2001. Ch 28 Antipsychotic meds.
Naushad, Shaik Mohammad et al. Autistic children exhibit distinct plasma amino acid profile. Indian Journal of Biochemistry and Biophysics, 50(5):474-478 (Oct. 2013).
Naver.com entry for Rare Disease Information: Osteopenia—Osteopsathyrosis, Fragilitasossium, Fragilitasossium (accessed Sep. 25, 2019).
Nestler, E.J. Molecular basis of long-term plasticity underlying addiction. Nature Reviews Neuroscience, 2(2):119-128 (Feb. 2001).
Nestler, et al. Delta-FosB: A sustained molecular switch for addiction. PNAS 98(20): 11042-11046 (Sep. 25, 2001).
Neuer, et al. The role of heat shock proteins in reproduction. Hum Reprod Update. Mar.-Apr. 2000;6(2):149-59.
Neumeyer, Ann. M. et al. Brief Report: Bone Fractures in Children and Adults with Autism Spectrum Disorders. J. Autism Dev. Disord. 45(3):881-887 (Mar. 2016).
Nevo et al. Acute immune polyneuropathies: correlations of serum antibodies to Campylobacter jejuni and Helicobacter pylori with anti-gm antibodies and clinical patterns of disease. J of Inf Diseases. 1997; 175(S2):S154-6.
Newhorizons. ADD/ADHD: New Perspectives on Attentional Priority Disorders. New Horizons for Learning. Jul. 15, 2008.
NIH, "Celiac Disease", National Digestive Diseases Information Clearinghouse: Bethesda, MD, 2008; 12 pages.
NIH. National Institutes of Health. National Diabetes Statistics 2007. diabetes.niddk.nih.gov. Jun. 1, 2008.
NINDS Guillain-Barre Syndrome Information Page, retrieved from the internet Sep. 15, 2009, http://www.ninds.nih.gov/disorders/gbs/gbs.htm.
NINDS DysautonomiaInformation Page, retrieved from the internet Sep. 10, 2009, http://www.ninds.nih.gov/disorders/dysautonomia/dysautonomia.htm.
No Author. RSDSA, 2015: Telltale signs and symptoms of CRPS/RSD on the web at rsds.org/telltale-signs-and-symptoms-of-crpsrsd. [Accessed: Sep. 5, 2018].
Norton, L. et al. Leucine regulates translation initiation of protein synthesis in skeletal muscle after exercise. The Journal of Nutrition, 136(2):533S-537S (Feb. 2006).
Notice of allowance dated Jan. 2, 2014 for U.S. Appl. No. 13/204,881.
Notice of allowance dated Feb. 2, 2015 for U.S. Appl. No. 13/926,822.
Notice of Allowance dated Feb. 17, 12 for U.S. Appl. No. 10/681,018.
Notice of allowance dated Feb. 20, 2015 for U.S. Appl. No. 12/386,051.
Notice of allowance dated Feb. 27, 2015 for U.S. Appl. No. 14/037,696.
Notice of allowance dated Mar. 1, 2016 for U.S. Appl. No. 14/087,930.
Notice of Allowance dated Mar. 21, 2012 for U.S. Appl. No. 12/487,864.
Notice of allowance dated Apr. 3, 2015 for U.S. Appl. No. 13/737,225.
Notice of allowance dated Apr. 10, 2015 for U.S. Appl. No. 13/144,290.
Notice of allowance dated Apr. 14, 2015 for U.S. Appl. No. 13/144,286.

(56) References Cited

OTHER PUBLICATIONS

Notice of Allowance dated Apr. 15, 2011 for U.S. Appl. No. 12/487,868.
Notice of allowance dated Apr. 22, 2016 for U.S. Appl. No. 14/528,715.
Notice of Allowance dated Apr. 29, 2011 for U.S. Appl. No. 12/046,402.
Notice of Allowance dated May 23, 2011 for U.S. Appl. No. 09/990,909.
Notice of Allowance dated May 29, 2013 for U.S. Appl. No. 13/481,087.
Notice of allowance dated Jun. 12, 2014 for U.S. Appl. No. 13/448,061.
Notice of Allowance dated Jun. 27, 2011 for U.S. Appl. No. 12/238,415.
Notice of Allowance dated Jun. 28, 2011 for U.S. Appl. No. 12/487,868.
Notice of Allowance dated Jun. 30, 2011 for U.S. Appl. No. 09/990,909.
Notice of Allowance dated Jul. 3, 2012 for U.S. Appl. No. 13/271,783.
Notice of Allowance dated Jul. 8, 2011 for U.S. Appl. No. 12/046,402.
Notice of Allowance dated Aug. 8, 2011 for U.S. Appl. No. 12/426,794.
Notice of allowance dated Aug. 11, 2014 for U.S. Appl. No. 13/193,346.
Notice of allowance dated Aug. 19, 2013 for U.S. Appl. No. 13/208,963.
Notice of allowance dated Aug. 30, 2013 for U.S. Appl. No. 12/047,818.
Notice of allowance dated Sep. 9, 2015 for U.S. Appl. No. 13/193,346.
Notice of allowance dated Sep. 15, 2014 for U.S. Appl. No. 14/037,652.
Notice of Allowance dated Sep. 20, 2011 for U.S. Appl. No. 12/283,090.
Notice of allowance dated Oct. 29, 2013 for U.S. Appl. No. 13/204,881.
Notice of allowance dated Nov. 16, 2015 for U.S. Appl. No. 14/493,734.
Notice of allowance dated Dec. 23, 2014 for U.S. Appl. No. 14/007,793.
Notice of allowance dated Dec. 23, 2015 for U.S. Appl. No. 12/493,122.
O'Connell. Hypertension Guide. cmbi.bjmu.edu. Jul. 14, 2008.
Office action dated Jan. 12, 2012 for U.S. Appl. No. 12/047,818.
Office action dated Jan. 15, 2014 for U.S. Appl. No. 13/836,135.
Office action dated Jan. 15, 2016 for U.S. Appl. No. 13/502,989.
Office action dated Jan. 16, 2014 for U.S. Appl. No. 12/046,252.
Office action dated Jan. 16, 2015 for U.S. Appl. No. 12/535,676.
Office action dated Jan. 22, 2013 for U.S. Appl. No. 13/562,999.
Office action dated Jan. 24, 2014 for U.S. Appl. No. 12/054,343.
Office action dated Jan. 24, 2014 for U.S. Appl. No. 12/786,739.
Office action dated Jan. 25, 2013 for U.S. Appl. No. 13/208,963.
Office action dated Jan. 26, 2016 for U.S. Appl. No. 12/054,343.
Office action dated Jan. 29, 2016 for U.S. Appl. No. 12/786,739.
Office Action dated Feb. 1, 2012 for U.S. Appl. No. 12/493,122.
Office action dated Feb. 1, 2016 for U.S. Appl. No. 13/503,844.
Office action dated Feb. 14, 2013 for U.S. Appl. No. 13/193,346.
Office action dated Feb. 14, 2013 for U.S. Appl. No. 13/407,408.
Office action dated Feb. 17, 2016 for U.S. Appl. No. 14/713,178.
Office action dated Feb. 21, 2013 for U.S. Appl. No. 12/047,818.
Office action dated Feb. 26, 2016 for U.S. Appl. No. 12/535,676.
Office action dated Mar. 2, 2016 for U.S. Appl. No. 14/693,711.
Office Action dated Mar. 5, 2012 for U.S. Appl. No. 12/535,676.
Office action dated Mar. 5, 2013 for U.S. Appl. No. 12/493,122.
Office action dated Mar. 6, 2015 for U.S. Appl. No. 13/757,412.
Office action dated Mar. 11, 2014 for U.S. Appl. No. 11/533,818.
Office Action dated Mar. 19, 2012 for U.S. Appl. No. 13/204,881.
Office action dated Mar. 22, 2016 for U.S. Appl. No. 13/733,873.
Office Action dated Mar. 23, 2012 for U.S. Appl. No. 13/271,783.
Office Action dated Mar. 29, 2011 for U.S. Appl. No. 12/054,343.
Office Action dated Mar. 30, 2011 for U.S. Appl. No. 12/786,739.
Office action dated Mar. 30, 2016 for U.S. Appl. No. 14/296,091.
Office action dated Apr. 4, 2016 for U.S. Appl. No. 13/313,629.
Office Action dated Apr. 5, 2012 for U.S. Appl. No. 11/555,697.
Office action dated Apr. 5, 2016 for U.S. Appl. No. 14/713,242.
Office action dated Apr. 6, 2015 for U.S. Appl. No. 14/493,734.
Office action dated Apr. 6, 2016 for U.S. Appl. No. 13/313,708.
Office Action dated Apr. 9, 2012 for U.S. Appl. No. 13/208,963.
Office action dated Apr. 10, 2014 for U.S. Appl. No. 13/502,989.
Office action dated Apr. 13, 2016 for U.S. Appl. No. 14/612,604.
Office action dated Apr. 16, 2014 for U.S. Appl. No. 13/705,763.
Office action dated Apr. 21, 2015 for U.S. Appl. No. 13/660,642.
Office action dated Apr. 21, 2015 for U.S. Appl. No. 14/087,930.
Office action dated Apr. 22, 2015 for US Application No. 13/836,135.
Office action dated Apr. 24, 2015 for U.S. Appl. No. 12/786,739.
Office Action dated Apr. 27, 2011 for U.S. Appl. No. 10/681,018.
Office action dated Apr. 27, 2015 for U.S. Appl. No. 12/054,343.
Office Action dated Apr. 28, 2011 for U.S. Appl. No. 12/283,090.
Office action dated May 6, 2015 for U.S. Appl. No. 12/493,122.
Office action dated May 7, 2015 for U.S. Appl. No. 13/705,763.
Office action dated May 9, 2013 for U.S. Appl. No. 13/204,881.
Office action dated May 12, 2014 for U.S. Appl. No. 13/733,873.
Office action dated May 13, 2014 for U.S. Appl. No. 13/313,629.
Office action dated May 15, 2013 for U.S. Appl. No. 13/502,989.
Office action dated May 15, 2014 for U.S. Appl. No. 13/448,061.
Office action dated May 16, 2014 for U.S. Appl. No. 13/313,708.
Office Action dated May 24, 11 for U.S. Appl. No. 12/487,864.
Office action dated May 27, 2015 for U.S. Appl. No. 13/502,989.
Office action dated Jun. 3, 2015 for U.S. Appl. No. 13/002,136.
Office action dated Jun. 13, 2012 for U.S. Appl. No. 12/493,122.
Office action dated Jun. 17, 2014 for U.S. Appl. No. 13/737,225.
Office action dated Jun. 17, 2014 for U.S. Appl. No. 13/757,412.
Office action dated Jun. 19, 2014 for U.S. Appl. No. 12/386,051.
Office action dated Jun. 25, 2013 for U.S. Appl. No. 13/144,286.
Office action dated Jun. 25, 2013 for U.S. Appl. No. 13/144,290.
Office action dated Jun. 27, 2012 for US Appl. No. 12/493,147.
Office action dated Jun. 27, 2014 for U.S. Appl. No. 14/007,793.
Office action dated Jun. 29, 2011 for U.S. Appl. No. 11/555,697.
Office action dated Jul. 7, 2014 for U.S. Appl. No. 12/535,676.
Office action dated Jul. 11, 2012 for U.S. Appl. No. 12/573,353.
Office action dated Jul. 15, 2013 for U.S. Appl. No. 13/002,136.
Office action dated Jul. 17, 2015 for U.S. Appl. No. 13/733,873.
Office action dated Jul. 18, 2012 for U.S. Appl. No. 12/047,818.
Office action dated Jul. 31, 2013 for U.S. Appl. No. 13/757,412.
Office action dated Aug. 2, 2013 for U.S. Appl. No. 12/535,676.
Office action dated Aug. 7, 2014 for U.S. Appl. No. 13/836,135.
Office action dated Aug. 13, 2012 for U.S. Appl. No. 13/208,963.
Office action dated Aug. 14, 2013 for U.S. Appl. No. 13/448,061.
Office action dated Aug. 28, 2013 for U.S. Appl. No. 13/313,629.
Office action dated Aug. 29, 2014 for U.S. Appl. No. 13/144,286.
Office action dated Aug. 31, 2015 for U.S. Appl. No. 12/535,676.
Office action dated Sep. 8, 2015 for U.S. Appl. No. 11/533,818.
Office action dated Sep. 9, 2013 for U.S. Appl. No. 13/502,989.
Office action dated Sep. 10, 2015 for U.S. Appl. No. 13/313,629.
Office action dated Sep. 11, 2015 for U.S. Appl. No. 13/313,708.
Office action dated Sep. 13, 2012 for U.S. Appl. No. 13/481,087.
Office action dated Sep. 18, 2014 for U.S. Appl. No. 13/502,989.
Office action dated Sep. 19, 2014 for U.S. Appl. No. 11/533,818.
Office action dated Sep. 19, 2014 for U.S. Appl. No. 13/737,225.
Office action dated Sep. 30, 2014 for U.S. Appl. No. 13/144,290.
Office action dated Sep. 30, 2014 for U.S. Appl. No. 13/660,642.
Office Action dated Jan. 21, 2011 for U.S. Appl. No. 12/386,051.
Office Action dated Jan. 29, 2002 for U.S. Appl. No. 09/707,395.
Office Action dated Jan. 8, 2010 for U.S. Appl. No. 10/681,018.
Office action dated Oct. 2, 2014 for U.S. Appl. No. 12/054,343.
Office action dated Oct. 6, 2014 for U.S. Appl. No. 12/493,122.
Office action dated Oct. 9, 2014 for U.S. Appl. No. 12/786,739.
Office Action dated Oct. 1, 2001 for U.S. Appl. No. 09/466,559.
Office action dated Oct. 10, 2012 for U.S. Appl. No. 13/204,881.
Office action dated Oct. 19, 2011 for U.S. Appl. No. 12/386,051.
Office action dated Oct. 24, 2013 for U.S. Appl. No. 13/313,708.
Office action dated Oct. 25, 2012 for U.S. Appl. No. 13/144,286.

(56) References Cited

OTHER PUBLICATIONS

Office action dated Oct. 25, 2012 for U.S. Appl. No. 13/144,290.
Office action dated Oct. 30, 2015 for U.S. Appl. No. 14/528,715.
Office Action dated Oct. 5, 2010 for U.S. Appl. No. 12/046,402.
Office action dated Nov. 7, 2014 for U.S. Appl. No. 13/705,763.
Office Action dated Nov. 14, 2007 for U.S. Appl. No. 11/213,255.
Office Action dated Nov. 15, 2010 for U.S. Appl. No. 12/238,415.
Office action dated Nov. 16, 2015 for U.S. Appl. No. 13/705,763.
Office action dated Nov. 19, 2015 for U.S. Appl. No. 14/713,242.
Office action dated Nov. 20, 2015 for U.S. Appl. No. 14/296,091.
Office action dated Nov. 20, 2015 for U.S. Appl. No. 14/612,604 .
Office action dated Nov. 21, 2014 for U.S. Appl. No. 13/926,822.
Office Action dated Nov. 25, 2009 for U.S. Appl. No. 11/232,180.
Office Action dated Nov. 26, 2001 for U.S. Appl. No. 09/466,559.
Office action dated Nov. 29, 2013 for U.S. Appl. No. 13/193,346.
Office action dated Dec. 6, 2012 for U.S. Appl. No. 13/002,136.
Office action dated Dec. 10, 2013 for U.S. Appl. No. 13/407,408.
Office action dated Dec. 10, 2015 for U.S. Appl. No. 13/836,135.
Office action dated Dec. 12, 2013 for U.S. Appl. No. 13/144,286.
Office action dated Dec. 13, 2013 for U.S. Appl. No. 12/493,122.
Office action dated Dec. 13, 2013 for U.S. Appl. No. 13/144,290.
Office action dated Dec. 15, 2011 for U.S. Appl. No. 12/493,147.
Office action dated Dec. 15, 2015 for U.S. Appl. No. 14/087,930.
Office action dated Dec. 16, 2013 for U.S. Appl. No. 12/535,676.
Office action dated Dec. 18, 2014 for U.S. Appl. No. 14/037,696.
Office action dated Dec. 18, 2015 for U.S. Appl. No. 14/640,385.
Office Action dated Dec. 19, 2005 for U.S. Appl. No. 10/730,567.
Office action dated Dec. 19, 2014 for U.S. Appl. No. 13/733,873.
Office Action dated Dec. 22, 2006 for U.S. Appl. No. 10/681,018.
Office action dated Dec. 24, 2015 for U.S. Appl. No. 13/757,412.
Office Action dated Mar. 18, 2008 for U.S. Appl. No. 11/468,379.
Office Action dated Mar. 25, 2008 for U.S. Appl. No. 11/213,382.
Office Action dated Mar. 28, 2008 for U.S. Appl. No. 11/555,697.
Office Action dated Apr. 12, 2010 for U.S. Appl. No. 09/990,909.
Office Action dated Apr. 21, 2008 for U.S. Appl. No. 11/232,180.
Office Action dated Apr. 22, 2003 for U.S. Appl. No. 09/929,592.
Office Action dated May 22, 2002 for U.S. Appl. No. 09/466,559.
Office Action dated Jun. 30, 2004 for U.S. Appl. No. 10/730,567.
Office Action dated Jul. 22, 2010 for U.S. Appl. No. 12/049,613.
Office Action dated Jul. 29, 2003 for U.S. Appl. No. 09/990,909.
Office Action dated Jul. 30, 2002 for U.S. Appl. No. 09/707,395.
Office Action dated Jul. 30, 2002 for U.S. Appl. No. 09/990,909.
Office Action dated Jul. 6, 2010 for U.S. Appl. No. 11/533,818.
Office Action dated Aug. 13, 2002 for U.S. Appl. No. 09/929,592.
Office Action dated Aug. 18, 2008 for U.S. Appl. No. 10/681,018.
Office Action dated Aug. 18, 2010 for U.S. Appl. No. 10/681,018.
Office Action dated Aug. 20, 2010 for U.S. Appl. No. 12/283,090.
Office Action dated Aug. 25, 2010 for U.S. Appl. No. 12/487,868.
Office Action dated Aug. 26, 2003 for U.S. Appl. No. 10/041,073.
Office Action dated Aug. 3, 2009 for U.S. Appl. No. 11/555,697.
Office Action dated Aug. 7, 2007 for U.S. Appl. No. 10/681,018.
Office Action dated Aug. 8, 2007 for U.S. Appl. No. 11/213,382.
Office Action dated Sep. 22, 2004 for U.S. Appl. No. 10/730,567.
Office Action dated Sep. 24, 2009 for U.S. Appl. No. 12/046,252.
Office Action Mailed May 11, 2016 U.S. Appl. No. 14/713,242.
Okahata, et al. Lipid-coated enzymes as efficient catalysts in organic media. Trends in Biotechnology. 1997; 15(2):50-54.
O'Keefe, Stephen J.D et al. The Exacerbation of Pancreatic Endocrine Dysfunction by Potent Pancreatic Exocrine Supplements in Patients with Chronic Pancreatitis. J. Clin. Gastroenterol. 32(4):319-323 (2001).
Olivar-Parra, et al. Training referential communicative skills to individuals with autism spectrum disorder: a pilot study. Psychological Reports. 2011; 109:921-939.
Owley, et al. Multisite, double-blind, placebo-controlled trial of porcine secretin in autism. J Am Acad Child Adolesc Psychiatry. Nov. 2001;40(11):1293-9.
P.Ya. Grigoryev et al., Reference Guide on Gastroenterology, Moscow, MIA-2003, pp. 454,460,465.

Pancrease. Patient information leaflet. Pancrease HL Capsules. Last updated Apr. 30, 2013. Janssen-cilag LTD. www.medicines.org.uk/EMC/medicine/7326.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Pancreatin 8X USP Powder. Product Specification. Jul. 2000. In: Product Manual. American Laboratories Incorporated. Omaha, NE. pg. 1.
Parisi et al. Evaluation of new rapid commercial enzyme immunoassay for detection of Crytosporidiumoocysts in untreated stool specimens. J Clin Microbiol. 1995; 33(7):1963-1965.
Park, et al. Increased apoptosis in cystinotic fibroblasts and renal proximal tubule epithelial cells results from cysteinylation of protein kinase Cdelta. J Am Soc Nephrol. Nov. 2006; 17(11):3167-75.
Parkinsons Disease Foundation. Parkinson's Disease Q&A. 2007. 1-44.
Parkinsons Disease Foundation. Ten Frequently-Asked Questions about Parkinson's Disease. 2006.
Parracho, et al. Differences between the gut microflora of children with autistic spectrum disorders and that of healthy children. J Med Microbiol. Oct. 2005;54(Pt 10):987-91.
Patel, et al. Formulation and evaluation of mucoadhesive glipizide microspheres. AAPS PharmSciTech. 2005; 6(1):E49-E55.
Patton, J. et al. Factor structure of the Barratt impulsiveness scale. Journal of Clinical Psychology, 51(6): 768-774 (Nov. 1995).
PDTALKS. Motivational & Inspirational Speaking From a Parkinson's Patient Perspective. pdtalks.com/Parkinson_s_Disease.html. Jul. 14, 2008.
Perman et al. Role of pH in production of hydrogen from carbohydrates by colonic bacterial flora. J Clin Invest. 1981; 24(4):684-685.
Persico, et al. Searching for ways out of the autism maze: genetic, epigenetic and environmental clues. Trends Neurosci. Jul. 2006;29(7):349-58.
Peters et al. Prevalence of enteric parasites in homosexual patients attending an outpatient clinic. J of Clin Micro. 1986; 24(4):684-685.
Peters, et al. Treatment of alcoholic polyneuropathy with vitamin B complex: a randomised controlled trial. Alcohol. Nov.-Dec. 2006;41(6):636-42. Epub Aug. 21, 2006.
Petrolatum: Pharmaceutical Excipients. London: Pharmaceutical Press. 2006. 1-6.
Pisani, et al. Levodopa-induced dyskinesia and striatal signaling pathways. Proc Natl Acad Sci USA. Mar. 3, 2009;106(9):2973-4. Epub Feb. 26, 2009.
Polanczyk, et al. The worldwide prevalence of ADHD: a systematic review and metaregression analysis. Am J Psychiatry. Jun. 2007;164(6):942-8.
Ponsky, et al. Alterations in gastrointestinal physiology after Roux-en-Y gastric bypass. J Am Coll Surg. Jul. 2005;201(1):125-31.
Proesmans, Marijke et al. Omeprazole, a proton pump inhibitor, improves residual steatorrhoea in cystic fibrosis patients treated with high dose pancreatic enzymes. European Journal of Pediatrics 162(11): 760-763 (Nov. 2003).
Puri, et al. Isolated segmental duodenal ganglionosis. Indian Journal of Radiology and Imaging. 2000; 153-154.
Qi, et al. Solubility and emulsifying properties of soy protein isolates modified by pancreatin. Journal of Food Science 62.6 (1997): 1110-1115.
Raimondo, et al. Rapid endoscopic secretin simulation test and discrimination of chronic pancreatitisand pancreatic cancer from disease controls. Clin Gastroenterol Hepatol. Sep. 2003;1(5):397-403.
Rajakumar, et al. Proteasomal activity in placentas from women with preeclampsia and intrauterine growth restriction: implications for expression of HIF-alpha proteins. Placenta. Mar. 2008;29(3):290-9. Epub Jan. 28, 2008.
Rakonczay, et al. A new severe acute necrotizing pancreatitis model induced by L-ornithine in rats. Crit Care Med. Jul. 2008;36(7):2117-27.
Ray, et al. Growth factor regulation of enterocyte nutrient transport during intestinal adaptation. Am J Surg. Apr. 2002;183(4):361-71.

(56) References Cited

OTHER PUBLICATIONS

Reeves, G. et al. Pharmacological Management of Attention-deficit hyperactivity disorder, Expert Opinion on Pharmacotherapy, 5;6; 1313-1320. (Feb. 25, 2005)DOI: 10.1517/14656566.5.6.1313 http://dx.doi.org/10.1517/14656566.5.6.1313.
Regan, et al. Comparative effects of antacids, cimetidine and enteric coating on the therapeutic response to oral enzymes in severe pancreatic insufficiency. N Engl J Med. Oct. 20, 1977;297(16):854-8.
Remtulla et al. Stool chymotrypsin activity measured by a spectrophotometric procedure to identify pancreatic disease in infants. Clinical Biochemistry. Dec. 1986; 19:341-342.
Revolution health. Enzyme therapy. revolutionhealth.com/drugs-treatments/enzyme-therapy. Sep. 2, 2008.
Richards, et al. Diagnosis, management, and treatment of Alzheimer disease: a guide for the internist. Arch Intern Med. Apr. 26, 1999;159(8):789-98.
Rider, et al. Perspective of biochemical research in the neuronal ceroid-lipofuscinosis. Am J Med Genet. Feb. 15, 1992;42(4):519-24.
Riedel, L et al. Limitations of faecal chymotrypsin as a screening test for chronic pancreatitis. Gut, 32:321-324 (1991).
Rivest, J. et al. A dynamic model of protein digestion in the small intestine of pigs. Journal of Animal Science, 78(2):328-240 (Feb. 2000).
Robinson, T. et al. Incentive-sensitization and addiction. Addiction, 96(1):103-114 (Jan. 2001).
Rogers. No more heartburn: Stop the pain in 30 days—naturally. 2000; 172.
Rottier, et al. Lack of PPCA expression only partially coincides with lysosomal storage in galactosialidosis mice: indirect evidence for spatial requirement of the catalytic rather than the protective function of PPCA. Hum Mol Genet. Oct. 1998;7(11):1787-94.
Roxas, et al. Colds and influenza: a review of diagnosis and conventional, botanical, and nutritional considerations. Alternative Medicine Review. 2007; 12(1):25-48.
Rubenstein, et al. Model of autism: increased ratio of excitation/inhibition in key neural systems. Genes Brain Behav. Oct. 2003;2(5):255-67.
Rudell, et al. The anterior piriform cortex is sufficient for detecting depletion of an indispensable amino acid, showing independent cortical sensory function. J Neurosci. Feb. 2, 2011;31(5):1583-90. Abstract only.
Sabra, et al. Linkage of ileal-lymphoid-nodular hyperplasia (ILNH), food allergy and CNS developmental: evidence for a non-IgE association. Ann Aller Asth Immunol. 1999; 82(1):81. Abstract only.
Sahelian. Enzymes. raysahelian.com/enzymes.html. Sep. 2, 2008.
Salpekar, et al. Bipolar Spectrum Disorder Comorbid With Autism Spectrum Disorder; NADD Bulletin, vol. X, 2007. No. 6, Article 1, pp. 1-5, downloaded from http://www.thenadd.org/nadd-bulletin/archive/volunne-x/ on Dec. 11, 2018.
Sandler et al. Short term benefit from oral vancomycin treatment of regressive-onset autism. J of Child Neuro. 2000; 15(7):42-435.
Sandler, et al. Lack of benefit of a single dose of synthetic human secretin in the treatment of autism and pervasive developmental disorder. N Engl J Med. Dec. 9, 1999;341(24):1801-6.
Schafer, et al. Stress kinases and heat shock proteins in the pancreas: possible roles in normal function and disease. J Gastroenterol. 2000;35(1):1-9.
Schain, RJ et al. Studies on 5-hydroxyindole metabolism in autistic and other mentally retarded children. J. Pediatr. 58:315-320 (1961) [Summary Only].
Schedl, H. et al. Absorption of I-methionine from the human small intestine. Journal of Clinical Investigation, 47(2): 417-425 (1968).
Schiller. Review article: the therapy of constipation. Aliment Pharmacol Ther. 2001; 15:749-763.
Schizophreniform disorder. Merck Manuals Online Medical Library. Nov. 2005. (in Japanese with English translation).
Schneider, et al. Oral human immunoglobulin for children with autism and gastrointestinal dysfunction: a prospective, open-label study. J Autism Dev Disord. Nov. 2006;36(8):1053-64.
Schreck et al. Food preferences and factors influencing food selectivity for children with autism spectrum disorders. Res Develop Disabil. 2006; 27:353-363.
Schumann. Medical, nutritional and technological properties of lactulose. An update. Eur J Nutr. Nov. 2002;41 Suppl 1:I17-25.
Seltzer, et al. The Symptoms of Autism Spectrum Disorders in Adolescence and Adulthood. Journal of Autism and Developmental Disorders. 2003; 33(6):565-581.
Seneca et al. Enhancement of brain I-dopa concentration with a-chymotrypsin. J American Geriatrics Society. 1973; 256-258. Abstract only.
Serna, et al. Pathogenesis and treatment of Shiga toxin-producing Escherichia coli infections. Curr Opin Gastroenterol. Jan. 2008;24(1):38-47.
Settembre, et al. A block of autophagy in lysosomal storage disorders. Hum Mol Genet. Jan. 1, 2008;17(1):119-29.
Shadel. Expression and maintenance of mitochondrial DNA: new insights into human disease pathology. Am J Pathol. Jun. 2008;172(6):1445-56.
Shaul. Report to the Chairman and Ranking Minority Member, Subcommittee on Human Rights and Wellness, Committee on Government Reform, House of Representatives. GEO. Jan. 2005. 1-40.
Shelby, et al. Enzymatic debridement with activated whole pancreas. American Journal of Surgery. Oct. 1958; 96(4):545-549.
Sherwood et al. A new class of high-functionality excipients: silicified microcrystalline cellulose. Pharm Tech. 1998; 22(10):78-88.
Sherwood, et al. Activation of trypsinogen in large endocytic vacuoles of pancreatic acinar cells. Proc Natl Acad Sci U S A. Mar. 27, 2007;104(13):5674-9.
Shimabukuro, et al. Medical expenditures for children with an autism spectrum disorder in a privately insured population. J Autism Dev Disord. 2007;38(3):546-52.
Shpacovitch, et al. Protease-activated receptors: novel PARtners in innate immunity. Trends Immunol. Dec. 2007;28(12):541-50.
Shpacovitch, et al. Role of protease-activated receptors in inflammatory responses, innate and adaptive immunity. J Leukoc Biol. Jun. 2008;83(6):1309-22.
Sienaert, et al. Evidence-based treatment strategies for treatment-resistant bipolar depression: a systematic review. Bipolar Disord. Feb. 2013;15(1):61-9. doi: 10.1111/bdi.12026. Epub Nov. 27, 2012.
Sillanaukee, et al. Improved diagnostic classification of alcohol abusers by combining carbohydrate-deficient transferrin and gamma-glutamyltransferase. Clin Chem. Apr. 2001;47(4):681-5.
Simonoff, et al. Psychiatric disorders in children with autism spectrum disorders: prevalence, comorbidity, and associated factors in a population-derived sample. J Am Acad Child Adolesc Psychiatry. Aug. 2008;47(8):921-9.
Singh et al. Past, Present, and Future Technologies for Oral Delivery of Therapeutic Proteins. J Pham Sci 97(7):2497-2523 (2008).
Singh, et al. Plasma increase of interleukin-12 and interferon-gamma. Pathological significance in autism. J Neuroimmunol. May 1996;66(1-2):143-5.
Singh, Manjit. Alcoholic pancreatitis in rats fed ethanol in a nutritionally adequate liquid diet. International Journal of Pancreatology, 2:311-324 (1987).
Skeels et al. Crytosporidium infection in Oregon public health clinic patients 1985-88: the value of statewide laboratory surveillance. AJPH. 1990; 80(3):305-308.
Skinner, et al. Treatment of Prion Disease with Heterologous Prion Proteins. PLoS One. Jul. 2, 2015;10(7):e0131993. doi: 10.1371/journal.pone.0131993. eCollection 2015.
Smith, et al. Fecal chymotrypsin and trypsin determinations. Canadian Medical Association Journal. 1971; 104(8):691-4 and 697.
Sousa, et al. Polymorphisms in leucine-rich repeat genes are associated with autism spectrum disorder susceptibility in populations of European ancestry. Mol Autism. Mar. 2, 20105;1(1):7.
Statemaster. Number of Children with Autism (most recent w/graph) by state. Statemaster.com Jul. 14, 2003.

(56) References Cited

OTHER PUBLICATIONS

Statemaster. Number of Children with Autism (most recent) by state. Statemaster.com Jul. 14, 2008.
Statemaster. Number of Children with Autism (per capita)(most recent) by state. Statemaster.com Jul. 14, 2003.
Stein, et al. Nitrogen metabolism in normal and hyperkinetic boys. Am J Clin Nutr. Apr. 1984;39(4):520-4.
Steinherz, et al. Patterns of amino acid efflux from isolated normal and cystinotic human leucocyte lysosomes. J Biol Chem. Jun. 10, 1982;257(11):6041-9.
Sternby, et al. Carboxyl Ester Lipase (Bile Salt-Stimulated Lipase), Colipase, Lipase, and Phospholipase A2 Levels in Pancreatic Enzyme Supplements, 1997, Scandinavian Journal of Gastroenterology 32(3): 261-267.
Stoll, et al. Enteral nutrient intake level determines intestinal protein synthesis and accretion rates in neonatal pigs. Am J Physiol Gastrointest Liver Physiol. Aug. 2000;279(2):G288-94.
Stott, et al. MMR and Autism in Perspective: the Denmark Story. J. Am Phys Surg. 2004;9(3):89-91.
Strader, et al. Structural basis of ß-adrenergic receptor function. FASEB J. May 1989;3(7):1825-32.
Sturmey. Secretin is an ineffective treatment for pervasive developmental disabilities: a review of 15 double-blind randomized controlled trials. Res Dev Disabil. Jan.-Feb. 2005;26(1):87-97.
Sundstrom, et al. A deadly prion disease: fatal familial insomnia. J Neurosci Nurs. Dec. 2003;35(6):300-5. Abstract only.
Swayne, et al. Pathobiology of H5N2 Mexican avian influenza virus infections of chickens. Vet Pathol. Nov. 1997;34(6):557-67.
Tager-Flusberg, et al. Language disorders: autism and other pervasive developmental disorders. Pediatr Clin North Am. Jun. 2007;54(3):469-81, vi.
Tamaro. Vitamin K deficiency as a cause of autistic symptoms. Http://web.archive.org/web/20090612022246/http://www.gutresearch.com/VitaminK.pdf. Published Jun. 12, 2009 as per Wayback Engine.
Tang, G. et al. Loss of mTOR-dependent macroautophagy causes autistic-like synaptic pruning deficits. Neuron, 83(5):1131-1143 (Sep. 3, 2014).
Terrie, et al. Understanding Pancreatic Enzyme Products. Dec. 15, 2008.
The Alzheimer's Association. Basics of Alzheimer's Disease. 2005, 32 pages. http://www.alz.org/national/documents/brochure_Basicsofalz_low/pdf.
TheFreeDictionary. Term Sprinkles. Www.thefreedictionary.com. Accessed Nov. 2, 2011. 1 page.
Therapeutic research center. Approved Pancreatic Enzyme Products. Pharmacist's Letter/Prescriber's Letter 2010. Oct. 2010. 1-3.
Thomas, et al. Defective protein folding as a basis of human disease. Trends Biochem Sci. Nov. 1995;20(11):456-9.
Tiedermann, et al. Identification of a potent natural triterpenoid inhibitor of proteosome chymotrypsin-like activity and NF-kappaB with antimyeloma activity in vitro and in vivo. Blood. Apr. 23, 2009;113(17):4027-37.
Torrente, et al. Focal-enhanced gastritis in regressive autism with features distinct from Crohn's and Helicobacter pylori gastritis. Am J Gastroenterol. Apr. 2004;99(4):598-605.
Torrente, et al. Small intestinal enteropathy with epithelial lgG and complement deposition in children with regressive autism. Mol Psychiatry. 2002;7(4):375-82, 334.
Tran, et al. Treatment of complex regional pain syndrome: a review of the evidence. Can J Anaesth. Feb. 2010;57(2):149-66.
Trauner, et al. Specific cognitive deficits in young children with cystinosis: evidence for an early effect of the cystinosin gene on neural function. J Pediatr. Aug. 2007;151(2):192-6.
Troy. Pancreatic Enzymes. Remington: The Science and Practice of Pharmacy, 21st edition. Lippincot Williams & Wilkins, 2006. p. 1304.
Tsan, et al. Heat shock proteins and immune system. J Leukoc Biol. Jun. 2009; 85(6):905-10.
Tsang et al. Extragastroduodenal conditions associated with Helicobacter pylori infection. Hong Kong Medical Journal. 1999; 5(2):169-174.
Tuohy, K.M. et al. Using probiotics and prebiotics to improve gut health. Reviews, Therapeutic Focus, DDT 8(15) Aug. 2003.
U.S. Appl. No. 11/533,818 Final Office Action Mailed Jun. 7, 2016.
U.S. Appl. No. 12/054,343 Final Office Action Mailed May 10, 2017.
U.S. Appl. No. 12/054,343 Non-Final Office Action Mailed Dec. 26, 2017.
U.S. Appl. No. 12/054,343 Office Action Mailed Aug. 19, 2016.
U.S. Appl. No. 12/535,676 Non-Final Office Action Mailed Apr. 21, 2017.
U.S. Appl. No. 12/535,676 Non-Final Office Action Mailed Sep. 6, 2018.
U.S. Appl. No. 12/535,676 Office Action Mailed Sep. 13, 2016.
U.S. Appl. No. 12/786,739 Final Office Action mailed Jun. 23, 2017.
U.S. Appl. No. 12/786,739 Final Office Action Mailed Sep. 25, 2018.
U.S. Appl. No. 12/786,739 Non-Final Office Action Mailed Jan. 4, 2018.
U.S. Appl. No. 12/786,739 Office Action Mailed Sep. 20, 2016.
U.S. Appl. No. 13/002,136 Advisory Office Action Mailed Jul. 9, 2018.
U.S. Appl. No. 13/002,136 Final Office Action Mailed Jan. 8, 2018.
U.S. Appl. No. 13/002,136 Final Office Action Mailed Jun. 24, 2016.
U.S. Appl. No. 13/002,136 Non-Final Office Action Mailed Dec. 18, 2018.
U.S. Appl. No. 13/002,136 Non-Final Office Action Mailed Feb. 27, 2017.
U.S. Appl. No. 13/193,346 Notice of Allowability Mailed Jul. 14, 2016.
U.S. Appl. No. 13/193,346 Notice of Allowability Mailed Jun. 2, 2016.
U.S. Appl. No. 13/313,629 Notice of Allowance Mailed Dec. 22, 2016.
U.S. Appl. No. 13/313,708 Notice of Allowance Mailed Dec. 15, 2016.
U.S. Appl. No. 13/502,989 Notice of Allowance Mailed Aug. 10, 2016.
U.S. Appl. No. 13/503,844 Final Office Action Mailed Nov. 30, 2017.
U.S. Appl. No. 13/503,844 Office Action Mailed Aug. 25, 2016.
U.S. Appl. No. 13/503,844 Office Action Mailed Mar. 27, 2017.
U.S. Appl. No. 13/705,763 Final Office Action Mailed May 24, 2016.
U.S. Appl. No. 13/733,873 Final Office Action Mailed Feb. 21, 2018.
U.S. Appl. No. 13/733,873 Non-Final Office Action Mailed May 25, 2017.
U.S. Appl. No. 13/757,412 Final Office Action Mailed Jun. 30, 2016.
U.S. Appl. No. 13/757,412 Final Office Action Mailed Sep. 12, 2017.
U.S. Appl. No. 13/757,412 Office Action dated Apr. 16, 2019.
U.S. Appl. No. 13/757,412 Office Action Mailed Feb. 10, 2017.
U.S. Appl. No. 13/836,135 Final Office Action Mailed Dec. 14, 2018.
U.S. Appl. No. 13/836,135 Final Office Action Mailed May 15, 2017.
U.S. Appl. No. 13/836,135 Non-Final Office Action Mailed Mar. 15, 2018.
U.S. Appl. No. 13/836,135 Notice of Allowance dated Apr. 25, 2019.
U.S. Appl. No. 13/836,135 Office Action Mailed Jul. 22, 2016.
U.S. Appl. No. 14/296,091 Final Office Action Mailed Aug. 23, 2017.
U.S. Appl. No. 14/296,091 Final Office Action Mailed Jan. 3, 2017.
U.S. Appl. No. 14/296,091 Final Office Action Mailed Oct. 1, 2018.
U.S. Appl. No. 14/296,091 Non-Final Office Action Mailed Mar. 22, 2018.
U.S. Appl. No. 14/612,580 Final Office Action Mailed Aug. 10, 2017.
U.S. Appl. No. 14/612,580 Notice of Allowability Mailed Mar. 1, 2018.

(56) References Cited

OTHER PUBLICATIONS

U.S. Appl. No. 14/612,580 Notice of Allowance Mailed Jan. 12, 2018.
U.S. Appl. No. 14/612,580 Office Action Mailed Sep. 21, 2016.
U.S. Appl. No. 14/612,604 Notice of Allowance Mailed Jul. 20, 2016.
U.S. Appl. No. 14/639,425 Notice of Allowance Mailed Mar. 10, 2017.
U.S. Appl. No. 14/639,425 Office Action Mailed Jul. 14, 2016.
U.S. Appl. No. 14/640,385 Supplemental Notice of Allowability Mailed May 26, 2016.
U.S. Appl. No. 14/693,711 Final Office Action Mailed Dec. 15, 2016.
U.S. Appl. No. 14/693,711 Notice of Allowability Mailed May 26, 2017.
U.S. Appl. No. 14/693,711 Notice of Allowance Mailed Apr. 21, 2017.
U.S. Appl. No. 14/713,178 Advisory Office Action Mailed Jan. 19, 2017.
U.S. Appl. No. 14/713,178 Final Office Action Mailed Oct. 14, 2016.
U.S. Appl. No. 14/713,178 Notice of Allowance Mailed Apr. 12, 2017.
U.S. Appl. No. 14/713,221 Final Office Action Mailed Jun. 16, 2016.
U.S. Appl. No. 14/713,221 Non-Final Office Action Mailed Dec. 30, 2016.
U.S. Appl. No. 14/713,221 Notice of Allowance Mailed Oct. 19, 2017.
U.S. Appl. No. 14/713,242 Final Office Action Jan. 9, 2019.
U.S. Appl. No. 14/713,242 Final Office Action Mailed Jul. 21, 2017.
U.S. Appl. No. 14/713,242 Non-Final Office Action Mailed Mar. 29, 2018.
U.S. Appl. No. 14/713,242 Office Action Mailed Dec. 7, 2016.
U.S. Appl. No. 14/921,896 Final Office Action Mailed Jan. 25, 2018.
U.S. Appl. No. 14/921,896 Notice of Allowability Mailed Sep. 12, 2018.
U.S. Appl. No. 14/921,896 Notice of Allowance Mailed Jul. 18, 2018.
U.S. Appl. No. 14/921,896 Office Action Mailed Apr. 26, 2017.
U.S. Appl. No. 15/089,842 Final Office Action Mailed Dec. 4, 2018.
U.S. Appl. No. 15/089,842 Non-Final Office Action Mailed Jun. 26, 2018.
U.S. Appl. No. 15/089,842 Office Action Mailed Dec. 8, 2017.
U.S. Appl. No. 15/164,493 Non-Final Office Action Mailed Feb. 27, 2018.
U.S. Appl. No. 15/164,493 Notice of Allowance Mailed Nov. 15, 2018.
U.S. Appl. No. 15/185,511 Notice of Allowance Mailed Nov. 16, 2017.
U.S. Appl. No. 15/265,415 Non-Final Office Action Mailed Apr. 11, 2018.
U.S. Appl. No. 15/265,620 Non-Final Office Action Mailed Jan. 22, 2019.
U.S. Appl. No. 15/265,620 Non-Final Office Action Mailed Jun. 20, 2018.
U.S. Appl. No. 15/354,940 Non-Final Office Action Mailed Nov. 2, 2018.
U.S. Appl. No. 15/593,121 Non-Final Office Action Mailed Mar. 8, 2018.
U.S. Appl. No. 15/593,129 Office Action dated Jan. 3, 2019.
U.S. Appl. No. 16/103,192 Office Action dated Nov. 4, 2019.
U.S. Appl. No. 12/786,739 Office Action dated May 8, 2019.
U.S. Appl. No. 13/733,873 Office Action dated May 16, 2019.
U.S. Appl. No. 15/074,115 Office Action dated Mar. 6, 2019.
U.S. Appl. No. 15/265,415 Notice of Allowance dated Dec. 26, 2018.
U.S. Appl. No. 15/354,940 Final Office Action date Aug. 21, 2019.

U.S. Appl. No. 15/593,121 Notice of Allowance dated Dec. 26, 2018.
U.S. Appl. No. 15/840,883 Office Action dated Aug. 8, 2019.
U.S. Appl. No. 12/535,676 Office Action dated Jun. 26, 2019.
U.S. Appl. No. 13/002,136 Office Action dated Jun. 21, 2019.
U.S. Appl. No. 14/612,580 Office Action dated Dec. 24, 2015.
U.S. Appl. No. 15/089,842 Notice of Allowance dated Mar. 29, 2019.
Uhlmann, et al. Potential viral pathogenic mechanism for new variant inflammatory bowel disease. Mol Pathol. Apr. 2002;55(2):84-90.
ULTRESA—FDA Prescribing Information Side Effects and Uses. Revised Sep. 2014.
ULTRESA. Highlights of prescribing information. Aptalis Pharma US Inc. Revised Mar. 2012.
Unis, et al. A randomized, double-blind, placebo-controlled trial of porcine versus synthetic secretin for reducing symptoms of autism. J Am Acad Child Adolesc Psychiatry. Nov. 2002;41(11):1315-21.
UPI. Number of autistic Calif. students triples. United Press International. Jul. 12, 2008.
USDA. FDA Drug Safety Communication: Clostridium difficile-associated diarrhea can be associated with stomach acid drugs known as proton pump inhibitors (PPIs). Safety announcement. Feb. 8, 2012. Accessed Apr. 1, 2013. http://www.fda.gov/drugs/drugsafety/ucm290510.htm.
USP (32)-NF(27) 2009, Pancreatin, V.3, pp. 3194-3195.
Valicenti-McDermott, et al. Frequency of gastrointestinal symptoms in children with autistic spectrum disorders and association with family history of autoimmune disease. J Dev Behav Pediatr. Apr. 2006;27(2 Suppl):S128-36.
Vargas, et al. Neuroglial activation and neuroinflammation in the brain of patients with autism. Ann Neurol. Jan. 2005;57(1):67-81.
Vellard. The enzyme as drug: application of enzymes as pharmaceuticals. Curr Opin Biotechnol. Aug. 2003;14(4):444-50.
Vilanova, et al. Preparative isolation of the two forms of pig pancreatic pro-(carboxypeptidase A) and their monomeric carboxypeptidases A. Biochem J. Aug. 1, 1985;229(3):605-9.
Viokace—FDA Prescribing Information, Side Effects and Uses. Revised Mar. 2012.
Viokace. Highlights of prescribing information. Aptalis Pharma US Inc. Revised Mar. 2012.
Vojdani, et al. Antibodies against CNS antigens in autism: Possible cross-reaction with dietary proteins and infectious agent antigens. Neuropsychiatric Disorders and Infection. 2004; 19:171-186.
Vojdani, et al. Heat shock protein and gliadin peptide promote development of peptidase antibodies in children with autism and patients with autoimmune disease. Clin Diagn Lab Immunol. May 2004;11(3):515-24.
Vojdani, et al. Immune response to dietary proteins, gliadin and cerebellar peptides in children with autism. Nutr Neurosci. Jun. 2004;7(3):151-61.
Volkmar, et al. Practice parameters for the assessment and treatment of children, adolescents, and adults with autism and other pervasive developmental disorders. American Academy of Child and Adolescent Psychiatry Working Group on Quality Issues. J Am Acad Child Adolesc Psychiatry. (PART 1) Dec. 1999;38(12 Suppl):32S-54S.
Volkmar, et al. Practice Parameters for the Assessment and Treatment of Children, Adolescents, and Adults with Autism and other Pervasive Developmental Disorders. American Academy of Child and Adolescent Psychiatry. J Am Acad Child Adolesc Psychiatry. (PART 2) Dec. 1999;38(12):1611-6.
Wakefield, et al. Enterocolitis in children with developmental disorders. Am J Gastroenterol. Sep. 2000;95(9):2285-95.
Wakefield, et al. Ileal-lymphoid-nodular hyperplasia, non-specific colitis, and pervasive developmental disorder in children. Lancet. Feb. 28, 1998;351(9103):637-41.
Wakefield, et al. Review article: the concept of entero-colonic encephalopathy, autism and opioid receptor ligands. Aliment Pharmacol Ther. Apr. 2002;16(4):663-74.
Wakefield, et al. The significance of ileo-colonic lymphoid nodular hyperplasia in children with autistic spectrum disorder. Eur J Gastroenterol Hepatol. Aug. 2005; 17(8):827-36.

(56) References Cited

OTHER PUBLICATIONS

Wakefield. Autistic enterocolitis: is it a histopathological entity? Histopathology. 2006; 1-5.
Wakefield. Enterocolitis, Autism, and Measles Virus. Consensus in Child Neurology: Biological Bases and Clinical Perspectives in Autism. 2002; 74-81.
Wakefield. The gut-brain axis in childhood developmental disorders. J Pediatr Gastroenterol Nutr. May-Jun. 2002;34 Suppl 1:S14-7.
Walsh, et al. Heat shock and the role of the HSPs during neural plate induction in early mammalian CNS and brain development. Cell Mol Life Sci. Feb. 1997;53(2):198-211.
Walsh, et al. Reduced violent behavior following chemical therapy. Physiology and behavior. 2004; 82:835-839.
Wang, et al. Activation of Ras/Erk pathway by a novel MET-interacting protein RanBPM. J Biol Chem. Sep. 27, 2002;277(39):36216-22.
Wang, et al. Effect of chymotrypsin C and related proteins on pancreatic cancer cell migration. Acta Biochim Biophys Sin (Shanghai). May 2011;43(5):362-71. Epub Apr. 2, 2011. Jan. 7, 2011. Abstract only.
We Move, PD Workbook, The WEMOVE Clinician's Guide to Parkinson's Disease, 2006.
Weintraub, et al. Morphometric studies of pancreatic acinar granule formation in NCTR-Balb/c mice. J Cell Sci. May 1992;102 ( Pt 1):141-7.
Welch, et al. Brain effects of chronic IBD in areas abnormal in autism and treatment by single neuropeptides secretin and oxytocin. J Mol Neurosci. 2004;25(3):259-74.
Wender et al. Prevalence of attention deficit disorder, residual type, and other psychiatric disorders in patients with irritable colon syndrome. Am J Psychiatry. 1983; 140(12):1579-82 Abstract only.
Whitehouse. Fact Sheet: Combating Autism Act of 2006. www.whitehouse.gov. Dec. 19, 2006.
Williams, et al. Eating habits of children with autism. Pediatr Nurs. May 2000-Jun. 26(3):259-64.
Williams, et al. Intravenous secretin for autism spectrum disorders (ASD). Cochrane Database Syst Rev. Apr. 18, 2012;4:CD003495. doi: 10.1002/14651858.CD003495.pub3.
Williams, K. et al. Cochrane Review: Selective serotonin reuptake inhibitors (SSRIs) for autism spectrum disorders (ASD). Evidence-Based Child Health: A Cochrane Review Journal, 6(4):1044-1078 (Jul. 2011). [Abstract Only].
Wisniewski, et al. Therapeutic approaches for prion and Alzheimer's diseases. FEBS J. Aug. 2007;274(15):3784-98. Epub Jul. 6, 2007.
Witmer. ADD and ADHD Statistics—CDC Report Looks at Attention-Deficit/Hyperactivity Disorder. About.com—Parenting of Adolescents. Jul. 15, 2008.
Wohlman et al. Enhancement of drug activity by chymotrypsin, penicillin penetration into granulomatous lesions and inflammatory fluids. Cellular and Molecular Life Sciences. 1969; 25(9):953-954.
Wolfson, D., Making sense of digestive enzymes, Klaire Labs, Mar. 13, 2006.
Woodward et al. Ischaemic enterocolitis complicating aidiopathic dysautonomia. Gut. 1998; 43:285-287.
Xu. Pancreatin therapy in chronic pancreatitis. Clin J Dig, May 2005; 25(5):313-315. (in Chinese with English translation).
YAHOO !. com. Who is affected by Parkinson's disease. Yahoo! Health. Jul. 14, 2008.
Yang, et al. Polymeric Porous Framework of a Bismuth Citrate-Based Complex: A Potential Vehicle for Drug Delivery. Medical News Today. Dec. 17, 2010. 1-4.
Yang, Xinyi et al. Advances in anti-staphylococcal agent lysostaphin. Chinese Journal of New Drugs 14(9):1113-1117 (2005).
Yazbak. Autism in the United States: a perspective. Journal of American Physicians and Surgeons. 2003;8:103-107.
Youngberg, et al. Comparison of gastrointestinal pH in cystic fibrosis and healthy subjects. Dig Dis Sci. May 1987;32(5):472-80.
Yuan, et al.. Freeze-Thaw Stability of Three Waxy Maize Starch Pastes Measured by Centrifugation and Calorimetry. Cereal Chem. 1998; 75(4):571-573.
Zeiner, et al. Mammalian protein RAP46: an interaction partner and modulator of 70 kDa heat shock proteins. Embo J. Sep. 15, 1997;16(18):5483-90.
ZENPEP—FDA Prescribing Information, Side Effects and Uses. Revised Sep. 2014.
ZENPEP. Highlights of prescribing information. Eurand Pharmaceuticals Inc. Revised Jul. 2011.
Zhang et al. Lactulose-mannitol intestinal permeability test in children with diarrhea caused by rotavirus and cryptosporidium. J of Pediatric Gastro & Nutrition. 2000; 31(1):16-21.
Hsiao: Gastrointestinal issues in autism spectrum disorder. Harv Rev Psychiatry. 22(2):104-111 doi:10.1097/HRP.0000000000000029 (2014).
Kedem et al.: Attention deficit hyperactivity disorder and gastrointestinal morbidity in a large cohort of young adults. World J Gastroenterol. 26(42):6626-6637 doi:10.3748/wjg.v26.i42.6626 (2020).
Steinberg et al.: Blood, Sweat and Tears darkfield, enzymes and schizophrenia. The Townsend Letter 255:63-66 (2004).
U.S. Appl. No. 17/159,846 Non-Final Office action dated Dec. 23, 2022.
U.S. Appl. No. 17/235,646 Non-Final Office Action dated Jul. 5, 2023.
Dydyk et al. "Opioid Use Disorder", In: StatPearls [Internet], Treasure Island (FL): StatPearls Publishing; Jan. 2024 Available from: https://www.ncbi.nlm.nih.gov/books/NBK553166/ (Year: 2024).
Felman, "What are the symptoms of addiction?", Medical News Today, Oct. 26, 2018, https://www.medicalnewstoday.com/articles/323459#overview (Year: 2018).
Gullo et al. "Effect of cessation of alcohol use on the course of pancreatic dysfunction in alcoholic pancreatitis", Gastroenterology, vol. 95, ISSUE 4, P1063-1068, Oct. 1988 (Year: 1988).
Hendler et al. "Stimulant and Sedative Effects of Alcohol", May 2011 Current Topics in Behavioral Neurosciences 13:489-509DOI:10.1007/7854_2011_135 (Year: 2011).
Lopez-Otin et al.: Proteases: multifunctional enzymes in life and disease. J Biol Chem. 283(45):30433-30437 doi:10.1074/jbc.R800035200 (2008).
Nehring et al. "Alcohol Use Disorder", In: StatPearls [Internet], Treasure Island (FL): StatPearls Publishing; Jan. 2024 Available from: https://www.ncbi.nlm.nih.gov/books/NBK436003/ (Year: 2024).
"Pancreatic enzymes (medication)", https://en.wikipedia.org/wiki/Pancreatic_enzymes_(medication) (Year: 2024).
"Protease", https://en.wikipedia.Org/wiki/Protease#Biodiversity_of_proteases (Year: 2024).
Ramo et al., "Self-Administration of Enzyme Substitution in the Treatment of Exocrine Pancreatic Insufficiency", Scandinavian Journal of Gastroenterology, vol. 24, 1989—Issue 6, pp. 688-692. Published online: Jul. 8, 2009 (Year: 1989).
"United States Pharmacopeia" https://en.wikipedia.org/wiki/United_States_Pharmacopeia (Year: 2024).
U.S. Appl. No. 17/551,942 Office Action dated Mar. 25, 2024.

* cited by examiner

| Trypsin | Lysine | Arginine | | |
|---|---|---|---|---|
| Chymotrypsin | Tryptophan<br>• Serotonin synthesis<br>• Niacin<br>• Maintain nitrogen balance | Methionine<br>• Initiation codon for protein synthesis<br>• Methylation | Phenylalanine<br>• Dopamine, Norepinephrine, Epinephrine synthesis<br>• Precursor to tyrosine | Leucine<br>• Only amino acid to stimulate muscle protein synthesis<br>• Ferritin subunit |
| Elastase | Valine | Glycine | | Tyrosine |

Essential Amino Acids: Lysine, Tryptophan, Methionine, Phenylalanine, Leucine and Valine.

Semi/Non Essential Amino Acids: Arginine, Tyrosine and Glycine.

FIG. 1

COMPOSITIONS FOR TREATING ADDICTION

CROSS REFERENCE

This application is a national stage entry of International Application No. PCT/US18/26841, filed on Apr. 10, 2018, which claims the benefit of U.S. Provisional Patent Application No. 62/483,856, filed on Apr. 10, 2017, which is incorporated by reference herein in its entirety.

BACKGROUND

Addiction is one of the most costly public health problems in the United States. It is a progressive syndrome, which means that it increases in severity over time unless it is treated. Substance abuse is characterized by frequent relapse, or return to the abused substance. Substance abusers often make repeated attempts to quit before they are successful.

In 1995 the economic cost of substance abuse in the United States exceeded $414 billion, with health care costs attributed to substance abuse estimated at more than $114 billion.

By eighth grade, 52% of adolescents have consumed alcohol, 41% have smoked tobacco, and 20% have smoked marijuana. Compared to females, males are almost four times as likely to be heavy drinkers, nearly one and a half more likely to smoke a pack or more of cigarettes daily, and twice as likely to smoke marijuana weekly. However, among adolescents these gender differences are decreasing. Although frequent use of tobacco, cocaine and heavy drinking appears to have remained stable in the 1990s, marijuana use increased.

In 1999, an estimated four million Americans over the age of 12 used prescription pain relievers, sedatives, and stimulants for "nonmedical" reasons during one month.

In the United States, 25% of the population regularly uses tobacco. Tobacco use reportedly kills 2 5 times as many people each year as alcohol and drug abuse combined. According to 1998 data from the World Health Organization, there were 1.1 billion smokers worldwide and 10,000 tobacco-related deaths per day. Furthermore, in the United States, 43% of children aged 2 to 11 years are exposed to environmental tobacco smoke, which has been implicated in sudden infant death syndrome, low birth weight, asthma, middle ear disease, pneumonia, cough, and upper respiratory infection.

SUMMARY OF THE INVENTION

Provided herein are methods of treating addiction by administering to the subject pharmaceutical compositions that comprise digestive enzymes. In some instances of such methods, treatment reduces an amount of $\Delta Fos\beta$ in the subject.

Provided herein is a method for treating a subject having an addiction, comprising administering to the subject a therapeutically effective amount of a pharmaceutical composition that comprises digestive enzymes to the subject, whereby the addiction is treated, and wherein the addiction is a drug addiction, an alcohol addiction, or a nicotine addiction. In some instances, administration of the pharmaceutical composition reduces an amount of $\Delta Fos\beta$ in the subject compared to prior to administration of the pharmaceutical composition. In certain instances, the digestive enzymes comprise an amylase, a lipase, and a protease.

Provided herein is a method of reducing an elevated amount of $\Delta Fos\beta$ in a subject having an addiction, comprising administering to the subject a therapeutically effective amount of a pharmaceutical composition that comprises digestive enzymes, wherein the transcription factor is elevated in the subject due to the addiction compared to a subject without the addiction. In certain instances, the digestive enzymes comprise an amylase, a lipase, and a protease.

Provided herein is a method of decreasing an amount or length of dendritic spines in nerve cells of a subject having an addiction, comprising administering to the subject a therapeutically effective amount of a pharmaceutical composition that comprises digestive enzymes, thereby decreasing an amount of dendritic spines in nerve cells of the subject to an amount that is lower than prior to administration of the pharmaceutical composition. In certain instances, the digestive enzymes comprise an amylase, a lipase, and a protease.

Provided herein is a method of treating an addiction in a subject in need thereof, comprising administering to the subject one or more doses of a pharmaceutical composition that comprises digestive enzymes; wherein the digestive enzymes that comprise a protease, an amylase and a lipase; wherein a dose of the pharmaceutical composition at one point of administration to the subject comprises from about 650,000 units of the protease to about $1.5 \times 10^6$ units of the protease.

In such methods, in some instances, the digestive enzymes in the pharmaceutical composition further comprise an enteric coating or a lipid coating.

In some aspects, a pharmaceutical composition described herein is encapsulated.

The pharmaceutical composition is a dosage form can be, for example, a capsule, a tablet, or a sachet.

It will be understood that, when referencing a "dose" of the pharmaceutical composition, the dose refers to about 4, about 5, about 6, about 7, about 8, or about 9 capsules, tablets or sachets.

The pharmaceutical composition may be administered to the subject from about one to about three times per day. In some instances, the pharmaceutical is administered to the subject three times a day. In other instances, the pharmaceutical is administered to the subject two times a day. In other instances, the pharmaceutical is administered to the subject one time per day. It will be understood that if a subject demonstrates a reduction in the addiction, then the amount of the pharmaceutical composition to be administered to the subject at each dose and/or the number of administrations per day may be reduced.

The pharmaceutical composition may be administered to the subject with a meal.

Provided herein is a method of treating an addiction in a subject in need thereof, comprising administering to the subject one or more doses of a pharmaceutical composition that comprises encapsulated coated digestive enzyme particles; wherein the coated digestive enzyme particles comprise (i) a core that comprises digestive enzymes that comprise a protease, an amylase and a lipase, and (ii) a coating; wherein a dose of the pharmaceutical composition comprises from about 4 to about 9 capsules of the encapsulated coated digestive enzyme particles; wherein from about 4 to about 9 capsules are administered to the subject three times a day with meals for at least 12 weeks; and wherein from about 650,000 units of the protease to about $1.5 \times 10^6$ units of the protease are administered to the subject with each meal.

The subject may be addicted to one or more drugs, one or more types of alcohol, one or more types of nicotine, or a combination thereof.

In one instance, the addiction comprises a drug addiction. A drug as disclosed herein refers to, for example, an opiate, cocaine, crack, ecstasy, PCT, LSD, or a combination thereof.

Opiates include, but are not limited to, a natural opiate, a synthetic opiate, or a combination thereof.

Natural opiates include, but are not limited to, opium, morphine, codeine, heroin, and a combination thereof.

Synthetic opiates include, but are not limited to, Dilaudid (hydromorphone hydrochloride), Demerol, Oxycodone, Vicodin, Fentanyl, Methadone, and a combination thereof.

The amylase, in some instances, is present in the pharmaceutical composition in an amount of from about 120,000 to about 370,000 U.S.P. units/unit dose.

The protease, in some instances, is present in the pharmaceutical composition in an amount of from about 130,000 to about 165,000 U.S.P. units/unit dose.

The lipase, in some instances, is present in the pharmaceutical composition in an amount of from about 17,000 to about 60,000 U.S.P. units/unit dose.

A total protease and a total lipase in the pharmaceutical composition in U.S.P. units are present in a ratio of protease to lipase of from about 1:1 to about 20:1.

A total protease and a total lipase in the pharmaceutical composition in U.S.P. units are present in a ratio of protease to lipase of from about 4:1 to about 10:1.

A total protease and a total lipase in the pharmaceutical composition in U.S.P. units are present in a ratio of protease to lipase of 4:1, 5:1, 6:1, 7:1, 8:1, 9:1, or 10:1.

A total protease and a total amylase in the pharmaceutical composition in U.S.P. units are present in a ratio of protease to amylase of 1:0.1 to 1:10.

The pharmaceutical composition may be manufactured using any suitable technology including those selected from the group consisting of direct compression, dry granulation, wet granulation, and a combination thereof.

The pharmaceutical composition, in some instances, comprises coated digestive enzyme particles.

The pharmaceutical composition, in some instances, comprises coated digestive enzyme particles that are encapsulated.

Coated digestive enzyme particles comprise (i) a core that comprises the digestive enzymes and (ii) a coating.

In certain instances, the coating comprises an enteric coating.

In other instances, the coating comprises a lipid.

A lipid can comprise a food grade lipid such as, for example, a sorbitan monostearate, a sorbitan tristearate, or a calcium stearoyl lactylate.

A lipid can comprise a pharmaceutical grade lipid such as, for example, a soybean oil that is fully hydrogenated (fully-hydrogenated soybean oil).

A lipid can comprise one or more monoglycerides, one or more diglycerides, one or more triglycerides, fatty acids, esters of fatty acids, phospholipids, or a combination thereof. In some instances, the lipid comprises one or more monoglycerides. In some instances, the lipid comprises one or more diglycerides. In some instances, the lipid comprises one or more triglycerides. In some instances, the lipid comprises monoglycerides and diglycerides. In some instances, the lipid comprises monoglycerides and triglycerides. In some instances, the lipid comprises diglycerides and triglycerides. In some instances, the lipid comprises monoglycerides, diglycerides and triglycerides.

A lipid can comprise a hydrogenated lipid, a saturated lipid, a partially saturated lipid, or a combination thereof.

In some instances, the lipid comprises a soy lipid. A soy lipid can comprise a hydrogenated soy lipid.

Where the lipid comprises the esters of fatty acids, the esters of fatty acids are selected from the group consisting of acetic acid esters of mono- and diglycerides, citric acid esters of mono- and diglycerides, lactic acid esters of mono- and diglycerides, polyglycerol esters of fatty acids, propylene glycol esters of fatty acids, and diacetyl tartaric acid esters of mono- and diglycerides.

The lipid can comprise comprises a hydrogenated castor wax or a hydrogenated carnauba wax.

The lipid can comprise an animal lipid or a vegetable lipid such as, for example, a palm kernel oil, a soybean oil, a cottonseed oil, a canola oil and a poultry fat.

The pharmaceutical composition can be administered to the subject orally.

The pharmaceutical composition can be a dosage formulation selected from the group consisting of a pill, a tablet, a capsule, a sprinkle, a sachet, and a combination thereof. In some instances, the capsule comprises a microcapsule, a mini-capsule, a time released capsule, or a combination thereof. In some instances, the tablet comprises a minitab.

The coated digestive enzyme particles can, in some instances, be encapsulated in a gelatin capsule or a hydroxypropyl methylcellulose (HPMC) capsule. An HPMC capsule can comprise a size 00 capsule or a size 0 capsule.

Where the pharmaceutical composition comprises a capsule, a single capsule comprises a protease activity of from about 135,000 United States Pharmacopeia (U.S.P.) units/mg to about 150,000 U.S.P. units/mg.

In some instances, the subject is administered one or more doses of the pharmaceutical composition.

A dose of the pharmaceutical composition can comprise from about 4,000 to about 9,000 mg of the digestive enzymes.

The digestive enzymes can be present in the coated particles in an amount of from about 70% to about 90% by weight, or from about 75% to about 85% by weight. In some of the disclosed methods, the digestive enzymes can be present in the coated particles in an amount of about 70% by weight. In some of the disclosed methods, the digestive enzymes can be present in the coated particles in an amount of about 72.5% by weight. In some of the disclosed methods, the digestive enzymes can be present in the coated particles in an amount of about 75% by weight. In some of the disclosed methods, the digestive enzymes can be present in the coated particles in an amount of about 77.5% by weight. In some of the disclosed methods, the digestive enzymes can be present in the coated particles in an amount of about 80% by weight. In some of the disclosed methods, the digestive enzymes can be present in the coated particles in an amount of about 82.5% by weight. In some of the disclosed methods, the digestive enzymes can be present in the coated particles in an amount of about 85% by weight. In some of the disclosed methods, the digestive enzymes can be present in the coated particles in an amount of about 875% by weight. In some of the disclosed methods, the digestive enzymes can be present in the coated particles in an amount of about 90% by weight.

In one instance, at least 90% of the coated particles are from about 105 µm to about 425 µm in size. In one instance, at least 75% of the coated particles are from about 180 µm to about 425 µm in size. In one instance, less than about 20% of the coated particles are capable of being sieved through about 150 µm mesh. In one instance, less than about 15% of the coated particles are capable of being sieved through about 150 µm mesh.

In such methods, the ΔFosβ can comprise ΔFosβ. An amount of the ΔFosβ after administration of the pharmaceutical composition to the subject can be at least about 2-fold, at least about 3-fold, at least about 4-fold, at least about 5-fold, at least about 10-fold, at least about 50-fold, or at least about 100-fold lower than the amount of the ΔFosβ prior to administration of the pharmaceutical composition.

An amount of the ΔFosβ after administration of the pharmaceutical composition to the subject can be at least about 2%, about 5%, about 10%, about 15%, about 20%, about 25%, about 30%, about 35%, about 40%, about 45%, about 50%, about 55%, about 60%, about 65%, about 70%, about 75%, about 80%, less than the amount of the ΔFosβ prior to administration of the pharmaceutical composition.

The pharmaceutical composition can be packaged in a blister pack, a trilaminar foil pouch, or a bottle. A bottle is, for example, a glass bottle or a plastic bottle sealed with foil. The pharmaceutical composition can packaged in a blister pack that comprises a foil backing.

Administration of the pharmaceutical composition to the subject can reduce a craving associated with the addiction. The method can reduce the length of the craving, the severity of the craving, or the length of the craving and the severity of the craving.

Administration of the pharmaceutical composition to the subject can reduce impulsivity associated with the addiction. The method can reduce the length of the impulsivity, the severity of the impulsivity, or the length of the impulsivity and the severity of the impulsivity.

Administration of the pharmaceutical composition to the subject can reduce can reduce a lack of impulse control associated with the addiction.

Administration of the pharmaceutical composition to the subject can reduce a craving associated with the addiction and can reduce a lack of impulse control associated with the addiction.

Administration of the pharmaceutical composition to the subject can reduce a craving associated with the addiction and reduces impulsivity associated with the addiction.

Administration of the pharmaceutical composition to the subject impulsivity associated with the addiction and reduces a lack of impulse control associated with the addiction.

In some aspects, a blood sample can be obtained from the subject and tested for a level of phenylalanine prior to commencement of treatment, and at one or more time points during and/or after treatment. The blood level of phenylalanine in the subject can be compared to a normal blood level of phenylalanine from a healthy, non-addicted subject. In some instances, the normal blood level of phenylalanine from a healthy, non-addicted subject comprises from about 2 mg/dL to about 6 mg/dL of phenylalanine.

In some instances, the normal blood level of phenylalanine from a healthy, non-addicted subject comprises from about 120 micromolar to about 360 micromolar of phenylalanine.

Provided herein is a pharmaceutical composition for treatment of an addiction in a subject in need thereof, wherein the pharmaceutical composition comprises encapsulated, coated digestive enzyme particles, wherein the coated digestive enzyme particles comprise (i) a core that comprises digestive enzymes that comprise a protease, an amylase and a lipase, and (ii) a coating. In some instances, the coating comprises a lipid coating. In other instances, the coating comprises an enteric coating.

A dose of the pharmaceutical composition can comprise from about 4 to about 8 capsules and each capsule can comprise from about 135,000 United States Pharmacopeia (U.S.P.) units/mg to about 150,000 U.S.P. units/mg. of protease activity. A single administration time point of the pharmaceutical composition can, therefore, comprise from about 650,000 U.S.P. units to about $1.5 \times 10^6$ U.S.P. units. of protease activity.

The pharmaceutical composition may be formulated to be administered to the subject three times a day, and the pharmaceutical composition to be administered at each dosage event comprises from about 4,000 mg to about 9,000 mg of the digestive enzymes.

In one aspect, provided herein is the use of any of the pharmaceutical compositions described herein, in the formulation of a medicament for the treatment of an addiction in a subject in need thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DISCLOSURE OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 illustrates essential and non-essential amino acids.

DETAILED DESCRIPTION OF THE INVENTION

Figure 2:
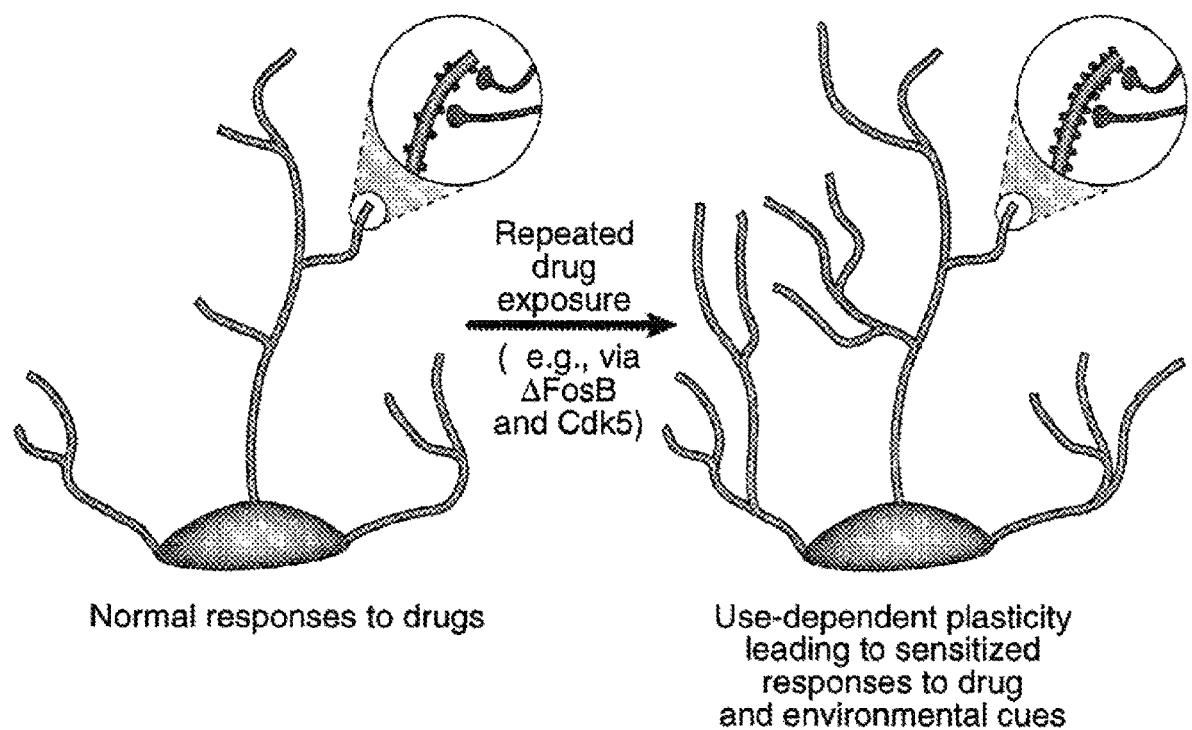
FIG. 2 depicts proliferation of dendritic splines as a result of repeated drug use.

It is to be understood that this application is not limited to particular formulations or process parameters, as these may, of course, vary. It is also to be understood that the terminology used herein is for the purpose of describing particular embodiments only, and is not intended to be limiting. Further, it is understood that a number of methods and materials similar or equivalent to those described herein can be used in the practice of the present inventions.

The terms "about" and "approximately" includes equal to, and a range that takes into account experimental error in a given measurement. As used herein, the terms "about" and "approximately," when used to modify a numeric value or numeric range, indicate that deviations of plus or minus (±) 10, 9, 8, 7, 6, 5, 4, 3, 2 or 1% or anywhere in-between. For example, a value may be 0.2%, 0.5%, 1%, 2.5%, 5%, 7.5%, or 10% (or any integer between about 0.2% and 10%) above or below the value or range remain within the intended meaning of the recited value or range. In some instances, the term "about" refers to plus or minus (±) 2%, 1.5%, 1%, 0.5% or 0.2% of the indicated value.

As used in this specification and the appended claims, the singular forms "a", "an", and "the" include plural references unless the context clearly dictates otherwise. Thus, for example purposes only, references to "a method" include one or more methods, and/or steps of the type described herein and/or which will become apparent to those persons skilled in the art upon reading this disclosure.

As used herein, "addiction" refers to a dependence on a behavior or substance that a subject is powerless to stop or is difficult to stop. The term has been partially replaced by the word "dependence" for substance abuse. Addiction includes mood-altering behaviors or activities. There is a growing recognition that many addicts can be addicted to more than one substance.

The invention relates to the use of digestive enzymes in the treatment of a drug addiction, an alcohol addiction, or a combination thereof.

According to the Office of National Drug Control Policy, there are over 3 million long-term cocaine users in the United States. There are currently no medications approved to treat cocaine addiction. Cocaine addiction can produce significant morbidity and mortality. There is a large need for effective treatment that can produce changes in overall craving and subsequently reduce cocaine use.

According to the National Survey on Drug Use and Health (NSDUH) adults aged 18 to 25 years have a higher rate of current cocaine use than any other age group, with 1.5 percent of young adults reporting cocaine use in the past month. Overall, men report higher rates of current cocaine use than women. Further, data from the 2008 Drug Abuse Warning Network (DAWN) report showed that cocaine was involved in 482,188 of the nearly 2 million visits to emergency departments for drug misuse or abuse. This translates to almost one in four drug misuse or abuse emergency department visits (24 percent) that involved cocaine.

The liver is one of the most injured organs in cases of alcoholism and drug abuse. The reason is because the liver is part of the digestive system and is used by the body to filter out and store toxins. When it is overtaxed, the liver can become fatty or damaged or both. It is critical that those going through drug or alcohol rehabilitation emphasize liver healing.

Alcohol blocks the absorption and breakdown of nutrients by damaging the cells lining the stomach and intestines, and by decreasing the amount of digestive enzymes secreted by the pancreas. For reasons that aren't yet known, the pancreas can become inflamed and leak digestive enzymes, which then attack the pancreas itself.

Amino acids have long been described as the building blocks of proteins. Amino acids are classified as essential, non-essential and semi-essential. Essential amino acids are those that the body cannot synthesize or otherwise obtain endogenously in both children and adults. These essential amino acids must be obtained exogenously by eating a protein a n d breaking the protein down into its component amino acids through enzymatic hydrolysis. Semi-essential amino acids are those that young children must obtain exogenously since they cannot be synthesized or procured endogenously in the pediatric population. Semi-essential amino acids can be procured or synthesized endogenously in adults. Non-essential amino acids are those that the body can procure or synthesize endogenously in both adults and children.

Amino acids are cleaved from the ingested protein as mono-, di-, tri-tetra- and higher peptide fragments. Amino acid pool depletion and the lack of the building blocks for new proteins represent one way in which diminished numbers of amino acids, especially essential amino acids Phenylalanine has been found to play in the pathophysiology of addiction especially cocaine addiction quite possibly by the delta fosβ (ΔFosβ) theory of brain change resulting in addiction.

Emerging evidence demonstrates that amino acids are not only involved in protein synthesis but also play a significant role in other important neurological functions. For example those essential amino acids cleaved by the digestive enzyme chymotrypsin, phenylalanine and tryptophan, are necessary components of the body's synthesis of dopamine and serotonin respectively.

Physiology

Classical thinking with respect to amino acids identifies them as the building blocks of new proteins synthesized by the body. Essential amino acids need to be ingested in the form of protein and are cleaved from that protein. They cannot be obtained any other way or synthesized by the body. Further the administration of these essential amino acids directly into the GI tract results in poor uptake and utilization. The semi-essential act similarly as essential amino acids in small children and the non-essential amino acids can be synthesized by the body without any additional input from ingested exogenous proteins.

While this classical view has been held for decades, we now know the demarcation between essential and non-essential is not as well defined as previously believed. For example, the endogenous synthesis of many non-essential amino acids is under the direct control of essential amino acids. So while in theory a non-essential can be synthesized, an essential amino acid may be necessary for that synthesis to occur.

Further, for example, the essential amino acid methionine serves as the initiation codon at the beginning of all protein synthesis in humans. This is also a very important amino acid with respect to RNA replication. Leucine is the only amino acid required to optimally stimulate muscle protein synthesis. Both methionine and leucine and the processes they enable are necessary in childhood for growth and repair.

In addition to their role in neurotransmitters, regulators of protein degradation, nitrogen physiology and catabolism, amino acids are emerging as important regulators of gene expression. This role was only first described in the literature over the last 15 years.

Starvation of certain amino acids can actually determine the up-regulation or down-regulation of specific genes. For example, gene expression is strongly induced in response to methionine starvation. The CHOP gene is of particular interest because of its role in controlling neural pruning in the developing brain through apoptosis.

There are a wide variety of mechanisms by which amino acids can affect regulation of gene expression. Experiments conducted in yeast have shown that regulation can proceed through very specific forms of control such as those reliant upon end products of enzymes associated with a particular biosynthetic pathway. For example, the synthesis of leucine is controlled by the transcriptional activator Leu3p in response to the availability of leucine.

An additional example of regulation is found in the deprivation of certain amino acids or stress such as that from heat shock. In this instance, a lack of specific amino acids causes the corresponding tRNAs to accumulate, which in turn leads to an increased production of a transcriptional regulator.

There have been well over 500 genes identified that can be affected by the presence of absence of specific amino acids. Through the outside availability of food sources or the ability of the body to utilize those sources; this relatively new finding in gene regulation represents an important source of epigenetic influence affecting the course of disease pathology.

The pathophysiology section below describes new theories of cocaine addiction and the role of the brain transcription factor ΔFosβ being interdependent with the essential amino acid phenylalanine. The changes in ΔFosβ after cocaine use result in elongation of the dendritic spines in the presence of a depleted source of phenylalanine.

The role of amino acid and especially amino acid pool depletion especially of essential amino acids, is no longer relegated to simply "the building blocks of protein".

Pathophysiology

Deciphering the genetic code over the last 3 decades has revealed the presence of three separate stop codons and a single start codon in DNA. The start codon is so designated because this is the point where the information for creating any particular protein begins in the genome. This information is initially stored in DNA and consists of a sequence of purine and pyrimidine bases. The code sequence is always the same and it specifically codes for the amino acid methionine. Thus, methionine is the first amino acid contained in all proteins created by the body. By virtue of its status as the initial amino acid for all protein synthesis, methionine is absolutely essential for life.

The lack of amino acids can affect multiple processes in the human body, including but not limited to the formation of neurotransmitters, epigenetic influences, protein catabolism and anabolism, multiple levels of transcription and persistence of addictive behaviors. The fact that the lack or presence of amino acids can have an epigenetic effect and potentially turn on and off gene expression adds to the importance of the availability of a complete amino acid pool. While the complex balance of amino acids is necessary for life, there are basic tenets of that balance that hold true for all human proteomics:

An Amino Acid Response system (AAR) has been identified; this system signals and identifies deficiencies and imbalances in amino acids in the human body.

Dietary intake of amino acids is typically not balanced to exactly match the body's demands for various amino acids.

Amino acids taken via the diet must be chemically modified and rearranged to provide adequate levels of all the amino acids needed.

Essential amino acids can only be procured from ingested protein; they cannot be manufactured in the body.

Non-essential amino acids can be manufactured in the body, however, in some cases they are under the direct control of essential amino acids.

Amino acid absorption pathways in the gastrointestinal mucosa are configured to transport di and tri-peptides, not single amino acids. Supplementation with single amino acids will not be sufficient for the replacement of amino acids due to a lack of protein ingestion.

In humans, unlike other mammals, levels of protein in the diet cannot induce digestive proteases to pathologic levels. Amylases and to some degree lipases can be induced by the level of carbohydrate and fat in the diet.

There are a significant number of pathways in the body for balancing the pool of amino acids, both for synthesis and for degradation. The number of enzymes and co-enzymes necessary for each creates a great potential for disease when there is a deficiency in the pathway.

The genetic influences of the amino acids may account for certain disease states.

Disruption of the amino acid sequence, even by just one amino acid, can have profound consequences for growth and development. The consequences may be physiological, cognitive, psychological and behavioral. Some of these are inheritable and many are fatal.

The essential and non-essential amino acids have the ability to control protein synthesis, gene regulation, nitrogen balance and neurotransmission, among other things. The importance of the amino acid supply and the ability to synthesize non-essential and to obtain essential amino acids from the diet is paramount. The inability of the body to directly synthesize essential amino acids and the fact that the essential amino acids play a role in the synthesis of non-essential amino acids, as in the case of asparagine which is under the control of methionine (an essential amino acid, see FIG. 1), underscores the importance of the enzyme's activity and its ability to aid in the breakdown of protein and supply the body's amino acid pool.

The utilization and absorption of amino acids and the preferential uptake in the gastrointestinal system (specifically in the duodenum), is accomplished by the absorption of di- and tripeptides through the mucosa. There appears to be a preferential absorption (in volume and rate) of di and tri-peptides over both single amino acids and tetra and higher peptides. This is an important aspect of enzyme replacement utilization for those who lack chymotrypsin, or have an abnormally low level of fecal chymotrypsin (FCT). For children presenting with low/pathological levels of chymotrypsin, the need to deliver di- and tri peptides to the small intestinal mucosa for absorption is paramount.

Amino acid channels can be established in the small intestines where the specific breakdown of protein into di and tri-peptides occurs, but also, the amino acids are preferentially and more expeditiously absorbed in those forms, as evidenced by the 2-3 times faster absorption in the form of di and tri-peptides.

The absorption channels that allow for the maximized absorption of di and tri-peptides in the mucosal wall of the small intestine do not support the administration of single amino acids, which are in many dietary supplements. These single amino acids are mainly destroyed by the gastric acid of the stomach. Further, these absorption channels are the preferential way in which these di and tri-peptides are absorbed.

A large subgroup of children have been found to exhibit low levels of fecal chymotrypsin, thus, signaling the potential for the lack of protein digestion as chymotrypsin is one of the main protease enzyme in the human body. The inability to induce pathological levels pointed to the fact that this sub group may actually have a deficit in protein digestion. As chymotrypsin cleaves phenylalanine, tryptophan methionine and leucine, the indications for neurological implications of the potential lack of amino acids in the generalized amino acid pools was profound.

The lack of enzyme and the connection to neurological function cannot be ignored. It has been reported in the literature that children with low levels of tryptophan may also have low amounts of serotonin. Serotonin is a neurotransmitter that is found in the GI tract (80%), brain and platelets in humans and thought to be involved in the brain's control over behavior. Behaviors such as appetite, mood, aggression, sleep, memory, cognition, motor and sexual function have been cited as potential targets for serotonin's influence on behavior. Further, it may play a role in neuroendocrine signaling.

Deficiencies in serotonin have been linked to depression, increased appetite and other disorders. Since it has been linked to depression, there are a large number of antidepressants that target serotonin metabolism. One of these classes of drugs, the serotonin reuptake inhibitors (SSRI's), prevents the body from reabsorbing serotonin so that it can remain in the brain and remain available for the synapses.

The emergence of evidence with respect to cocaine addiction and the role of ΔFosβ that builds up in the brains of cocaine addicts is implicated in the persistence of cocaine addiction. In some instances, a subject to be treated with a method described herein comprises a subject addicted to a natural opiate, a synthetic opiate, or a combination thereof. Non-limiting examples of natural opiates include, but are not limited to, opium, morphine, codeine, heroin, etc., or a combination thereof. Synthetic opiates, on the other hand, are man-made in a laboratory and are most often used to treat chronic or severe pain. Non-limiting examples of synthetic opiates include, but are not limited to, Dilaudid, Demerol, Oxycodone, Vicodin, Fentanyl, Methadone, etc., or a combination thereof. In other instances, a subject to be treated with a method described herein comprises a subject addicted to crack, ecstasy, PCT, LSD, etc., or a combination thereof.

The presence of cocaine in the body of a subject can produce increased utilization of dopamine at the sites of dopamine transporters. The pleasure reward mechanism, loss of control, and compulsive behaviors are controlled by the limbic system which contains cells that are highly responsive to dopamine. These responsive cells are designed to trigger pleasurable responses that both make us feel good and want to repeat the experience. In some instances the drive for sexual pleasure and gratification can promote a desire to mate and result in species survival. On the other hand, the same mechanism can help to keep us repeating pleasurable yet destructive behaviors such as those seen in addiction.

ΔFosβ is a unique transcription factor that is derived from the fosB gene via alternative splicing and is known, therefore, as a genetic transcription factor.

One potentially key type of cocaine-related change that appears to last for many months after the last cocaine exposure, and perhaps longer is an alteration in the physical structure of nerve cells in the NAc. Chronic cocaine exposure causes these cells to extend and sprout new offshoots on their dendrites. Dendrites are the branch-like fibers that grow out from nerve cell bodies and collect incoming signals from other nerve cells. Just as a bigger antenna picks up more radio waves, more dendrite branches in the NAc theoretically will collect a greater volume of nerve signals coming from other regions—for example, the hippocampus, amygdala, and frontal cortex.

Because cocaine addiction decreases stores of phenylalanine, elongation of the dendritic spines occurs in the presence of a depleted source of phenylalanine. The converse is true in the case of PKU (phenyl ketone urea) where there is a buildup of phenylalanine, causing the dendrites to become stubs. Normal health subjects have baseline levels of phenylalanine of from about 2 mg/dL to about 6 mg/dL, or from about 120 micromolar to about 360 micromolar. It would be understood that a decreased store of phenylalanine can be 2-fold or more compared to the normal baseline.

The formation of the ΔFosβ from the Fosβ in the nucleus accumbens may occur through a "Leucine Zipper" mechanism where Leucine is found at every $7^{th}$ amino acid position. The elongation of the dendritic spines found in the presence of the ΔFosβ is regulated by the presence or absence of phenylalanine. The addition thereby results in an altered ratio of leucine/phenylalanine.

ΔFosBβ is naturally present in small quantities in the cells of the Nucleus Accumbens in the brain, and chronic cocaine exposure causes it to accumulate to high levels. It has been postulated by some that ΔFosβ may play a role as a molecular "switch" in the transition from drug abuse to addiction, mainly for the following reasons.

Once created, a molecule of ΔFosβ lasts for 6 to 8 weeks before breaking apart chemically. Therefore, each new episode of cocaine abuse exacerbates the buildup of ΔFosβ that has accumulated from all previous episodes during roughly 2 months. If someone is abusing cocaine daily, the levels of ΔFosβ will be extremely elevated all the time.

ΔFosβ causes the elongation of and formation of dendritic spines, which may induce and maintain cocaine cravings; in the presence of phenylalanine, the elongation recedes to a normal state.

Mice with elevated ΔFosβ exhibit a set of behaviors that correspond to human addictive behaviors, while mice with normal levels of ΔFosβ do not. Conversely, blocking the buildup of ΔFosβ in mice during a regimen of cocaine exposure reduces these behaviors.

Chronic administration of cocaine increase ΔFosβ in several brain regions, most specifically the nucleus accumbens (NAc). Additionally, ΔFosβ also builds up in such areas as the frontal cortex and amygdala. The accumulations of ΔFosβ in the frontal cortex and the amygdala are much smaller than those that cocaine causes in the NAc.

ΔFosβ may cause more than 25 percent of chronic cocaine-induced changes in gene expression in the NAc—a finding that highlights the dominant role of this transcription factor in mediating cocaine's genetic effects in the brain. One of the genes stimulated by ΔFosβ is an enzyme, cyclin-dependent kinase-5 (CDK5), which promotes nerve cell growth. This finding sheds light on mechanisms underlying cocaine's very long-lasting effects on the brain.

Because ΔFosβ is induced in brain specifically by and remains in these brain regions for long periods of time, ΔFosβ may act as a sustained "molecular switch" that first initiates and then maintains some of the long-term adaptations of the brain in response to chronic perturbations.

Essential Amino Acids as well as non-essential amino acids play important roles in neurological function by directly affecting gene expression. The role of amino acids in gene expression opens up new doors to the role of epigenetics and disease such as addiction.

One key type of cocaine-related change that appears to last for many months after the last cocaine exposure, and perhaps longer is an alteration in the physical structure of nerve cells in the NAc. Chronic cocaine exposure causes these cells to extend and sprout new offshoots on their dendrites. Dendrites are the branch-like fibers that grow out from nerve cell bodies and collect incoming signals from other nerve cells. Just as a bigger antenna picks up more radio waves, more dendrite branches in the NAc theoretically will collect a greater volume of nerve signals coming from other regions—for example, the hippocampus, amygdala, and frontal cortex.

This elongation of the dendritic spines occurs in the presence of a depleted source of phenylalanine. The converse is true in the case of PKU (phenylketonuria) where there is a buildup of phenylalanine, causing the dendrites to become stubs. FIG. 2 illustrates proliferation of dendritic spines as a result of repeated drug use.

Emerging evidence demonstrates that amino acids are not only involved in protein synthesis but also play a significant role in other important neurological functions. Of the four essential amino acids cleaved by chymotrypsin, phenylalanine and tryptophan are necessary components of the body's synthesis of dopamine and serotonin, respectively.

The hypodopamanergic state, which has been hypothesized in cocaine addiction, may be amenable to treatment with a pharmaceutical composition described herein. The administration of the pharmaceutical composition can, in some instances, enhance the cleavage of phenylalanine and thereby increase the pool of this essential amino acid, the building block of dopamine. See, e.g., FIG. 1.

Coated Digestive Enzyme Particles and Formulations

Provided herein are pharmaceutical compositions for use in an addiction treatment program for an active alcoholic and/or a drug addict. The pharmaceutical compositions may also be utilized to keep someone at risk for becoming an addict or it may be used to prevent someone from relapsing into addiction.

The pharmaceutical compositions may also be utilized for those who are deemed at risk for addiction due to family history or other historical events, such as severe stress or other factors placing the subject at risk.

As used herein, a "drug" refers to an addictive drug including, but not limited to, nicotine, cocaine, crack, heroin, PCP, LCD, ecstasy, or any other addictive drug.

As used herein, an "alcohol" refers to any type of alcohol including, but not limited to wine, beer, or a hard alcohol such as, for example, whisky, gin, moonshine, vodka, rum, etc.

As used herein, a "polyaddict" refers to a subject that is addicted to one or more drugs, one or more types of alcohol, or a combination thereof.

In one embodiment, a pharmaceutical composition that comprises digestive enzymes is formed into a dosage formulation containing a therapeutically effective amount of one or more proteases, one or more amylases, one or more lipases, or a combination thereof. In one non-limiting instance, the one or more proteases comprise chymotrypsin, trypsin, or a combination of chymotrypsin and trypsin.

In another embodiment, a pharmaceutical composition to be administered to a subject comprises a protease, an amylase and a lipase. In one non-limiting instance, the protease comprises chymotrypsin, trypsin, or a combination of chymotrypsin and trypsin.

The nature of the human digestive tract creates challenges for the delivery of digestive enzymes to patients with addictions to treatment with digestive enzymes. Multiple temperature and pH changes over the course of the digestive tract make specific delivery a necessity and a challenge. For instance, pH as low as 1 is encountered in the stomach, but rapidly increases to a more basic pH of 5-6 in the proximal small intestine. For example, generally the pH in the stomach is approximately 1.2, the pH in the duodenum is about 5.0 to 6.0; the pH in the jejunum is about 6.8, and the pH is about 7.2 in the proximal ileum and about 7.5 in the distal ileum. The low pH in the stomach which changes rapidly to a more basic pH of 5-6 in the proximal small intestines, call for a specific delivery method depending upon where the enzyme is to be delivered.

Delivery of digestive enzymes can also be challenging due to the rapid degradation and denaturing of enzymes at ambient room temperature, as well as the enhanced degradation and denaturing that can occur with high temperature, pressure, humidity and/or exposure to light. Moisture and heat together can quickly destabilize enzymes, reducing their effectiveness, and shortening shelf life, leading to inaccurate dosing. Denaturation or destabilization of the enzymes can reduce their effectiveness by reducing the dose of active enzymes to less than the amount needed for effective treatment. Alternatively, attempting to compensate for the denaturation or destabilization by increasing the dose to ensure an effective level of active enzyme, could risk an overdose or overfilling a capsule or other dosage form.

In one embodiment, the present invention includes digestive enzymes. In one instance, the digestive enzymes comprise a protease, an amylase, a lipase, or a combination thereof. In one non-limiting example, the digestive enzymes comprise one or more proteases, one or more amylases, and one or more lipases. In another non-limiting example, the digestive enzymes comprise a protease, an amylase, and a lipase. In certain instances, a pharmaceutical composition that comprises the digestive enzymes further comprises one or more enzymes selected from the group consisting of a sucrase, a cellulase, a maltase, papain, papaya, bromelain, or a combination thereof. In other instances, where a pharmaceutical composition comprises one or more proteases, the one or more proteases can be, for example, chymotrypsin, trypsin, bromelain, or a combination thereof. In one non-limiting embodiment, a pharmaceutical composition that comprises the digestive enzymes comprises a mixture of proteases such as, for example, a mixture of chymotrypsin and trypsin. In one non-limiting instance, digestive enzymes in a pharmaceutical composition can be provided as, for example, pancreatin. Such digestive enzymes can be provided as a crystalline form of pancreatin or as a solid form of pancreatin.

The digestive enzymes to be used in pharmaceutical compositions described herein can be animal enzymes, plant enzymes, microbial enzymes, synthetic enzymes, or a combination thereof. When the digestive enzymes are animal enzymes, they can be, in some instances, obtained from a mammal such as, for example, a pig pancreas. When the digestive enzymes are microbial enzymes, they can be, for example, fungal enzymes or enzymes from yeast. The digestive enzyme used in the present invention can be any combination of digestive enzymes of a type produced by the pancreas, including, but not limited to digestive enzymes from a pancreatic source or other sources. The scope of the invention is not limited to pancreatic enzymes of porcine origin. The enzyme may include one or more enzymes, and can also be plant derived, synthetically derived, recombinantly produced in microbial, yeast, or mammalian cells, and can include a mixture of enzymes from one or more sources. Digestive enzymes, can include, for example, enzymes from more or more sources mixed together. This includes, for example, the addition of single digestive enzymes to digestive enzymes derived from pancreatic sources in order to provide appropriate levels of specific digestive enzymes that provide more effective treatment for an addiction.

In one aspect, digestive enzymes described herein can be coated with an enteric coating. Enteric coatings include, for example, hypromellose phthalate, dimethicone 1000, dibutyl phthalate, or a combination thereof. A non-limiting example of an enteric coating for use herein includes, for example, ULTRASE®.

In other aspects, pharmaceutical compositions comprising coated digestive enzyme particles. These coated digestive enzyme particles contain a core that comprise digestive enzymes, and a coating that comprises a lipid. To protect and stabilize the digestive enzyme from unfavorable conditions such as penetration and decomposition, the digestive enzymes can be coated with an appropriate lipid or an appropriate blend of lipids.

In some aspects, a lipid coating comprises primarily one lipid. On other aspects, a lipid coating comprises a blend of lipids. Coated digestive enzyme compositions can, in some instances, exhibit improved (i.e., lengthened) shelf life in storage. The coatings in the digestive enzyme preparations create a barrier to degradation and denaturation, and allow more accurate levels of active enzymes to reach the treated individuals. The lipid coating of this invention provides a significant barrier to moisture, heat, humidity and exposure to light by allowing for a physical barrier as well as one that prevents and or reduces hydrolysis. The coated enzyme preparations undergo less hydrolysis as a result of protection from moisture in the environment by the lipid coating. As a result of the present invention, digestive enzymes are provided which can tolerate storage conditions (e.g., moisture, heat, oxygen, etc.) for long periods of time thus enabling extended shelf life. The coating of the digestive enzymes protects the enzyme from the environment.

It is a challenge to make digestive enzyme compositions that avoid the use of allergens, and other carriers, excipients, extenders, colorants, etc. that could potentially cause adverse symptoms or morbidity of subjects being treated. Furthermore, in very young children, administration of a composition with ease and tolerability is paramount.

It is another aspect of the present invention to prepare coated digestive enzyme particles without the use of extenders colorants, dyes, flow enhancers and other additives to reduce the potential for allergens and other sensitivity reactions. Surprisingly digestive enzyme particles containing lipases can be successfully with coating consisting essentially of only hydrogenated soy oil.

In addition, porcine digestive enzymes possess a significant odor and taste, similar to cured/smoked pork. This taste can be strong and offensive to some individuals taking enzyme replacement, and especially to children. The addition of a lipid coating provides significant taste masking to the enzyme preparation, which allows for the tolerance of taste, as the lipid coating is odorless and tasteless. The use of this method of taste masking which does not involve the use of color, dyes, perfumes, recipients, or other substances is preferable for the administration of medications, which have an unpleasant or undesirable taste and odor. In other embodiments, coated digestive enzyme preparations with improved taste and smell are prepared.

In some non-limiting instances, the coatings on the digestive enzyme particle cores can be continuous. By "continuous", it is meant that the digestive enzymes are, generally, uniformly protected by the coating. The coating provides protection of the digestive enzymes from conditions such as moisture, temperature, and conditions encountered during storage.

In addition, the coating also provides controlled release of the digestive enzymes. The emulsification properties of the coating allows for controlled release of the digestive enzymes in the gastrointestinal system, preferably the region of the GI tract where the digestive enzymes are to be utilized. The coating protects the digestive enzymes from the environment and provides emulsification without detracting from the abrasion resistance of the coating. For example, for conditions requiring treatment with proteases, the release of the protease portion of the digestive enzymes is necessary in the proximal small intestine, thereby necessitating a lipid encapsulation which has a dissolution profile between 30-90 minutes. The dissolution profile may also be about 30, about 35, about 40, about 45, about 50, about 55, about 60, about 65, about 70, about 75, about 80, about 85 or about 90 minutes. Dissolution profiles may be obtained using methods and conditions known to those of skill in the art. For example, dissolution profiles can be determined at various pH's, including a pH of about 1, about 2, about 3, about 4, about 5, about 6, about 7, about 8, about 9, and about 10.

The rate of release of the digestive enzymes can also be controlled by additives as described below. When the preparations are exposed to a solvent, the solvent interacts with the mollifiable lipid in the coating and results in emulsification of the coating and release of the digestive enzymes.

The lipid to be used in the coating is any lipid, lipid mixture, or a blend of lipids and emulsifiers which emulsifies when exposed to a solvent, and has a melting point which allows the lipid to be a solid at typical storage temperatures. The lipid can be a vegetable or animal derived-lipid. In some embodiments, the lipid consists essentially of, or comprises one or more monoglycerides, diglycerides or triglycerides, or other components including, for example, emulsifiers found in hydrogenated vegetable oils. In another embodiment the lipid is a non-polar lipid.

As used herein, animal and/or vegetable "derived" lipids can include fats and oils originating from plant or animal sources and/or tissues, and/or synthetically produced based on the structures of fats and oils originating from plant or animal sources. Lipid material may be refined, extracted or purified by known chemical or mechanical processes. Certain fatty acids present in lipids, termed essential fatty acids, must be present in the mammalian diet. The lipid may, in some embodiments, comprise a Type I USP-National Formulary vegetable oil.

The coated digestive enzyme particles include, in some instances, digestive enzyme particles where about 90% of the particles are between about #40 and #140 USSS mesh in size, or from about 105 µm to about 425 µm in size. The coated digestive enzyme particles include, in some instances, digestive enzyme particles where about 75% of the particles are between about #40 and #80 USSS mesh in size, or from about 180 µm to about 425 µm in size. Particles between #40 and #140 USSS mesh in size pass through #40 mesh, but do not pass through #140 mesh.

The lipid coating reduces the aerosolization of the digestive enzymes that may be caustic to a child if inhaled through the lungs or the nose. In another embodiment, provided herein are methods of delivering coated digestive enzymes with improved safety of administration by reducing the amount of aerosolization of the digestive enzymes. The lipid coating reduces aerosolization and the potential for caustic burn, aspiration, and/or aspiration pneumonias in children and administrators of the digestive enzymes, thereby reducing the potential for illness in immune compromised children and leading to safer administration.

As used herein, the term "non-aerosolizable" will be used to refer to coated digestive enzyme particles where substantially all of the particles are large enough to eliminate or reduce aerosolization upon pouring of the coated digestive enzyme particles compared to uncoated digestive enzymes. For example, the term "non-aerosolizable" may refer to coated digestive enzyme particles where at least about 90% of the particles are between about #40 USSS mesh and #140 USSS mesh in size, or from about 106 μm to about 425 μm in size.

The term "non-aerosolizable" may also refer to coated digestive enzyme particles where at least about where at least about 75% of the particles are between about #40 and #80 mesh, or about 180 μm to 425 μm in size. The size distribution of particles in an exemplary raw enzyme preparation can vary. Large particles (>40 mesh) and very small particles (<140 mesh) are generally not suitable for proper encapsulation and can be removed by screening. Screening of the particles may include quality control steps to improve the activity, appearance or particle size of the digestive enzyme. For example, the particles may be analyzed to determine enzyme activity content, and/or visualized using chromatographic, microscopic or other analytical methods. The particles may also be screened to obtain particles of a suitable size for encapsulation by removing particles that are too fine or too large. For example, the particles may be sieved to obtain particles of a suitable size or more uniform size range for encapsulation. As a further example, the particles may be sieved through #40 USSS mesh and through USSS #140 USSS mesh. Particles that pass through the #40 USSS mesh but are retained by the #140 USSS mesh are of an appropriate size range for coating or encapsulation Particles may also be screened by sieving through USSS #140, #120, #100, #80, #70, #60, #50, #45, or #40 mesh, or any combination thereof.

In some embodiments, less than about 35, 30, 25, 20, 15 or 10% of the coated particles can be sieved through #100 USSS mesh (i.e., be about 150 μm in size). In other embodiments, less than about 20% of the coated particles can be sieved through #100 USS mesh (i.e., be about 150 μm in size). In other embodiments, or less than about 15% of the coated particles can be sieved through #100 USS mesh (i.e., be about 150 μm in size).

The amount of digestive enzymes present in the coated particles can be an amount of from about 65% to about 95% by weight. In some embodiments, the digestive enzymes can be present in the coated particles in an amount of from 70% to about 90% by weight. In other embodiments, the digestive enzymes can be present in the coated particles in an amount of from about 67.5% to about 87.5% by weight. In other embodiments, the digestive enzymes can be present in the coated particles in an amount of from about 75% to about 85% by weight. In other embodiments, the digestive enzymes can be present in the coated particles in an amount of from about 77.5% to about 82.5% by weight. In other embodiments, the amount of digestive enzymes present in the coated particles is about 65%, about 67.5%, about 70%, about 72.5%, about 75%, about 77.5%, about 80%, about 82.5%, about 85%, about 87.5%, about 90%, about 92.5%, or about 95% by weight, or anywhere in between.

In some embodiments, the pharmaceutical composition comprises at least one protease and at least one lipase, wherein the ratio of total protease to total lipase in U.S.P. units ranges from about 4:1 to about 20:1 including 4:1, 5:1, 5.371:1, 6:1, 7:1, 8:1, 9:1, 10:1, 11:1, 12:1, 13:1, 14:1, 15:1, 16:1, 17:1, 18:1, 19:1 and 20:1, along with all values in-between.

In some embodiments, the ratio of protease to lipase ranges from about 4:1 to about 10:1 including 4:1, 5:1, 5.371:1, 6:1, 7:1, 8:1, 9:1, and 10:1, along with all values in-between.

In yet another embodiment, the pharmaceutical composition comprises at least one protease and at least one lipase, wherein the ratio of total protease to total lipase in U.S.P. units/dose ranges from about 5.371:1 to about 20:1 including 5.371:1, 6:1, 7.1, 8.1, 9:1, 10:1, 11:1, 12:1, 13:1, 14:1, 15:1, 16:1, 17:1, 18:1, 19:1, and 20:1, along with all values in-between.

In another embodiment, the pharmaceutical composition comprises at least one protease and at least one lipase, wherein the ratio of total protease to total lipase in U.S.P. units/dose ranges from about 1:1 to about 20:1.

In yet another embodiment, the ratio of protease to lipase ranges from about 4:1 to about 10:1.

In one embodiment, the ratio of protease to lipase ranges from about 5.371:1 to about 10:1 including 5.371:1, 6:1, 7:1, 8:1, 9:1, and 10:1 along with all values in-between.

In one embodiment, the pharmaceutical composition comprises at least one protease and at least one amylase, wherein the ratio of total protease to total amylase in U.S.P. units/dose ranges from about 1:0.1 to about 1:10 including 1:0.25, 1:0.5, 1:0.75, 1:1, 1:1.25, 1:1.5, 1:1.75:1:2, 1:1.25, 1:1.5, 1:1.75, 1:1.2, 1:1.25, 1:1.5, 1:1.75, 1:1.2, 1:1.25, 1:1.5, 1:1.75, 1:1.2:1:1.5, 1:2, 1:3, 1:4, 1:5, 1:6, 1:7, 1:8, 1.9 and 1:10 along with all values in-between.

A pharmaceutical composition which contains the coated digestive enzyme particles can be delivered as a sprinkle, powder, capsule, tablet, pellet, caplet or other form. Allowing for specific unit dosing of coated digestive enzyme particles maintains the enzyme activity within specific stability parameters. In one non-limiting instance, the coated digestive enzyme particles are housed in a blister pack, a trilaminar foil pouch, or a similar barrier to keep out moisture and to protect the digestive enzymes from adverse environmental factors.

A pharmaceutical composition described herein can, in one instance, comprise digestive enzymes as the active ingredient. A pharmaceutical composition described herein can, in another instance, consist essentially of digestive enzymes as the active ingredient. A pharmaceutical composition described herein can, in another instance, comprise digestive enzymes as the active ingredient.

As used herein, "consisting essentially of" or "consists essentially of" means that the pharmaceutical composition does not contain one or more additional active ingredients, but may contain one or more inert additives, excipients, carriers, etc. as described in more detail below.

In one instance, one or more additives can be blended with the lipid(s) in the coating. Selection of the lipid(s) and additives can help control the rate of release of the digestive enzymes from the pharmaceutical composition. A lipid coat can be chosen to release the digestive enzymes in the area of the digestive tract to optimize treatment. In one non-limiting example, the digestive enzymes can be formulated with a lipid coating to optimize delivery to the proximal small intestines.

The pharmaceutical composition can be administered in a sachet or pouch preparation for ease of delivery to children and adults. In some embodiments, described herein are methods of administration of coated digestive enzyme particles, housed in a sachet or pouch. This facilitates administration, including but not limited to, administration in a food or a drink, via direct administration into the oral cavity, or via administration directly into the GI system through an NG-tube, G-tube or other GI entrances or deliveries.

In some embodiments, a dose of a pharmaceutical composition to be administered to a subject contains from about 100 mg to about 9000 mg (i.e., mg/dose) of the digestive enzymes. That is, each dose may contain about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 2000 mg, about 2050 mg, about 2100 mg, about 2150 mg, about 2200 mg, about 2250 mg, about 2300 mg, about 2350 mg, about 2400 mg, about 2450 mg, about 2500 mg, about 2550 mg, about 2600 mg, about 2650 mg, about 2700 mg, about 2750 mg, about 2800 mg, about 2850 mg, about 2900 mg, about 2950 mg, about 3000 mg, about 3050 mg, about 3100 mg, about 3150 mg, about 3200 mg, about 3250 mg, about 3300 mg, about 3350 mg, about 3400 mg, about 3450 mg, about 3500 mg, about 3550 mg, about 3600 mg, about 3650 mg, about 3700 mg, about 3750 mg, about 3800 mg, about 3850 mg, about 3900 mg, about 3950 mg, about 4000 mg, about 4050 mg, about 4100 mg, about 4150 mg, about 4200 mg, about 4250 mg, about 4300 mg, about 4350 mg, about 4400 mg, about 4450 mg, about 4500 mg, about 4550 mg, about 4600 mg, about 4650 mg, about 4700 mg, about 4750 mg, about 4800 mg, about 4850 mg, about 4900 mg, about 4950 mg, about 5000 mg, about 5050 mg, about 5100 mg, about 5150 mg, about 5200 mg, about 5250 mg, about 5300 mg, about 5350 mg, about 5400 mg, about 5450 mg, about 5500 mg, about 5550 mg, about 5600 mg, about 5650 mg, about 5700 mg, about 5750 mg, about 5800 mg, about 5850 mg, about 5900 mg, about 5950 mg, about 6000 mg, about 6050 mg, about 6100 mg, about 6150 mg, about 6200 mg, about 6250 mg, about 6300 mg, about 6350 mg, about 6400 mg, about 6450 mg, about 6500 mg, about 6550 mg, about 6600 mg, about 6650 mg, about 6700 mg, about 6750 mg, about 6800 mg, about 6850 mg, about 6900 mg, about 6950 mg, about 7000 mg, about 7050 mg, about 7100 mg, about 7150 mg, about 7200 mg, about 7250 mg, about 7300 mg, about 7350 mg, about 7400 mg, about 7450 mg, about 7500 mg, about 7550 mg, about 7600 mg, about 7650 mg, about 7700 mg, about 7750 mg, about 7800 mg, about 7850 mg, about 7900 mg, about 7950 mg, about 8000 mg, about 8050 mg, about 8100 mg, about 8150 mg, about 8200 mg, about 8250 mg, about 8300 mg, about 8350 mg, about 8400 mg, about 8450 mg, about 8500 mg, about 8550 mg, about 8600 mg, about 8650 mg, about 8700 mg, about 8750 mg, about 8800 mg, about 8850 mg, about 8900 mg, about 8950 mg, or about 9000 mg of the digestive enzymes.

In one non-limiting example, a pharmaceutical composition comprises coated digestive enzyme particles that are encapsulated, and the capsule comprises about 900 mg of the digestive enzymes. A subject may be administered 3, 4, 5, 6, 7, 8, 9, 10, 11 or 12 capsules at one time depending upon the age, weight, severity of the addiction, and/or general health of the subject.

For explanation purposes only, in one non-limiting example, a subject can be administered 5 capsules with breakfast and each capsule comprises about 900 mg of digestive enzymes. In such an administration, the subject will be administered about 4,500 mg of digestive enzymes.

The protease activity of a dose of a pharmaceutical composition described herein can be an amount such as, for example, not less than about 100 U.S.P. Units/mg, about 105 U.S.P. Units/mg, about 110 U.S.P. Units/mg, about 115 U.S.P. Units/mg, about 120 U.S.P. Units/mg, about 125 U.S.P. Units/mg, about 130 U.S.P. Units/mg, about 135 U.S.P. Units/mg, about 140 U.S.P. Units/mg, about 145 U.S.P. Units/mg, about 150 U.S.P. Units/mg, about 155 U.S.P. Units/mg, about 160 U.S.P. Units/mg, about 165 U.S.P. Units/mg, about 170 U.S.P. Units/mg, about 175 U.S.P. Units/mg, about 180 U.S.P. Units/mg, about 185 U.S.P. Units/mg, about 190 U.S.P. Units/mg, about 195 U.S.P. Units/mg, or about 200 U.S.P. Units/mg.

In one instance, the amylase is present in the pharmaceutical composition in an amount of from about 120,000 to about 370,000 U.S.P. units/unit dose.

In one instance, the protease is present in the pharmaceutical composition in an amount of from about 130,000 to about 165,000 U.S.P. units/unit dose.

In one instance, the lipase is present in the pharmaceutical composition in an amount of from about 17,000 to about 60,000 U.S.P. units/unit dose.

For explanation purposes only, in one non-limiting example, a subject can be administered 8 capsules with lunch and each capsule comprises about digestive enzymes having a protease activity of from about 130,000 U.S.P. Units to about 150,000 U.S.P. Units of protease activity. In such an administration, the subject will be administered about 4,500 mg of digestive enzymes.

The term "unit dose" when used in reference to a pharmaceutical composition refers to physically distinct units suitable as unitary dosage for subjects, each unit containing a predetermined quantity of active material calculated to produce the desired therapeutic effect in association with the required diluent; i.e., carrier, or vehicle.

In some instances, one, two, three, four, five, six, seven, eight, nine, or more doses or more of a pharmaceutical composition can be administered to a subject daily.

In other instances, a subject may be administered one or more doses of a pharmaceutical composition once, twice, three times, four times, or more daily.

In one non-limiting example, a subject is administered from about 4 to about 10 capsules with breakfast, from about 4 to about 10 capsules with lunch and from about 4 to about 10 capsules with dinner.

A practitioner can empirically determine the dose of the pharmaceutical composition to be administered to a subject depending upon, for example, the height, weight, age, severity of addiction, length of addiction, etc. A subject may receive treatment for about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25 weeks, about 26 weeks, about 27 weeks, about 28 weeks, about 29 weeks, about 30 weeks or more weeks. A subject may receive treatment for about 5 days, about 10 days, about 15 days, about 20 days, about 25 days, 30 days, about 35 days, about 40 days, about 45 days, 50 days, about 55 days, about 60 days, about 65 days, 70 days, about 75 days, about 80 days, about 85 days, about 90 days, about 95 days, about 100 days, about 105 days or more. It will be understood that a subject having received treatment and no longer showing or feeling one or more signs of the addiction can be administered one or more treatments if relapse occurs.

It will be understood that if a subject is highly addicted to one or more substances, the subject can be administered higher doses of the pharmaceutical composition. Alternatively, if a subject is only mildly addicted to one or more substances, the subject can be administered lower doses of the pharmaceutical composition. A subject may receive increased or decreased doses of the pharmaceutical composition as throughout their treatment depending upon how they react to the pharmaceutical composition.

In some embodiments, the invention relates to the administration of coated digestive enzyme particles, housed in a sachet which allows for particular types of administration including but not limited to administration in food, drink, or direct administration into the oral cavity or directly into the GI system through a NG-tube, G-tube or other GI entrances.

The sachet can represent a single unit dose or a multiple unit dose. The trilaminar foil allows the coated digestive enzyme particles to remain stable during storage and allows for ease of administration.

In other embodiments, the invention relates to coated digestive enzyme particles that are encapsulated and stored in moisture resistant blister packs or foil-sealed moisture resistant bottles. Appropriate foil-sealed moisture resistant bottles are known in the art and include, for example, glass bottles, high density polyethylene (HTPE) plastic bottles or other appropriate type of glass and plastic bottles that can be sealed with foil. In one non-limiting example, capsules are stored in a sachet. Pharmaceutical compositions described herein are packaged, in certain instances, under low humidity conditions. As used herein, "low humidity conditions" refer to packaging in less than or equal to 15% relative humidity. It would be understood that an appropriate pharmaceutical-grade desiccant can also be packaged, in some instances, with the product to extend shelf life during storage.

Pharmaceutical compositions described herein, in some instances, can include not only one or more digestive enzymes, but also one or more carriers, one or more excipients, one or more buffers, one or more fillers, one or more binders, one or more preservatives, one or more antioxidants, one or more alkyl parabens, one or more proteins, one or more sugars, one or more chelating agents, one or more sugars, one or more surfactants, one or more salt-forming counter ions, one or more stabilizers, one or more surfactants, one or more diluents, one or more sweeteners, one or more salts, one or more taste maskers, etc. Acceptable carriers, excipients, or stabilizers are those that are non-toxic to recipients at the dosages and concentrations employed, and include buffers such as phosphate, histidine, acetate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin or gelatin; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® and/or polyethylene glycol (PEG). In some instances, the coated digestive enzyme particles are prepared in microcrystalline cellulose.

Acceptable carriers are physiologically acceptable to the administered subject and retain the therapeutic properties of the compounds with/in which it is administered. Acceptable carriers and their formulations are and generally described in, for example, Remington' pharmaceutical Sciences (18th Edition, Ed., A. Gennaro, Mack Publishing Co., Easton, PA 1990). One exemplary carrier is physiological saline.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject compounds from the administration site of one organ, or portion of the body, to another organ, or portion of the body, or in an in vitro assay system. Each carrier is acceptable in the sense of being compatible with the other ingredients of the formulation and not injurious to a subject to whom it is administered. Nor should an acceptable carrier alter the specific activity of the active agents in the pharmaceutical composition.

In one aspect, provided herein are pharmaceutically acceptable or physiologically acceptable compositions including solvents (aqueous or non-aqueous), solutions, emulsions, dispersion media, coatings, isotonic and absorption promoting or delaying agents, compatible with administration to a human subject.

Another embodiment of the invention relates to the improvement of delivery of enzymes to humans by reducing the use of excipients, extenders and solvents currently used in the preparations for delivery of digestive enzymes to humans. For example, preparation pharmaceutical composition may contain only one excipient, which increases the safety of administration by decreasing the chance of an allergic response.

In some embodiments, the lipid coating does not require the digestive enzymes to be treated with solvents, extenders and excipients to facilitate flow or improve stability of the coated particles. In one aspect, provided herein is a "clean" preparation of GRAS substances (generally regarded as safe) to be administered. The reduction in the use of solvents, extenders excipients and other additives reduces the exposure of the subjects taking the pharmaceutical compositions to potential allergens, thereby producing a hypoallergenic composition that further enhances its potential uses in the treatment of subjects who might otherwise develop an allergic response to treatment. Administration of the coated digestive enzyme particles described herein can, thus, reduce exposure to potentially toxic substances and will also reduce the possibility of allergy formation. Accordingly, in some embodiments, the pharmaceutical compositions described herein are hypoallergenic.

Coated digestive enzyme particles supplied by an API supplier may be provided as irregular shaped, and multi-sized particles, with uneven edges, and much clumping, and containing some crystalline salt particles. Uneven particle size and shape reduces flow properties, and interferes with packaging. Pouring uncoated enzyme into the mouth of an individual would be difficult, and potentially may cause too much or too little of the enzyme to be delivered. The coated digestive enzyme particles described herein provide a non-dusty, free-flowing particulate preparation suitable for sachet packaging and for pouring onto food or drink. In addition, the coating helps prevent aerosolization, and therefore increase safety, and to increase flow properties which enhance manufacturing of a pharmaceutical composition to be administered in the described methods.

The lipid can be present in the coated particles in an amount of about 15%, about 16%, about 16.5%, about 17%, about 17.5%, about 18%, about 18.5%, about 19%, about 19.5%, about 20%, about 20.5%, about 21%, about 21.5%, about 22%, about 22.5%, about 23%, about 24% or about 25% by weight.

"Lipids" as used herein means those lipids which contain at least one hydrophilic group and at least one hydrophobic group, and have a structure capable of forming a hydrophilic and hydrophobic interface. These chemical and/or physical properties, mentioned above, of a lipid permit emulsification. Examples of interfaces include, for example, micelles and bilayers. The hydrophilic group can be a polar group and can be charged or uncharged.

The lipid can be derived from animal origins or vegetable origins, such as, for example, palm kernel oil, soybean oil, cottonseed oil, canola oil, and poultry fat, including hydrogenated type I vegetable oils. In some embodiments, the lipid is hydrogenated. The lipid can also be saturated or partially saturated. Examples of lipids include, but are not limited to, monoglycerides, diglycerides, triglycerides, fatty acids, esters of fatty acids, phospholipids, salts thereof, and combinations thereof. In one non-limiting instance, the lipid coating comprises monoglycerides, diglycerides, triglycerides, or a combination thereof. In another non-limiting instance, the lipid coating comprises a combination of monoglycerides and diglycerides. In another non-limiting instance, the lipid coating comprises a combination of diglycerides and triglycerides. In another non-limiting instance, the lipid coating comprises a combination of monoglycerides, diglycerides and triglycerides.

The lipid may be, in some instances, a "food grade lipid". Examples of food grade lipids include, but are not limited to, sorbitan monostearates, sorbitan tristearates, and calcium stearoyl lactylates. Other examples of food grade fatty acid esters which are lipids include acetic acid esters of mono- and diglycerides, citric acid esters of mono- and di-glycerides, lactic acid esters of mono- and di-glycerides, polyglycerol esters of fatty acids, propylene glycol esters of fatty acids, and diacetyl tartaric acid esters of mono- and diglycerides. In one non-limiting example, a lipid coating comprises a hydrogenated soy oil.

The lipid may also be, in some instances, a pharmaceutical grade lipid. Pharmaceutical grade lipids include, but are not limited to, highly purified lipid from which all protein antigens have been removed. Such lipids are beneficial in that they do not induce allergic responses and do not include cis or trans fatty acids. One non-limiting example of a pharmaceutical grade lipid comprises a soybean oil that is fully hydrogenated.

In some instances, a lipid coating will produce non-agglomerating, non-aerosolizing digestive enzyme particles.

The inclusion of one or more additives with a lipid can be used to control emulsification or dissolution of the coating and release of the digestive enzymes. For example, a triglyceride, can be blended with a monoglycerides to control emulsification or dissolution of the coating and thus control (e.g., decrease) the rate of release of the digestive enzymes from the coated particles. As a further example, a diglyceride and a triglyceride can be blended with a monoglyceride to control the rate of release of the digestive enzymes. Hydrogenated vegetable oils may contain emulsifying agents, such as soy lecithin or other components.

Properties including mechanical strength, melting point, and hydrophobicity can be considered when choosing a suitable lipid coating for the digestive enzymes. Lipids having lower melting points or more polar, hydrophilic properties are generally less suitable for the coating because they may result in a product that would cake under accelerated storage stability conditions. Coated digestive enzyme particles made using, for example, hydrogenated soy oil (e.g., partially or fully hydrogenated), hydrogenated castor wax, and carnauba wax all demonstrated good pouring and no caking.

The wax can be paraffin wax; a petroleum wax; a mineral wax such as ozokerite, ceresin, or montan wax; a vegetable wax such as, for example, carnauba wax, bayberry wax or flax wax; an animal wax such as, for example, spermaceti; or an insect wax such as beeswax.

Additionally, the wax material can be an ester of a fatty acid having 12 to 31 carbon atoms and a fatty alcohol having 12 to 31 carbon atoms, the ester having from a carbon atom content of from 24 to 62, or a mixture thereof Examples include myricyl palmitate, cetyl palmitate, myricyl cerotate, cetyl myristate, ceryl palmitate, ceryl certate, myricyl melissate, stearyl palmitate, stearyl myristate, and lauryl laurate.

"Encapsulate" as used herein, means that the coated digestive enzyme particles are packaged in an appropriate capsule material. Appropriate capsule materials are known in the art and are contemplated for use herein.

A non-limiting exemplary dosage form is a capsule in which the coated digestive enzyme particles are packaged in an appropriate material to be delivered as a capsule dosage form. A capsule, as described herein, includes soft or hard capsules, e.g., capsules made from animal-derived gelatin or plant-derived Hydroxypropylmethyl cellulose (HPMC), or "sprinkle capsules"). Exemplary capsules include, but are not limited to, HPMC capsules from CAPSUGEL®. As used herein, hydroxypropyl methylcellulose includes, but is not limited to, HPMC K100, HPMC K4M, HPMC K15M, and HPMC K100M.

In some embodiments, a dosage form comprises a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) solid dispersion, solid solution, bioerodible dosage form, controlled release formulations, pulsatile release dosage forms, multiparticulate dosage forms. In other embodiments, the pharmaceutical formulation is in the form of a powder. In still other embodiments, the pharmaceutical formulation is in the form of a tablet, including but not limited to, a fast-melt tablet.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In one non-limiting embodiment, a capsule may be prepared, for example, by placing the composition described above, inside of a capsule. In some embodiments, the composition is placed in a soft gelatin capsule. In other embodiments, the composition is placed in standard gelatin capsules or non-gelatin capsules such as capsules comprising HPMC. In other embodiments, the composition is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the composition is delivered in a capsule form.

A non-limiting exemplary route of administration comprises oral administration of a composition described herein. Pharmaceutical compositions can be administered as a single capsule or in multiple capsule dosage form. In some embodiments, the pharmaceutical formulation is administered in two, or three, four, five, six, seven, eight, nine, ten, eleven, twelve, thirteen or fourteen capsules or tablets at each time of administration.

One non-limiting exemplary dosing regimen includes, for example, administration of from about 4 to about 9 capsules, or from about 5 to about 8 capsules with each meal daily for at least 12 weeks. Another non-limiting exemplary dosing regimen includes, for example, administration of from about 4 to about 9 capsules, or from about 5 to about 8 capsules with each meal daily for at least 24 weeks. Another non-limiting exemplary dosing regimen includes, for example, administration of from about 4 to about 9 capsules, or from about 5 to about 8 capsules with each meal daily for at least 30 weeks.

A composition described herein includes, in one instance, a lipid-encapsulated pancreatic enzyme concentrate (PEC) that comprises one or more proteases, one or more lipases and one or more amylases, designed to release chymotrypsin and other proteases in the proximal small intestine without extreme degradation by stomach acid.

In one instance, the composition comprises a protease, wherein the protease comprises chymotrypsin. Chymotrypsin is a serine protease enzyme and one of the prominent proteases involved in human digestion. Emerging evidence demonstrates that amino acids, which are the by-product of protein digestion, are not only involved in protein synthesis but also play a significant role in other important neurological functions. Of those essential amino acids cleaved by chymotrypsin, phenylalanine and tryptophan are necessary components of the body's synthesis of dopamine and serotonin respectively. Chymotrypsin is unique because it cleaves proteins at the sites proximal to four essential amino acids. See, FIG. 1.

There is an emergence of evidence with respect to cocaine addiction and the role of ΔFosβ that builds up in the brains of cocaine addicts that causes an elongation of and proliferation of dendritic spines. These dendritic spines may be associated with the persistence of cravings in subjects that are addicted to one or more substances.

Compositions as described herein cleave phenylalanine from endogenous proteins that are ingested. Its administration may hasten the buildup of phenylalanine and hence replenish the depleted dopamine stores. This allows for the synthesis of new dopamine. Further, the presence of additional phenylalanine may drive the reduction of the elongated dendritic spines, and therefore reduce the cravings for cocaine, or another drug or alcohol.

A composition described herein a high protease, lipid-encapsulated, pancreatic enzyme concentrate (PEC) designed to release chymotrypsin and other proteases in the proximal small intestine without extreme degradation by stomach acid. It is a formulation that allows high protease delivery without a classic enteric coating and is designed to deliver enzyme to the proximal small intestine (duodenum). This formulation allows for maximal delivery of proteases into the proximal small intestines where protease delivery and subsequent protein hydrolysis and peptide absorption is best optimized.

The pharmaceutical compositions described herein are suited for use in delivering digestive enzymes to subjects having one or more symptoms of addiction to one or more substances. The pharmaceutical compositions described herein are suited for use in delivering digestive enzymes to treat a subject addicted to one or more substances.

Treating", as used herein, refers to partial or complete reduction of one or more symptoms of addiction to one or more substances. In some instances, treatment can be assessed using conventional means in the art for measuring the severity of a symptom, for example, how strong a craving is for an addicted substance, other symptoms. In another embodiment, treatment can be assessed by quantitatively measuring a level of ΔFosβ from a sample obtained from a subject and comparing the level of ΔFosβ in the sample to a level of ΔFosβ from a healthy (non-addicted) subject. Methods for measuring ΔFosβ include, but are not limited to, an Enzyme Linked Immunosorbant Assay (ELISA).

Pancreatin and Pancrealipase

There are two types of pancreatic enzymes which have United States Pharmacopeia (U.S.P.) designations: pancreatin and pancrealipase. "Pancreatin" is a substance containing enzymes, principally amylase, lipase, and protease, obtained from the pancreas of the hog *Sus scrofa* Linne var. *domesticus* Gray (Fam. Suidae) or of the ox *Bos taurus* Linne (Fam. Bocidae). Pancreatin contains, in each mg, not less than 25 U.S.P. units of amylase activity, not less than 2 U.S.P. units of lipase activity, and not less than 25 U.S.P. of protease activity. Pancreatin of a higher digestive power may be labeled as a whole-number multiple of the three minimum activities or may be diluted by admixture with lactose, or with sucrose containing not more than 3.25 percent of starch, or with pancreatin of a lower digestive power. Pancreatin can be provided as a crystalline substance.

In contrast, pancrealipase refers to a cream-colored, amorphous powder, having a faint, characteristic meaty odor, which contains lipase in an amount of not less than 24 U.S.P. Units/mg; protease in an amount of not less than 100 U.S.P. Units/mg; and amylase in an amount of not less than 100 U.S.P. Units/mg; with not more than 5% fat and not more than 5% loss on drying. CREON® is a form of pancrealipase that is sold as formulations of (i) 3,000 Units of a lipase, 9,500 Units of a protease, 15,000 Units of an amylase; (ii) 6,000 Units of a lipase, 19,000 Units of a protease, 30,000 Units of an amylase; (iii) 12,000 Units of a lipase, 38,000 Units of a protease, 60,000 Units of an amylase; (iv) 24,000 Units of a lipase, 76,000 Units of a protease, and 120,000 Units of an amylase; or (v) 36,000 Units of a lipase, 114,000 Units of a protease, and 180,000 Units of an amylase. CREON® formulations are known to be irritating to mucosa of a subject and also is known to cause the following adverse side effects: Abdominal pain, abnormal feces, cough, dizziness, flatulence, headache, weight decreased; hyperuricemia, fibrosing colonopathy (with high doses), and/or allergic reactions.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application.

Example 1

Proposed Indication

The compositions and method described are for treatment of an addiction. For example, administration of the pharmaceutical composition can treat a craving, impulsivity, lack of impulse control, or a combination thereof, of the addiction. The present example describes treatment of cravings, impulsivity, and lack of impulse control in active cocaine-addicted users.

Figure 3:
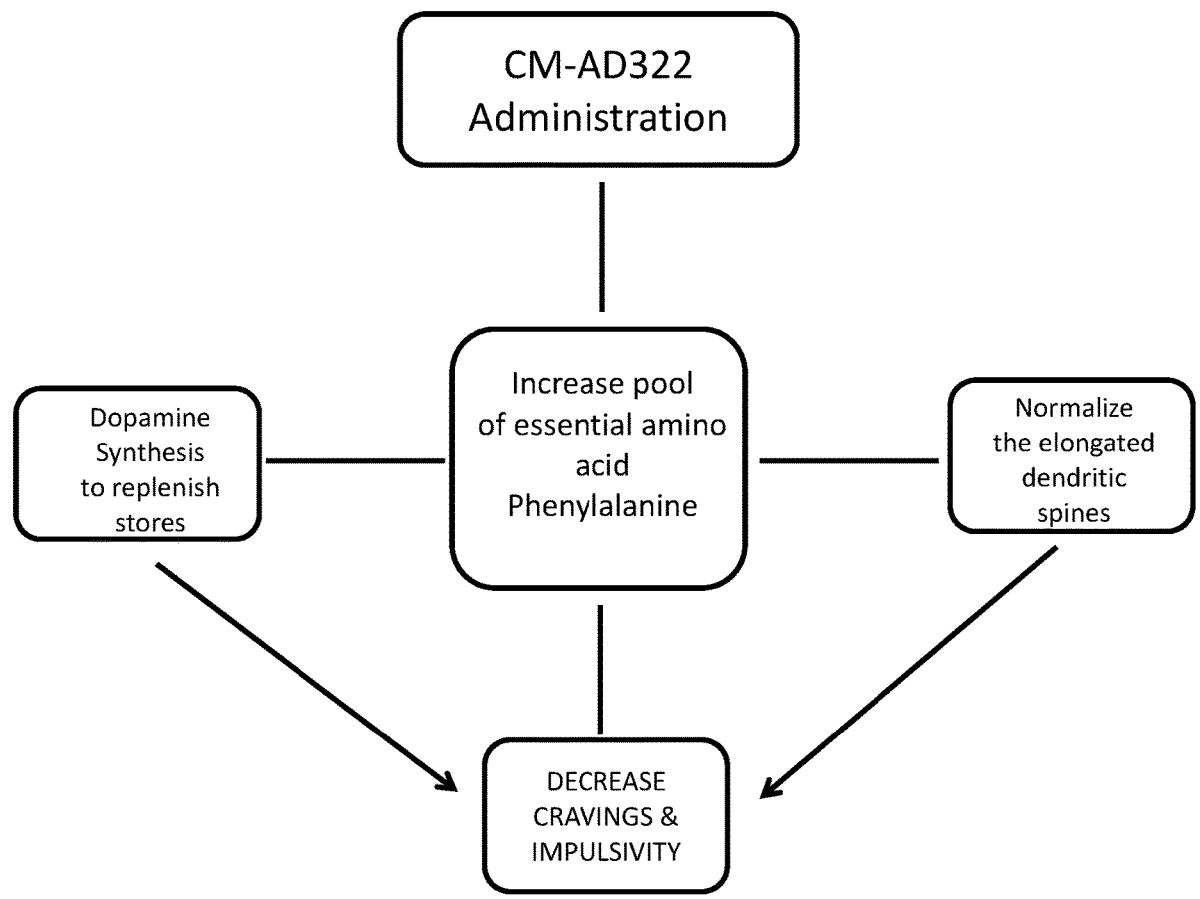
FIG. 3 illustrates a non-limiting example, of a mechanism of action of treatment of an addiction following administration of a pharmaceutical composition to a subject.

FIG. 3 illustrates the synthesis of thinking on the potential effectiveness of CM-AD322.

Due to ΔFosβ buildup and subsequent reinforcement of addictive behaviors, the effectiveness of CM-AD332 on cocaine cravings in active cocaine addicts is examined.

Standard measures of cravings and the addictive behaviors, as well as brain changes that occur as a result of the administration of CM-AD322 are assessed.

Dosage Form, Route of Administration, and Dosing Regimen

CM-AD322 is a formulation that comprises coated digestive enzyme particles, which particles contain a core comprising digestive enzymes and a lipid coating, where the digestive enzymes are present in the coated particles in an amount of from about 70% to about 90%. The digestive enzymes comprise a mixture of a protease, an amylase and a lipase. The coated digestive enzyme particles are encapsulated for administration to a subject as capsules. CM-AD322 delivers a high dose of protease to the subject in the amount of from about 135,000 to about 150,000 USP units of protease per capsule.

CM-AD322 is designed to release chymotrypsin and other proteases such as trypsin in the proximal small intestine without extreme degradation by stomach acid.

Chymotrypsin is a protease enzyme in the mixture of enzymes. It is a serine protease enzyme and one of the prominent proteases involved in human digestion. Chymotrypsin is unique because it cleaves proteins at the sites proximal to four essential amino acids. See, FIG. 1.

Due to ΔFosβ buildup and subsequent reinforcement of addictive behaviors, the effectiveness of CM-AD332 on cocaine cravings in active cocaine addicts is assessed.

Standard measures of cravings and the addictive behaviors, as well as brain changes that occur as a result of the administration of CM-AD322 are assessed.

CM-AD322 for treatment of cocaine addiction comprises coated digestive enzyme particles in capsule form.

Packaging

The capsule compositions can be packaged in blister packs with foil backing for size 00 or 0 capsules, dependent on fill characteristics.

Clinical supplies are manufactured under cGCP conditions.

Clinical Trial

The present example describes treatment of cocaine addiction in human subjects that are from about 16 to about 70 years old.

The trial design as presented may include active addicts as studied in the following treatment arms:

| Group A: Addicted | Group B: Addicted | Group C: Addicted |
|---|---|---|
| Dosage A | Dosage B | Placebo |

The trial design as presented may also include one group of non-addicted subjects as shown in the following treatment arms:

| Group A Addicted | Group B Addicted | Group C Addicted | Group D Non-addicted |
|---|---|---|---|
| Dosage A | Dosage B | Placebo | Placebo |

A placebo to be administered to the subjects of Groups C and/or D include compositions that do not comprise the digestive enzymes.

Subjects in the study are administered 5-8 capsules with each meal, three times daily, for at least 12 weeks. A subject will receive approximately 360,000 U.S.P. Units/per dose.

Primary Outcome Measures

A primary outcome measure to be tested is cocaine craving as measured by a cocaine craving questionnaire.

The cocaine craving questionnaire (CCQ) is a 45-item self-report questionnaire that assesses cocaine craving. The CCQ is an art-recognized method of assessing addiction cravings. The CCQ-Now version asks about current craving for cocaine, and the CCQ-general version asks about average craving over the preceding week Items for the questionnaire were generated to represent five distinct conceptualizations of cocaine craving: (1) desire to use cocaine; (2) anticipation of positive outcomes from cocaine use; (3) anticipation of relief from cocaine withdrawal symptoms or relief from negative mood; (4) intention and planning to use cocaine; (5) lack of control over use. The first 4 item categories were adapted from the QSU.

Secondary Outcome Measures

Secondary outcome measures that are to be measured are, for example, impulsivity and impulse control as measured by the Barratt Impulsiveness Scale. The Barratt Impulsiveness Scale (BIS-11; Patton et al., 1995, J Clin Psy, vol. 51, pp. 768-774) is an art-recognized questionnaire designed to assess the personality/behavioral construct of impulsiveness and to measure some of the ways in which a subject acts and thinks.

People differ in the ways they act and think in different situations; items are scored on a 4-point scale: Rarely/Never=1; Occasionally=2; Often=3; or Almost Always/Always=4.

| 1 | I plan tasks carefully. |
|---|---|
| 2 | I do things without thinking. |
| 3 | I make-up my mind quickly. |
| 4 | I am happy-go-lucky. |
| 5 | I don't "pay attention." |
| 6 | I have "racing" thoughts. |
| 7 | I plan trips well ahead of time. |
| 8 | I am self-controlled. |
| 9 | I concentrate easily. |
| 10 | I save regularly. |
| 11 | I "squirm" at plays or lectures. |
| 12 | I am a careful thinker. |
| 13 | I plan for job security. |
| 14 | I say things without thinking. |
| 15 | I like to think about complex problems. |
| 16 | I change jobs. |
| 17 | I act "on impulse." |
| 18 | I get easily bored when solving thought problems. |
| 19 | I act on the spur of the moment. |
| 20 | I am a steady thinker. |
| 21 | I change residences. |
| 22 | I buy things on impulse. |
| 23 | I can only think about one thing at a time. |
| 24 | I change hobbies. |
| 25 | I spend or charge more than I earn. |
| 26 | I often have extraneous thoughts when thinking. |
| 27 | I am more interested in the present than the future. |
| 28 | I am restless at the theater or lectures. |
| 29 | I like puzzles. |
| 30 | I am future oriented. |

Other Outcome Measures

This Phase II trial includes the following non-safety, non-functional MRI, exploratory outcome measures: Timeline Follow Back (TLFB); World Health Organization Quality of Life Questionnaire (WHOQOL-BREF); Hamilton Rating Scale for Depression (HAM-D); Urine Toxicology; Blood Phenylalanine/Leucine Ratio; Fecal Chymotrypsin; Body Mass Index; Initiation of Abstinence; and/or Length of Abstinence.

Neuroimaging Outcome Measures

A Phase II clinical trial also includes the following Exploratory Neuroimaging Outcome Measures during which the following will be assessed:

Tasks: Go/No-Go Response Inhibition Task; and/or Drug Cue Caving Task.

During this imaging test: Functional Magnetic Resonance Imaging (fMRI).

In addition, the following neuroimaging studies will be conducted: Diffusion Tensor Imaging (DTI) and/or Structural Magnetic Resonance Imaging (sMRI).

Example 2

Subjects are treated according to the methods of Example 1, and the level of phenylalanine in blood is measured prior to commencement of treatment, and at one or more times during treatment.

The blood level of phenylalanine in of addicted patients administered CM-AD322 or placebo are compared at each time point to a normal level of phenylalanine in healthy subjects (i.e., from about 2 mg/dL to about 6 mg/dL, or from about 120 micromolar to about 360 micromolar). Depending upon the blood level of phenylalanine, a practitioner can determine how to modify the treatment plan of the subject being treated, or to continue with the same treatment plan.

Blood levels of phenylalanine can also be measured at one or more time points after the subject has stopped treatment with CM-AD322 to determine if the subject should receive additional treatment.

Example 3

Context-induced reinstatement rodent models are utilized to assess the effect of digestive enzyme compositions described herein.

Laboratory animals (generally, Fisher 344 rats or Sprague-Dawley rats) are first trained to self-administer cocaine in an environment (termed context A) associated with a specific set of "background" stimuli (e.g., operant conditioning chamber fan, time of day, visual cues, tactile cues). Lever pressing is then extinguished in a different environment (termed context B) with a different set of "background" stimuli. During reinstatement testing under extinction conditions, exposure to context A previously paired with cocaine reinstates lever responding. In such a rodent model, there are two arms of the study: (1) animals which are administered cocaine and a placebo and (2) antibodies which are administered cocaine and a composition described herein. Each arm will include 4-6 rats. Methods of delivering cocaine to rodents in their water bottles are known in the art. Compositions as described herein can be administered with food. The procedure is based on a "renewal" procedure that has been used to assess the role of contexts in resumption of conditioned responses to aversive and appetitive cues after extinction. Responses in each arm are compared and statistical significance is determined.

Example 4

Discrete cues-induced reinstatement models are utilized to assess the effect of digestive enzyme compositions described herein.

Laboratory animals (generally, Fisher 344 rats or Sprague-Dawley rats) are first trained to self-administer cocaine; cocaine delivery is temporally paired with a discrete cue (e.g., tone, light, etc.). Lever pressing is then extinguished in the absence of cocaine and the cue. During reinstatement testing, exposure to the discrete cue, which is earned contingently during testing, reinstates lever responding. In such a rodent model, there are two arms of the study: (1) animals which are administered cocaine and a placebo and (2) antibodies which are administered cocaine and a composition described herein. Each arm will include 4-6 rats. Methods of delivering cocaine to rodents in their water bottles are known in the art. Compositions as described herein can be administered with food. Responses in each arm are compared and statistical significance is determined.

Example 5

Discriminative cues-induced reinstatement models are utilized to assess the effect of digestive enzyme compositions described herein.

Laboratory animals (generally, Fisher 344 rats or Sprague-Dawley rats) are trained to self-administer cocaine in the presence of distinct discriminative stimuli (e.g., visual cues, olfactory cues); one set of stimuli signals cocaine availability (S+) and the other signals unavailability (S−). Lever pressing is then extinguished in the absence of the discriminative stimuli and cocaine. During the reinstatement test, re-exposure to the S+, but not S−, reinstates operant conditioned responding. In such a rodent model, there are two arms of the study: (1) animals which are administered cocaine and a placebo and (2) antibodies which are administered cocaine and a composition described herein. Each arm will include 4-6 rats. Methods of delivering cocaine to rodents in their water bottles are known in the art. Compositions as described herein can be administered with food. Responses in each arm are compared and statistical significance is determined.

Example 6

Drug-priming-induced reinstatement models are utilized to assess the effect of digestive enzyme compositions described herein.

Laboratory animals (generally, Fisher 344 rats or Sprague-Dawley rats) are first trained to self-administer cocaine; typically cocaine delivery is paired with a discrete cue. Lever pressing is then extinguished in the presence of the discrete cue. During reinstatement testing under extinction conditions (usually, in the presence of the discrete cue), pre-session non-contingent priming injections of the previously self-administered cocaine or related cocaine reinstate lever responding. In such a rodent model, there are two arms of the study: (1) animals which are administered the drug and a placebo and (2) antibodies which are administered the drug and a composition described herein. Each arm will include 4-6 rats. Methods of delivering cocaine to rodents in their water bottles are known in the art. Compositions as described herein can be administered with food. Responses in each arm are compared and statistical significance is determined.

Example 7

Reinstatement models are utilized to assess the effect of digestive enzyme compositions described herein.

A reinstatement model is an animal model of cocaine relapse in which laboratory animals are tested for reinstatement of cocaine seeking induced by cocaine-priming, discrete cues, discriminative cues, contextual cues, and/or stressors, following cocaine self-administration training (typically lever-press or nose-poke for drug infusions) and subsequent extinction of the cocaine-reinforced responding. Less frequently used procedural variations of the reinstatement model include, for example, operant-conditioning-based runway and Pavlovian-conditioning-based conditioned place preference procedures. In such a rodent model, there are two arms of the study: (1) animals which are administered cocaine and a placebo and (2) antibodies which are administered cocaine and a composition described herein. Typically, Fisher 344 rats or Sprague-Dawley rats are utilized; each arm will include 4-6 rats. Methods of delivering cocaine to rodents in their water bottles are known in the art. Compositions as described herein can be administered with food. Responses in each arm are compared and statistical significance is determined.

Example 8

Stress-induced reinstatement models are utilized to assess the effect of digestive enzyme compositions described herein.

Laboratory animals (generally, Fisher 344 rats or Sprague-Dawley rats) are first trained to self-administer cocaine; cocaine delivery is temporally paired with a discrete cue. Lever pressing is then extinguished in the presence of the discrete cue. During reinstatement testing under extinction conditions (in the presence of the discrete cue), pre-session exposure to stressors (typically intermittent foot-shock or yohimibine injection) reinstates lever responding. In such a rodent model, there are two arms of the study: (1) animals which are administered cocaine and a placebo and (2) antibodies which are administered cocaine and a composition described herein. Each arm will include 4-6 rats. Methods of delivering cocaine to rodents in their water bottles are known in the art. Compositions as described herein can be administered with food. Responses in each arm are compared and statistical significance is determined.

Example 9

This example describes a multi-staged procedure, which started with the acquisition of cocaine IVSA, followed by several cycles of extinction and reinstatement.

Male C57BL/6J mice are obtained at the age of 8-9 weeks and housed four per cage with food and water ad libitum.

Each operant chamber is fitted with an AL (active lever) and an IAL (inactive lever), a cue light is positioned 45 mm above the center of the two levers, and a house light is positioned on the opposite wall of the chamber. The position of the AL is counterbalanced across individuals and within each group. Chambers are located in sound-attenuating containers with a fan that always is on during training sessions.

Mice are anesthetized and implanted with a chronic indwelling catheter.

One week after jugular catheter implantation, training of mice is initiated. The training sessions last 2 h/day, 5 days a week for 3-4 weeks. Each session starts with the house light on and both levers extended. For master mice, the training starts with an FR 1 (fixed ratio 1) schedule of reinforcement, during which one response to the assigned AL results in the programmed consequences, i.e., an IV drug injection through the pre-implanted catheter as well as illumination of the central cue light on and the extinguishing of the house light for 20 s (time-out, no more is was delivered after active response).

The criteria for moving from FR1 to FR5 phase includes: (1) earning a minimum of 20 reinforcers per session in two consecutive sessions; (2) varying in the number of infusions earned by no more than 20% in two consecutive sessions; (3) making at least 70% of all responses on the AL; and/or (4) the passage of at least 2 weeks in the FR1 phase. The FR5 training phase usually lasts 1-2 weeks and progresses to the extinction phase when no more than 20% variation in the number of reinforcers earned between the two sessions occurs.

Mice in a saline control group are trained with the same procedure except the cocaine solution is replaced with saline.

Mice in a treatment test group are trained with the same procedure except food is supplemented with coated digestive enzyme particles.

The training procedure of mice in the yoked group strictly follows that of the corresponding paired masters, except each drug delivery and presentation of visual cues are initiated by the paired masters.

Mice in all groups are trained in operant chambers with everything similar as in the acquisition phase except that all lever presses are recorded, but do not include programmed consequences. Subjects remain in extinction until no more than 20% variation in the number of AL responses between two consecutive sessions occurs, with a minimum of 2-week extinction period.

Four cycles of reinstatement testing are performed in all subjects 24 h after meeting the extinction criteria. In each cycle, mice are tested for their propensity to reinstate drug-seeking behavior after a challenge injection of cocaine (0, 1, 3.2 and 10 mg/kg IP, in random order) followed by at least 2-day re-extinction until they met again the extinction criteria.

The in vitro electrophysiological studies are performed 24 h after the last extinction session. The end point of behavioral training occurs when the subjects are at the extinction phase.

Data are assessed using analysis of variance (ANOVA). Post-hoc analyses are conducted using Tukey tests and analyses are considered statistically significant at $P<0.05$. All data are presented as mean±SEM. Correlations are generated using Pearson's product correlations to test for correlations of responses between the different reinstatement tests.

Example 10

Heroin addiction and treatment can be assessed using an art-recognized animal model. Male, Sprague-Dawley rats are individually housed and are given water ad libitum and are maintained on 25 g of standard rat chow per day for the duration of each experiment. Rats are acclimated to handling and allowed to adapt for a minimum of four days prior to the start of the experiment.

Rats are trained to lever press in standard self-administration chambers linked to a computerized data collection program (MED-PC, Med Associates, Inc., St. Albans, VT, USA). The chambers are equipped with two retractable levers, a white stimulus light above each lever, a food pellet dispenser between the levers, a tone generator, and a house light on the wall opposite the levers. Each chamber contains a sound-attenuating cubicle equipped with a ventilation fan. Rats are food deprived overnight and trained to lever press on a fixed ratio 1 (FR1) schedule of food reinforcement during a 15-h overnight training session in the absence of explicit conditioned stimulus (CS) presentation (i.e., active lever presses resulted in the delivery of a food pellet only).

Lever presses on an inactive lever are recorded. Following lever response training, food dispensers are permanently removed from the test chambers.

Rats are administered a placebo (control arm) or food containing coated digestive enzyme particles (test arm) with food.

Rats begin self-administration of heroin (diacetylmorphine HCl,) along a FR1 schedule at an initial dose of 50 µg/50 µl/infusion for 2 days, followed by 10-12 days of self-administration at a dose of 25 µg/50 µl/infusion. At the start of each 3-h session, the catheter is connected to a liquid swivel (Instech, Plymouth Meeting, PA) via polyethylene 20 tubing that was encased in steel spring leashes (Plastics One, Inc.). The swivels are suspended above the operant conditioning chamber and are connected to infusion pumps (model PHM-100, Med-Associates). The house light signals the initiation of the session and remains illuminated throughout the entire session. Active lever responses result in a 2 s activation of the infusion pump and a 5 s presentation of a conditioned stimulus complex (CS), which includes a cue light above the active lever and a tone (78 dB, 4.5 kHz). Following each infusion, responses on the active lever have no consequences during a 20 s time-out period. Inactive lever presses also have no consequences, and are were recorded.

After the last day of self-administration, rats experience daily 3-h extinction sessions. On the first session, a catheter is connected to the swivel; however, no drug is administered. On subsequent sessions, rats are placed into the chamber without being attached to the swivel. Throughout extinction training, the house light signals the initiation of the session and remains illuminated during the session. Responses on either the active or inactive lever are recorded, but resulted in no programmed consequences (i.e., no infusion and no CS presentation). Animals continue under extinction conditions until they reached a criterion of a minimum of 10 days and ≤25 lever presses per session for two consecutive days.

Following extinction, rats undergo four reinstatement tests, using a counterbalanced, within subjects design, with a minimum of 2 days of extinction between each test. Immediately prior to each reinstatement test, the rats receive either intracranial vehicle or B/M. During the first two reinstatement tests, rats are placed into the chambers for 3 h, during which the house light is illuminated and each active lever press results in a 5 s CS presentation in the absence of any drug reinforcement, followed by a 20 s time out period. For heroin-primed reinstatement tests, a single, non-contingent dose of heroin (0.25 mg/kg, s.c.) is administered immediately prior to the rat entering the chamber for a 3 h session, during which the house light is illuminated and lever responses have no programmed consequences (i.e., no CS presentation).

Lever responses and heroin intake during self-administration, as well as lever responses during extinction, CS-induced, and heroin-primed reinstatement testing are assessed using analysis of variance (ANOVA). Post-hoc analyses are conducted using Tukey tests and analyses are considered statistically significant at P<0.05. All data are presented as mean±SEM. Correlations are generated using Pearson's product correlations to test for correlations of responses between the different reinstatement tests.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. A method of reducing an elevated amount of ΔFos in a subject having an addiction, wherein ΔFos is elevated in the subject due to the addiction compared to a subject without the addiction, the method comprising: ¶
   (a) selecting the subject to be treated when the subject is diagnosed with a blood level of phenylalanine of from 1 mg/dL to 3 mg/dL or with a blood level of phenylalanine of from 60 to 120 micromolar, and
   (b) administering to the subject a therapeutically effective amount of a pharmaceutical composition that comprises digestive enzymes, wherein ΔFos is reduced upon administration of the pharmaceutical composition to the subject.

2. The method of claim 1, wherein the digestive enzymes comprise an amylase, a lipase, and a protease.

3. The method of claim 1, wherein the digestive enzymes in the pharmaceutical composition further comprise a lipid coating.

4. The method of claim 1, wherein the pharmaceutical composition is encapsulated.

5. The method of claim 1, wherein a dose of the pharmaceutical composition comprises about 4, about 5, about 6, about 7, about 8, or about 9 capsules, tablets, or sachets.

6. The method of claim 1, wherein the addiction comprises a drug addiction, and wherein the drug comprises an opiate.

7. The method of claim 6, wherein the opiate comprises a natural opiate, a synthetic opiate, or a combination thereof.

8. The method of claim 7, wherein the opiate comprises the synthetic opiate, and wherein the synthetic opiate is selected from the group consisting of hydromorphone hydrochloride, meperidine, Oxycodone, hydrocodone and acetaminophen, Fentanyl, Methadone, and a combination thereof.

9. The method of claim 2, wherein a total protease and a total lipase in the pharmaceutical composition in U.S.P. units are present in a ratio of protease to lipase of from about 1:1 to about 20:1.

10. The method of claim 2, wherein a total protease and a total amylase in the pharmaceutical composition in U.S.P. units are present in a ratio of protease to amylase of from about 1:0.1 to about 1:10.

11. The method of claim 1, wherein the pharmaceutical composition comprises coated digestive enzyme particles.

12. The method of claim 1, wherein the pharmaceutical composition comprises coated digestive enzyme particles that are encapsulated.

13. The method of claim 11, wherein the coated digestive enzyme particles comprise (i) a core that comprises the digestive enzymes, and (ii) a coating.

14. The method of claim 13, wherein the coating comprises a lipid.

15. The method of claim 14, wherein the lipid comprises a pharmaceutical grade lipid.

16. The method of claim 15, wherein the pharmaceutical grade lipid comprises a fully-hydrogenated soybean oil.

17. The method of claim 14, wherein the lipid comprises a hydrogenated lipid, a partially saturated lipid, or a combination thereof.

18. The method of claim 14, wherein the lipid comprises a soy lipid.

19. The method of claim 18, wherein the soy lipid comprises a hydrogenated soy lipid.

20. The method of claim 1 wherein the pharmaceutical composition is administered to the subject orally.

21. The method of claim 11, wherein the coated digestive enzyme particles are encapsulated in a gelatin capsule or a hydroxypropyl methylcellulose (HPMC) capsule.

22. The method of claim 1, wherein the subject is administered one or more doses of the pharmaceutical composition.

23. The method of claim 22, wherein a dose of the pharmaceutical composition comprises from about 100 to about 9,000 mg of the digestive enzymes.

24. The method of claim 11, wherein the digestive enzymes are present in the coated digestive enzyme particles in an amount of from about 70% to about 90% by weight, or from about 75% to about 85% by weight.

25. The method of claim 24, wherein the digestive enzymes are present in the coated particles in an amount of about 75% by weight.

26. The method of claim 24, wherein the digestive enzymes are present in the coated particles in an amount of about 77.5% by weight.

27. The method of claim 24, wherein the digestive enzymes are present in the coated particles in an amount of about 80% by weight.

28. The method of claim 24, wherein the digestive enzymes are present in the coated particles in an amount of about 82.5% by weight.

29. The method of claim 24, wherein the digestive enzymes are present in the coated particles in an amount of about 85% by weight.

30. The method of claim 11, wherein at least 90% of the coated particles are from about 105 μm to about 425 μm in size.

31. The method of claim 11, wherein at least 75% of the coated particles are from about 180 μm to about 425 μm in size.

32. The method of claim 11, wherein less than about 20% of the coated particles are capable of being sieved through about 150 μm mesh.

33. The method of claim 11, wherein less than about 15% of the coated particles are capable of being sieved through about 150 μm mesh.

34. The method of claim 1, wherein the ΔFos comprises ΔFosβ.

35. The method of claim 2, wherein a dose of the pharmaceutical composition comprises from about 650,000 U.S.P. units to about $1.5 \times 10^6$ U.S.P. units of the protease.

* * * * *